United States Patent
Friedman

(10) Patent No.: US 11,776,266 B1
(45) Date of Patent: Oct. 3, 2023

(54) ASSESSING PLAYER PERFORMANCE IN A SPORT USING A GRAPHICAL USER INTERFACE

(71) Applicant: Zvi Friedman, Sylmar, CA (US)

(72) Inventor: Zvi Friedman, Sylmar, CA (US)

(*) Notice: Subject to any disclaimer, the term of this patent is extended or adjusted under 35 U.S.C. 154(b) by 0 days.

(21) Appl. No.: 18/052,156

(22) Filed: Nov. 2, 2022

Related U.S. Application Data

(60) Provisional application No. 63/294,584, filed on Dec. 29, 2021.

(51) Int. Cl.
G06K 9/00 (2022.01)
G06V 20/40 (2022.01)
A63B 24/00 (2006.01)

(52) U.S. Cl.
CPC .......... *G06V 20/42* (2022.01); *A63B 24/0021* (2013.01); *A63B 2024/0025* (2013.01); *A63B 2024/0056* (2013.01)

(58) Field of Classification Search
CPC ............. G06T 7/20; G06T 2207/10016; G06T 2207/30224; G06T 2207/30221; G06T 2207/30241; G06T 7/246; G06T 7/74; G06T 7/70; G06T 11/006; G06T 2207/30008; G06T 7/248; G06T 2207/30228; G06T 7/73; G06T 7/80; G06T 2207/20084; G06T 2207/20132; G06T 2207/30196; G06T 2207/30244; G06T 7/0004; G06T 7/75; G06T 7/85; G06T 13/00; G06T 2207/30141; G06T 2207/30201; G06T 2210/41; G06T 7/0012; G06T 7/30; G06T 7/90; G06T 11/005; G06T 15/30; G06T 19/006; G06T 2207/10081; G06T 2207/10116; G06T 2207/20081; G06T 2207/30148; G06T 2207/30164; G06T 2207/30204;

(Continued)

(56) References Cited

U.S. PATENT DOCUMENTS

| | | | | |
|---|---|---|---|---|
| 2007/0087827 A1* | 4/2007 | Hirota | ..................... | A63F 13/30 463/40 |
| 2010/0134614 A1* | 6/2010 | Aman | ................ | A63B 24/0003 348/157 |
| 2016/0071548 A1* | 3/2016 | House | .................. | H04N 5/2624 386/201 |

OTHER PUBLICATIONS

Xu, "Dynamic-Group-Aware Networks for Multi-Agent Trajectory Prediction with Relational Reasoning," arXiv, Jun. 27, 2022 (Year: 2022).*

* cited by examiner

*Primary Examiner* — Alex Kok S Liew
(74) *Attorney, Agent, or Firm* — Perkins Coie LLP

(57) ABSTRACT

Systems and methods for assessing performance of a player or a team comprising a plurality of players are described. An example method includes receiving a pass distribution matrix corresponding to a number of completed passes within a field of play for one or more players of the plurality of players, selecting a particular player from the one or more players, and generating a spine for the team. In an example, generating the spine for the team includes producing a visual representation of the field of play that illustrates a position of the particular player and at least one other player within the field of play, and automatically varying, on the visual representation, a thickness of each of a plurality of connecting lines between the particular player and the at least one other player based on the number of completed passes for the particular player.

25 Claims, 88 Drawing Sheets
(70 of 88 Drawing Sheet(s) Filed in Color)

(58) Field of Classification Search
CPC ..... G06T 2211/436; G06T 3/40; G06T 7/001; G06T 7/11; G06T 7/149
See application file for complete search history.

LIST of "GOALS for a Center Forward- "Role Model"
The Player Main Goal's 1.0 Learn to cover your primary playing area (PPA- "A")
2.0 Learn to cover your primary playing area (PPA-"B&C")
3.0 Create 4 shots on Goal(both feet & Head)
4.0 Create 2 shots on Target
5.0 Score 1 Goal > The player playing & working Independent of other players/ Teammates(being proactive)

The Player's Supportive Job of his Goal 6.0 Create (13) total passes into the scoring box
7.0 create (6) Completed passes into the scoring box. Add Completion ratio into the scoring box(%)
8.0 Create Total forward passes (19)into the offensive part of the of the playing
9.0 Create(8) completed forward passes into offensive part of the of the playing
10.0 Create (31)Total Passes +(report of completion Ratio )
11.0 Create( 16) Completed Passes (41)
12.0 Corner kicks(1)

> The player playing &working with other players/teammates (the player maybe working on Tactical aspects)

13.0 Intercept Total(6) passes in the attacking 1/3
14.0 No lost passes in the defensive 1/3

> The player playing to support the Defensive aspect.

FIG. 24A

Joey: you need additional work to accomplish your GOAL

Joey: you need additional work to accomplish your GOAL

Joey: you need additional work to accomplish your GOAL

Joey: you need additional work to accomplish your GOAL

Legend
- Completed Pass
- Lost Pass

Joey: you accomplished your GOAL

| | A | B | C | D | E | F | G | H |
|---|---|---|---|---|---|---|---|---|
| 1 | Second Look Version 2.4 | | | | | | | |
| 2 | Paraguay vs. Argentina | | | | | | | |
| 3 | 6-Jul-97 | | | | | | | |
| 4 | | | Receivers Number | 15 | 2 | 20 | 16 | 9 |
| 5 | | | Name | Ferreira, \ | Alcaraz, J. | Soto, O. | Enciso, J.C | Cardoza, J |
| 6 | Passers | | Team | Paraguay | Paraguay | Paraguay | Paraguay | Paraguay |
| 7 | Number | Name | Team | | | | | |
| 8 | 15 | Ferreira, \ | Paraguay | 0 | 0 | 0 | 0 | 1 |
| 9 | 2 | Alcaraz, J. | Paraguay | 1 | 0 | 4 | 0 | 0 |
| 10 | 20 | Soto, O. | Paraguay | 0 | 0 | 0 | 1 | 0 |
| 11 | 16 | Enciso, J.C | Paraguay | 0 | 0 | 1 | 0 | 3 |
| 12 | 9 | Cardoza, J | Paraguay | 2 | 0 | 2 | 3 | 0 |
| 13 | 14 | Jara, J. | Paraguay | 0 | 2 | 0 | 5 | 11 |
| 14 | 10 | Acuna, R. | Paraguay | 5 | 1 | 1 | 5 | 1 |
| 15 | 18 | Rojas, A. | Paraguay | 0 | 2 | 0 | 5 | 3 |
| 16 | 19 | Rojas, R. | Paraguay | 2 | 0 | 0 | 4 | 3 |
| 17 | 5 | Ayala, C. | Paraguay | 0 | 1 | 1 | 1 | 4 |
| 18 | 4 | Gamara, C | Paraguay | 1 | 0 | 7 | 2 | 1 |
| 19 | 8 | Esteche, F | Paraguay | 0 | 0 | 0 | 2 | 2 |
| 20 | 6 | Struway, \ | Paraguay | 0 | 0 | 3 | 5 | 0 |
| 21 | 22 | Ruiz Diaz, | Paraguay | 0 | 0 | 1 | 0 | 2 |

ASSESSING PLAYER PERFORMANCE IN A SPORT USING A GRAPHICAL USER INTERFACE

CROSS-REFERENCE TO RELATED APPLICATION

This patent document claims priority to and benefits of U.S. Provisional Patent Application No. 63/294,584 entitled "ACQUISITION, ANALYSIS AND ASSESSMENT OF A PLAYER PERFORMANCE IN A SPORT" and filed on Dec. 29, 2021. The entire contents of the before-mentioned patent applications are incorporated by reference as part of the disclosure of this patent document.

TECHNICAL FIELD

This document generally relates to training players, and more particularly to assessing and improving player performance in team sports.

BACKGROUND

Soccer is a popular sport that is played and enjoyed worldwide. Coaches, players, and other students of the game always endeavor to find new ways of teaching, learning, and enhancing techniques and skills for playing the game. However, because coaches have limited time and resources, they often do not have the time to research all aspects of how to improve a player's performance in sport such as soccer. To that end, a multitude of devices and training methods have been developed to aid players in honing their skills.

SUMMARY

Disclosed are systems, devices, and methods for assessing and analyzing player performance in a team sport. The described embodiments, among other features and benefits, provide a new approach for the development of soccer players, and help the coaching staff teach players to do their best and improve their performances in an effective and efficient manner. In an example, this is achieved by quantifying one or more skill metrics that include interactions with other team members, and analyzing the results over multiple games. These and other objectives are achieved using easy-to-use and convenient collection tools in conjunction with an underlying assessment engine that incorporates logical operations to produce assessment results including intuitive graphical presentations that provide subjective measures of a player's or a team's performance, the player's or the team's objectives, and other information regarding the team or player.

The disclosed methodology and systems can also be applied to other team sports that can benefit from objective analysis of player performance, and a systematic way to improve the individual athlete's, as well as the team's, performance.

In one example, a method for assessing performance of a player or a team comprising a plurality of players is disclosed. The method includes receiving a pass distribution matrix corresponding to a number of completed passes within a field of play for one or more players of the plurality of players, selecting a particular player from the one or more players, and generating a spine for the team. In an example, generating the spine for the team includes determining a total number of completed passes between the particular player and each of the one or more players by using a processor to track the number of passes for the particular player based on the pass distribution matrix, producing a visual representation of the field of play that illustrates a position of the particular player and at least one other player within the field of play, the visual display further including connecting lines indicative of a number and direction of passes between the particular player and at least one other player, and automatically varying, on the visual representation, a thickness of each of a plurality of connecting lines between the particular player and the at least one other player based on the number of completed passes for the particular player, wherein the thickness is representative of the number of completed passes.

In another example, a system for assessing performance of a player or a team comprising a plurality of players. The system includes a processor and a memory including instructions stored thereupon, wherein the instructions upon execution by the processor cause the processor to receive a pass distribution matrix corresponding to a number of completed passes within a field of play for one or more players of the plurality of players, select a particular player from the one or more players, and generate a spine for the team. In this example, generating the spine for the team further causes the processor to determine a total number of completed passes between the particular player and each of the one or more players by using a processor to track the number of passes for the particular player based on the pass distribution matrix, produce a visual representation of the field of play that illustrates a position of the particular player and at least one other player within the field of play, the visual display further including connecting lines indicative of a number and direction of passes between the particular player and at least one other player, and automatically vary, on the visual representation, a thickness of each of a plurality of connecting lines between the particular player and the at least one other player based on the number of completed passes for the particular player, wherein the thickness is representative of the number of completed passes.

In yet another example, the methods may be embodied in the form of processor-executable instructions and stored on a computer-readable program medium.

The subject matter described in this patent document can be implemented in specific ways that provide one or more of the following features.

BRIEF DESCRIPTION OF THE DRAWINGS

This application contains at least one drawing executed in color. Copies of this application with color drawing(s) will be provided by the Office upon request and payment of the necessary fees.

FIGS. 24A and 24B illustrate a list of example goals and their diagrammatic views, respectively, in accordance with the described embodiments.

FIGS. 70A-70F illustrate the different steps of generating a spine for a team and an individual player, in accordance with the described embodiments.

DETAILED DESCRIPTION

Figure 1:
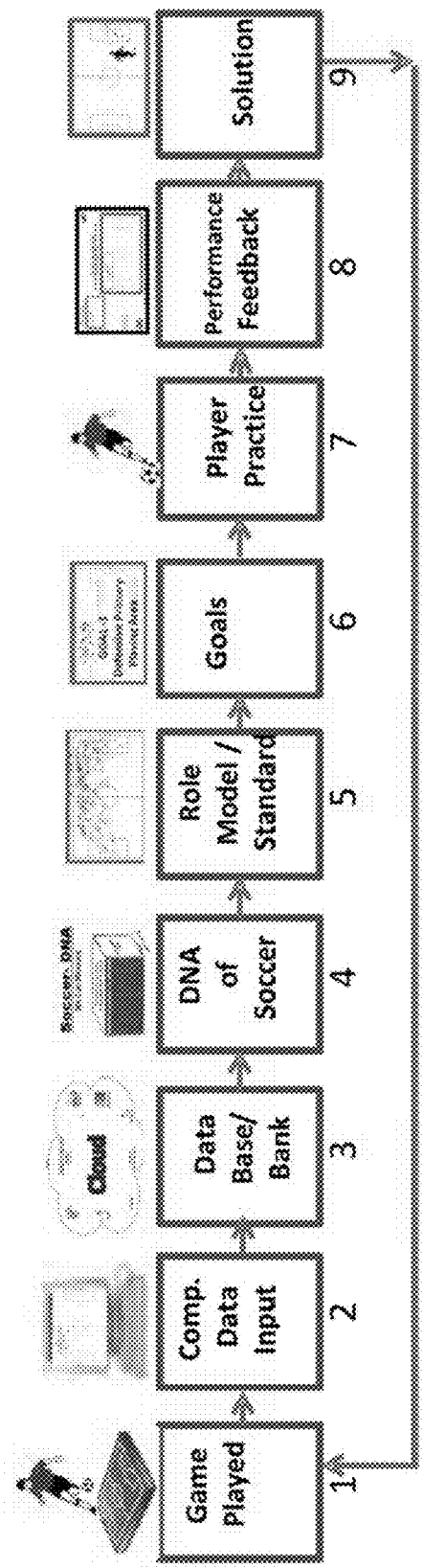
FIG. 1 illustrates a flowchart of an example method for assessing and analyzing player performance in a team sport in order to provide recommendations for improvement, in accordance with the described embodiments.

"Goal setting" can improve a player's performance, quality of practices, clarify expectations, and relieve boredom by making training more challenging. It also can increase motivation, communication, pride, satisfaction, and self-confidence. One difficulty in goal setting for soccer players is the issues of providing measurable feedback and Role Models to the players in order to allow comparison of the player's performance to a particular player, such as an elite professional player in the world.

The described embodiments provide, inter alia, objective measurement of player performance efficacy and efficiency. In an example, this is achieved by objectively breaking down all the activities of a team and individual players of the team, as well as those of the opponents, and providing performance reports with particular granularity (e.g., minute-by-minute to averaged across several games). The disclosed technology compares and breaks down the player's performance, categorizing success and failure, and visually showing trends and tendencies in order to improve their performance.

Section headings are used in the present document for clarity of understanding and do not limit the scope of the techniques and embodiments disclosed in each section only to that section. Furthermore, although several embodiments are described in the context of soccer, the disclosed technology is applicable to a number of other sports and endeavors.

Road to Success Using Goal Setting—DNA for Soccer

Analyzing a soccer player's performance is inherently problematic because of lack of data, information, and "Role Models," and standards to objectively measure and compare player performance. This is a great time to enter into the world of soccer. Never before there has been more possibilities and opportunities for boys and girls to achieve their "soccer goal." Never before in history are you actually drowning in so many options of what to do. If you are like most people today, you are overwhelmed with too much to do and too little time. The problem is how to do it in the limited time you have. Life is full of accomplishments. Some are small, some are big, some are recognized by the person who sets the goal, some never recognized, most can be measured, but others can't. Some have a few steps, and some have many steps, but they all require a "goal," a good plan, and hard work in order to accomplish their "goal." To have a good plan you must have a goal.

The described embodiments provide, inter alia, methods and systems that are designed to educate and give players, coaches, and parents, the best tools available in order to do their best, have fun, and accomplish their "goal."

In some embodiments, a system of measurable tools for soccer (as well as other sports) use a systematic approach in order to accomplish the desired goals. In some embodiments, performances by the best soccer players at the highest level in the world are used as the baseline. The described methods and systems can be used by a new player for player development, as well as professional players for improvement of their skills. In all cases, the described embodiments provide the player with feedback on their progress.

Some of the categories of performance that are provided by the disclosed embodiments include, but are not limited to, total passes, lost passes, and passes into the scoring box. Each one of these categories are referred to as "player goals" or "goals." These goals become the "standard." In some embodiments, a "Role Model" for a forward position is selected. The performance is then broken down into a number of categories (e.g., 14 categories), which include both offensive and defensive categories.

In some embodiments, the system of "goals" is produced in a logical step-by-step process for learning, which provides a base for training for an individual player. Once the player selects a goal, he will develop a plan on how to accomplish his goal through the specific features and technical improvements provided by some of the described embodiments, which can also be complemented by other resources, such as coaches, other players, etc. In particular, the player will work on the field, play games, and test his (or her) performance. The systems and methods described herein include technological tools that enable the capture of the player's performance during, or after, the game. The collected data (information) is processed and used to provide feedback to the player about their performance, and to determine whether or not the player has accomplished their goal. As discussed in the various embodiments, the provided information and feedback is both visual and quantitative.

Presenting a final conclusion is not the way we learn. The disclosed embodiments provide options and solutions to a player that resemble deductive thinking and processes through a series of ideas where one thought leads to the next thought, to facilitate a player's achievement of goals. As such, the methods and systems described herein do not merely present the user with a series of end results, but rather provide a "goal" that enables the player to go through the deduction process and find solutions for themselves as to how to accomplish their "goal." The disclosed embodiments can be used at all levels of soccer; from youth to adult, and from amateur to professional.

Soccer is a game where a team of players are involved in an activity that pits them against an opposing team. To play a game of soccer, you first need a ball. Then an opponent. Add a field, a couple of goals across from each other, mix in a few soccer rules and you have a game. Soccer also involves the element of chaos, as opponents, teammates, and the ball are all moving in different directions. Players, parents, and coaches are shouting different instructions and information. Bringing "order out of chaos" is an important skill in learning how to play the game that is facilitated in-part by the disclosed techniques.

Figure 2A:
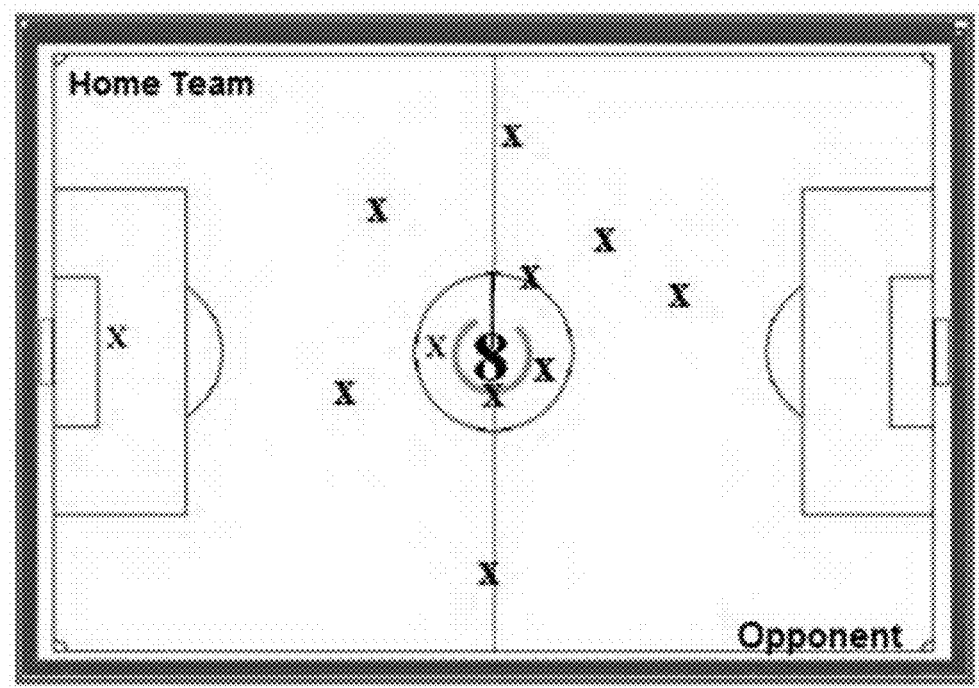
FIG. 2A illustrates a traditional drawing of player locations on a soccer field.
Figure 2B:
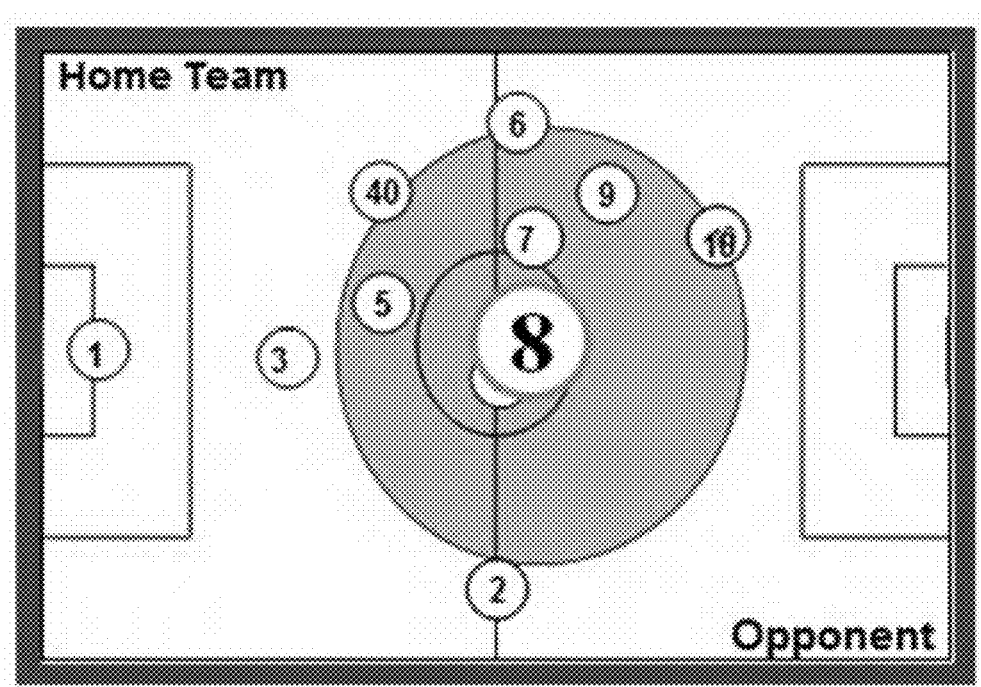
FIG. 2B illustrates an example of an improved drawing of player locations on a soccer field, in accordance with the described embodiments.

FIG. 1 illustrates a series of operations that can be carried out in accordance with some example embodiments. The steps in FIG. 1 are discussed in the context of other figures, including FIGS. 2A and 2B, which compare an example of a traditional diagram of soccer with an example diagram of how the disclosed embodiments can enable an improved presentation of that can improve the learning curve. FIG. 2A is a traditional drawing of player location on the field, wherein an "X" mark drawn by coaches provides a general area of play on the field. But the diagram in FIG. 2A does not define the borders of the dynamic primary playing area. In contrast, FIG. 2B illustrates the approach based on example embodiments for communicating the primary area of play that allows the coach to give the player a specific border of his primary playing area, and to give visual and measurable criteria of what the player is (or should be) actually doing. In this sample as illustrated by FIG. 2B, the primary playing area (shown by the large circle) corresponds to a player's dynamic primary playing area. The circle with number 8 represents the center of the player's activities.

Figure 3:
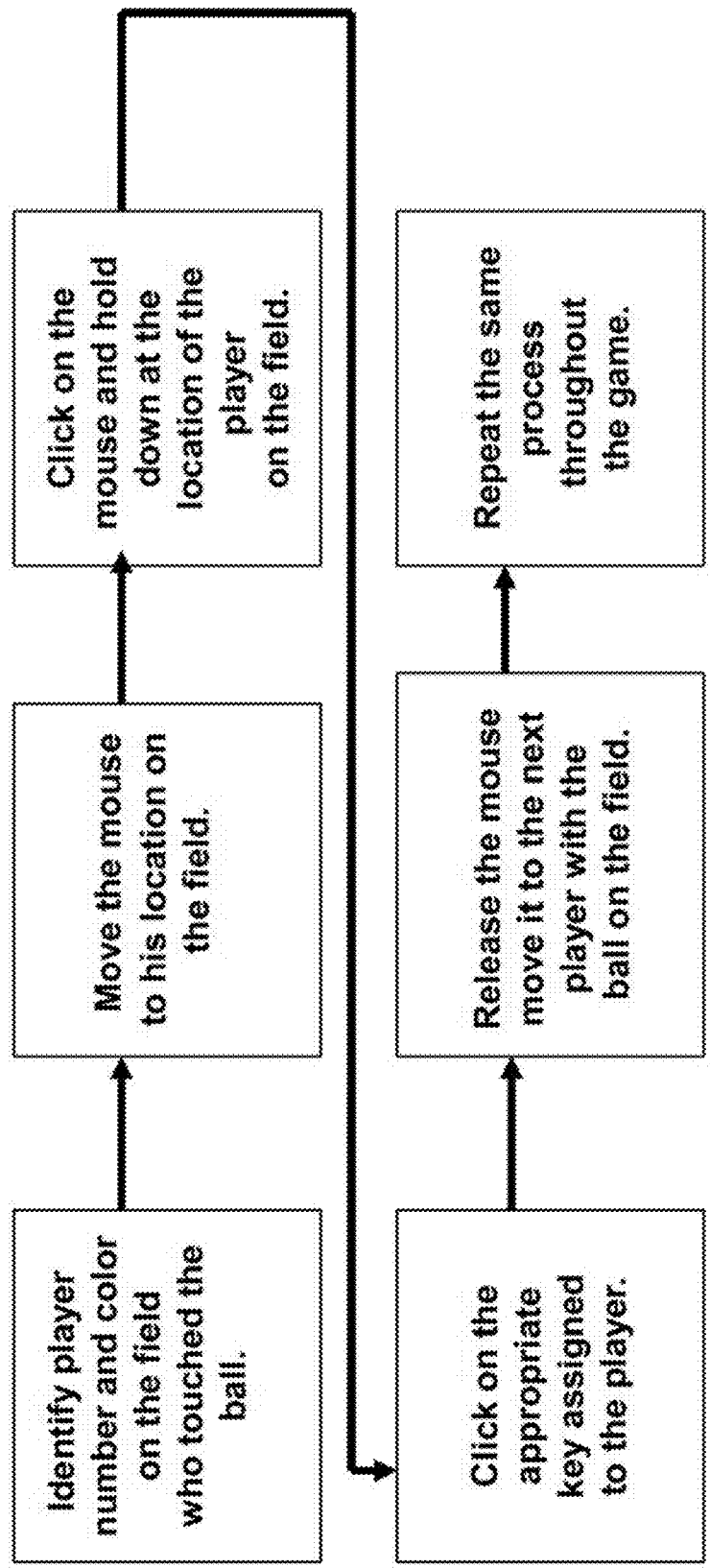
FIG. 3 illustrates a flowchart of an example set of operations for data input or collection, in accordance with the described embodiments.

FIG. 3 provides a set of example operations that can be used to input data (e.g., in steps 1 and 2 of FIG. 1). These operations can be carried out using a data input device, such as a personal computer, a laptop, a tablet, a smart phone, and the like. In step 2 of FIG. 1, the input data is compiled. In the example diagram of FIG. 3, data collection is carried out using a software product that analyzes the full ninety minutes of a soccer match and provides many detailed reports on team performance, and all individual player performance, thereby providing an overall view of the game's tactics and strategy (e.g., Second Look™).

In some embodiments, data is entered for more than one team member (e.g., all team members and/or all players of the opposing team) for the duration of game. While it may be possible to conduct the operations of FIG. 3 during the game as it is being played (e.g., by using multiple computers and/or several people to perform live data entry), these operations may be more reliably performed after the game by, for example, watching a video of the game. In some embodiments, data collection can be done for only a single person using a system developed according to the disclosed embodiments and is referred to as "MPG." In this case, the operations that are depicted in FIG. 3 can be simplified since there is no need to, for example, identify the player, or move the to the next player, etc. In case of MPG, the data can be simply entered for a single player, as the game is being played by, for example, clicking on a button that logs a completed pass, another button that logs a completed corner kick, clicking on areas of display to indicate start and end points of a pass, etc.

Figure 4:
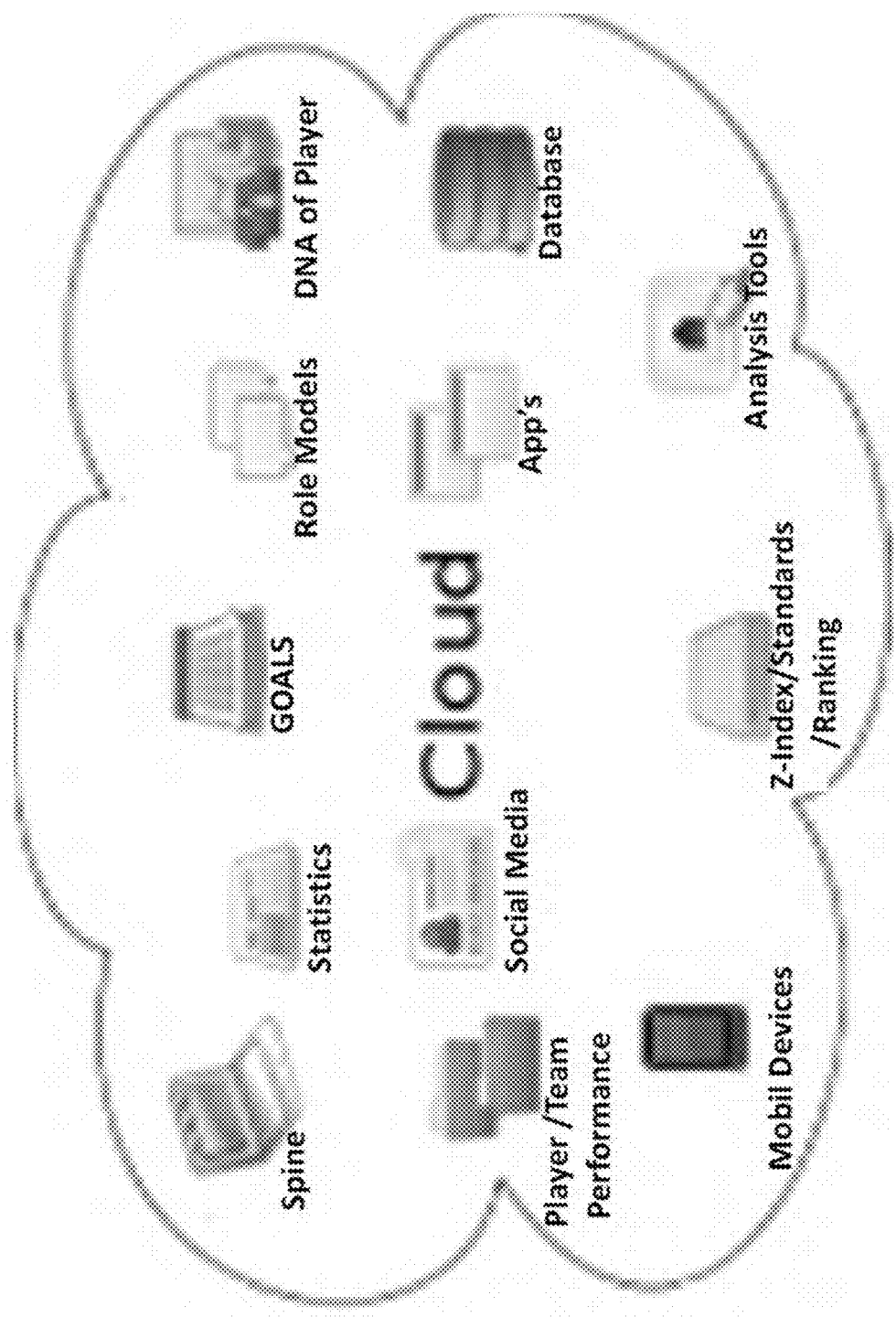
FIG. 4 illustrates an example of cloud-based storage and its contents, in accordance with the described embodiments.

FIG. 4 illustrates an example of a cloud-based storage location and its contents that can accommodate the database (e.g., in step 3 of FIG. 1). Some or all of the contents that are depicted in FIG. 4 are produced and/or processed based on the described embodiments.

Figure 5:
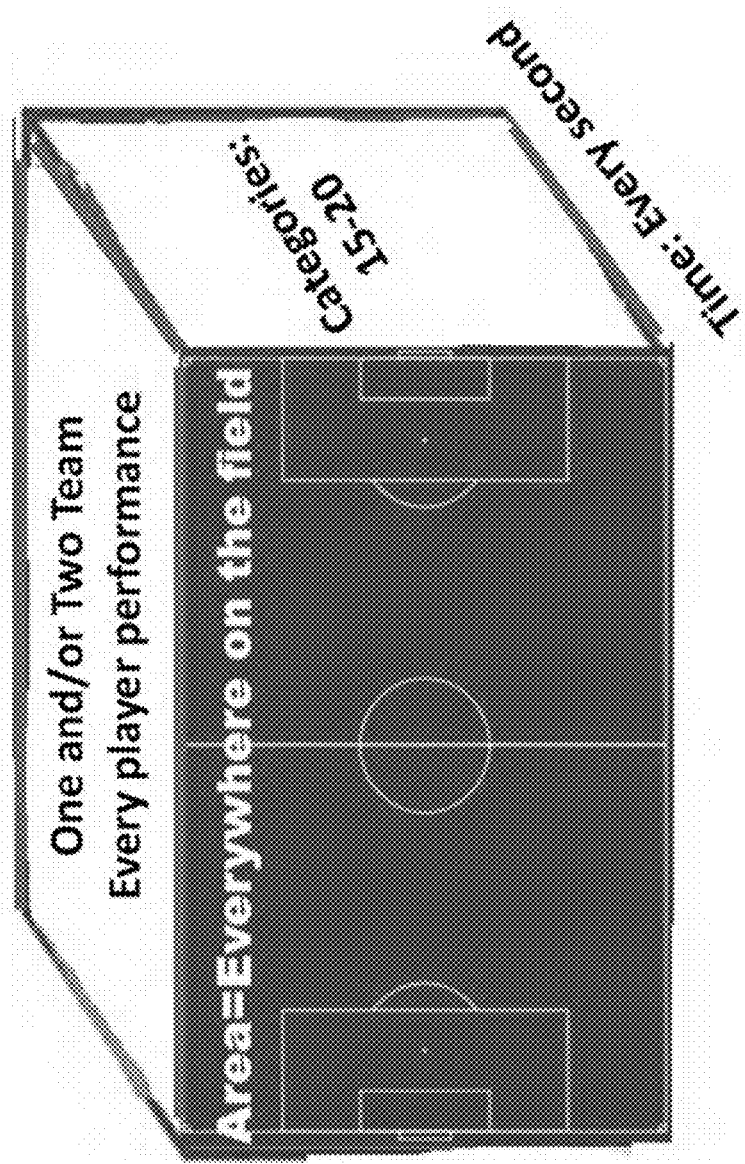
FIG. 5 illustrates an example of the granularity used for data input or collection, in accordance with the described embodiments.

In some embodiments, and as shown in step 4 of FIG. 1, the DNA of soccer is generated. The biological description of DNA states that DNA transfers hereditary information from one generation to another. Analogous to this definition, in step 4 of FIG. 1, the DNA of soccer is captured. The performance (e.g., the detailed structure) of a target player, such as one of the best players in the world, is captured and measured. The information associated with the DNA can be used for presentation of a Role Model and providing goals for potentially any user of the disclosed systems to emulate. In particular, the disclosed systems collect data with a particular granularity (e.g., every second, every minute, etc.) of the game, everywhere on the field, for each player of both teams, and for a number (e.g., 15-20) of different categories, as depicted in FIG. 5.

Figure 6A:
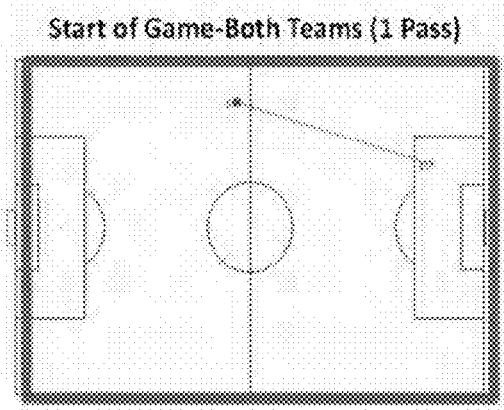
FIGS. 6A-6E illustrate examples of data collection at different times in a 90-minute soccer game, in accordance with the described embodiments.
Figure 6B:
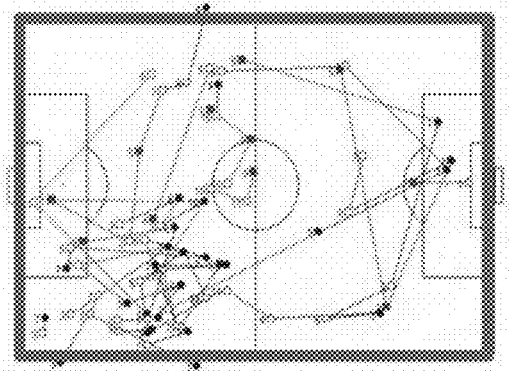
Figure 6C:
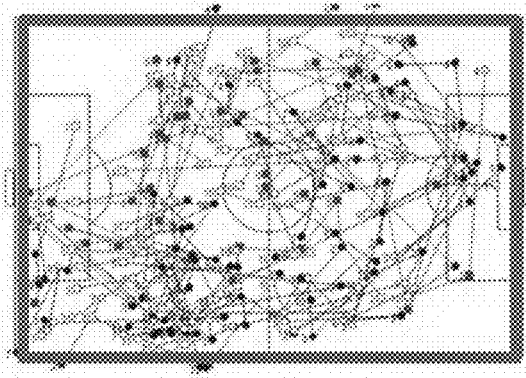
Figure 6D:
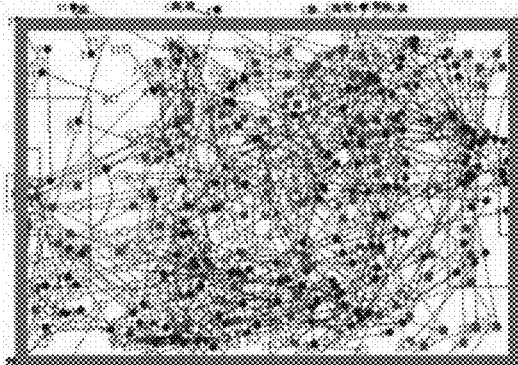
Figure 6E:
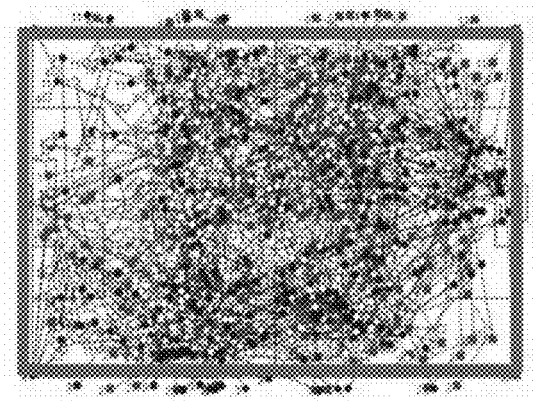

FIGS. 6A to 6E illustrate the process of data collection and data compilation, in accordance with the some example embodiments. In an example, data can be collected every second of the game. The example diagram shown in FIG. 6A illustrates a first completed pass at the start of the game. In FIG. 6B, the data collected for the first five minutes for both teams (red squares and blue circles) is illustrated. FIGS. 6C, 6D, and 6E show the collected data for the first 25 minutes, the first 45 minutes, and the entire 90 minutes of play, respectively. The figures also illustrate whether a pass was completed (filled circles or squares) or lost (open circles or squares).

Figure 7:
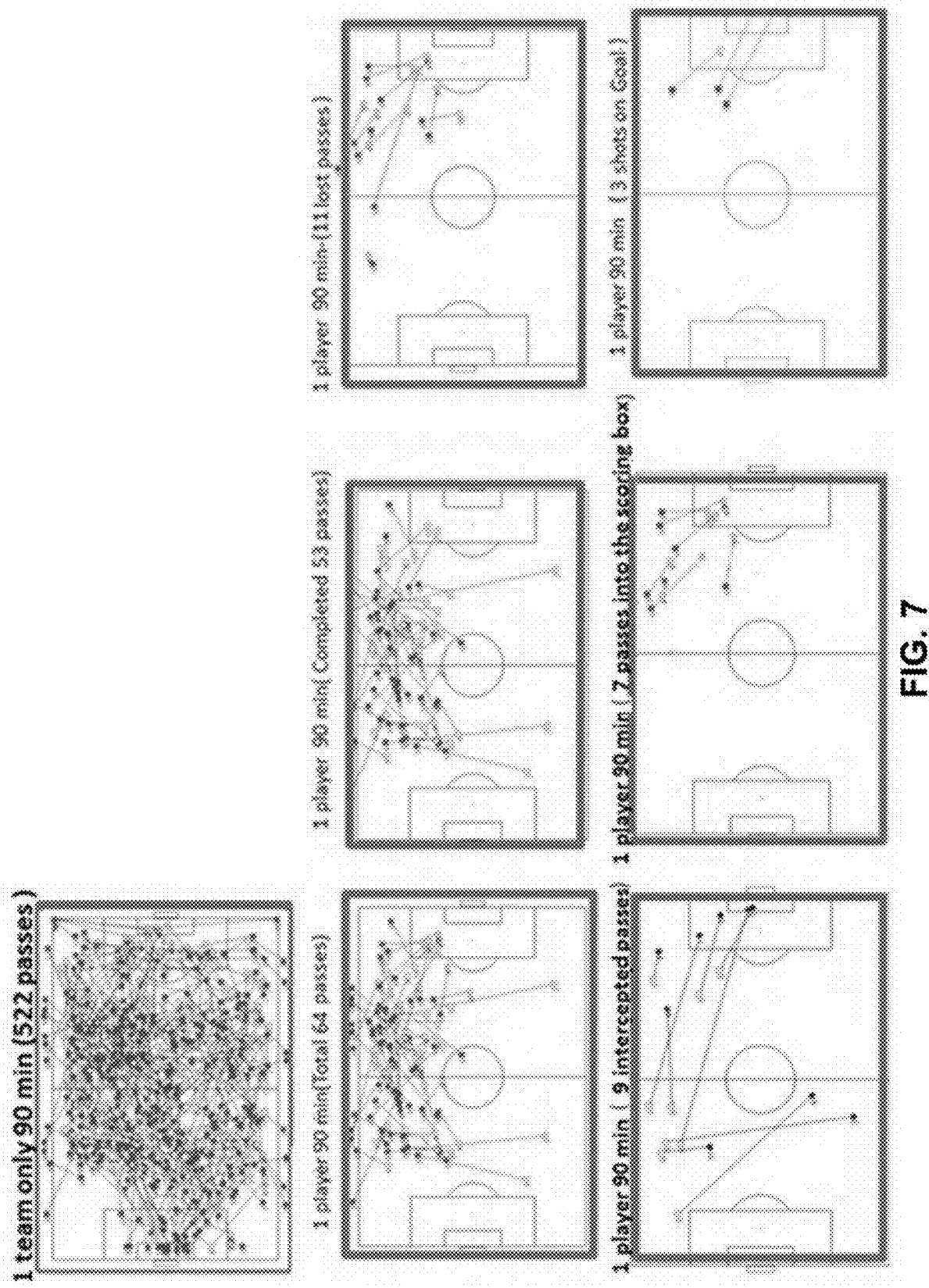
FIG. 7 illustrates examples of different data categories extracted from the data shown in FIG. 6E, in accordance with the described embodiments.

In FIG. 7, the data collected for the entire 90-minute game is further broken down. The top diagram in FIG. 7 shows all the passes for all players for a single team for the duration of the 90-minute game. This diagram can be very clotted and, therefore, may not produce any specific items (or information) of interest. The remaining diagrams in FIG. 7 provide particular statistical categories for a single player, e.g., total passes by the player, number of completed passes, number of lost passes, number of intercepted passes, number of passes into the scoring box, and number of shots on goal.

Figure 8:
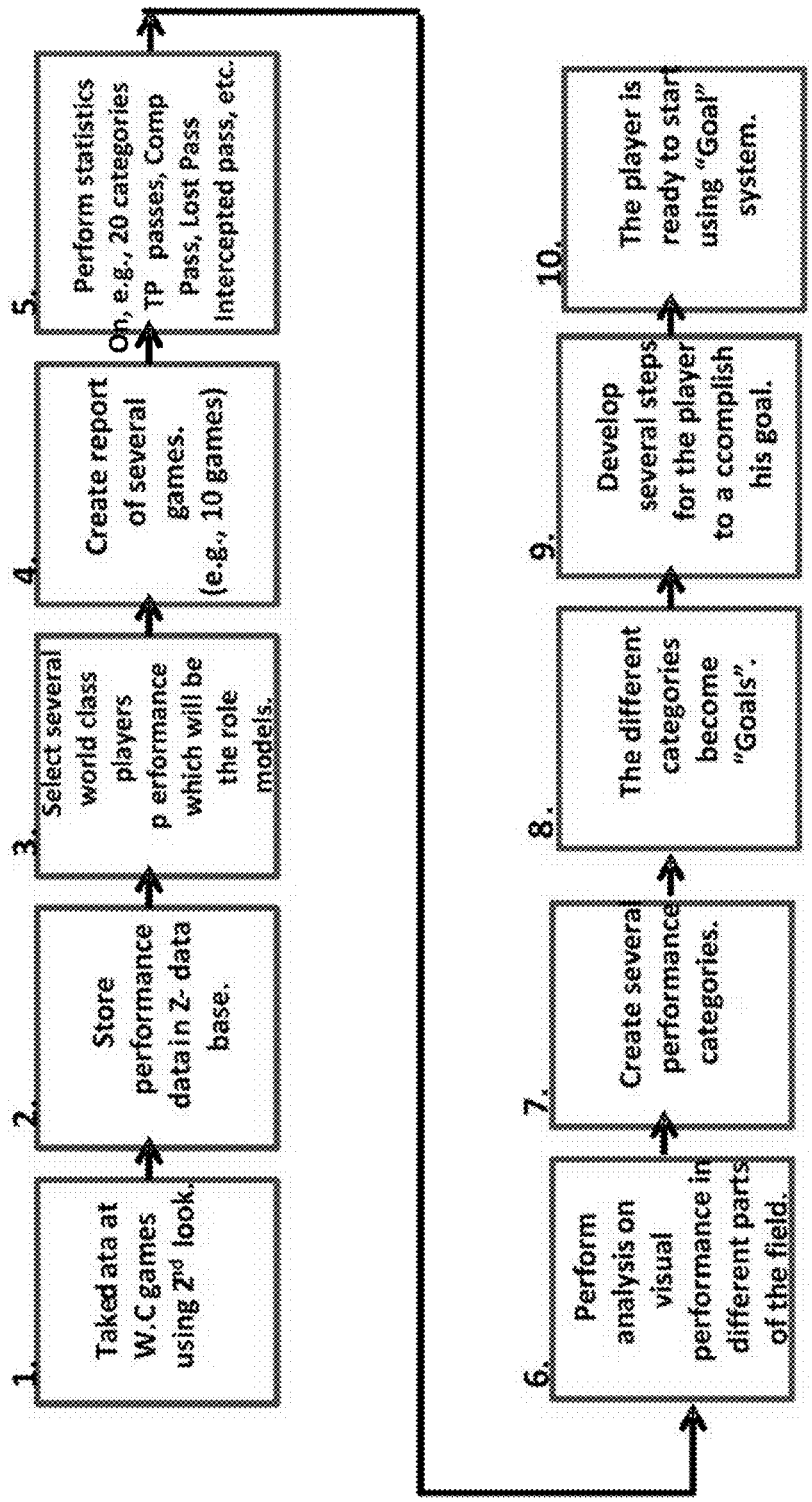
FIG. 8 illustrates a flowchart of an example method for the development of the DNA of soccer, in accordance with the described embodiments.

FIG. 8 illustrates a set of example steps that can be performed as part of quantifying or describing the DNA of soccer, in accordance with example embodiments. As shown therein, these steps include data collection (steps 1-2), data compilation and processing (steps 3-5), data presentation (step 6), and goal setting (steps 7-9), which allows a player to start using the "goal" system (step 10).

Figure 9:
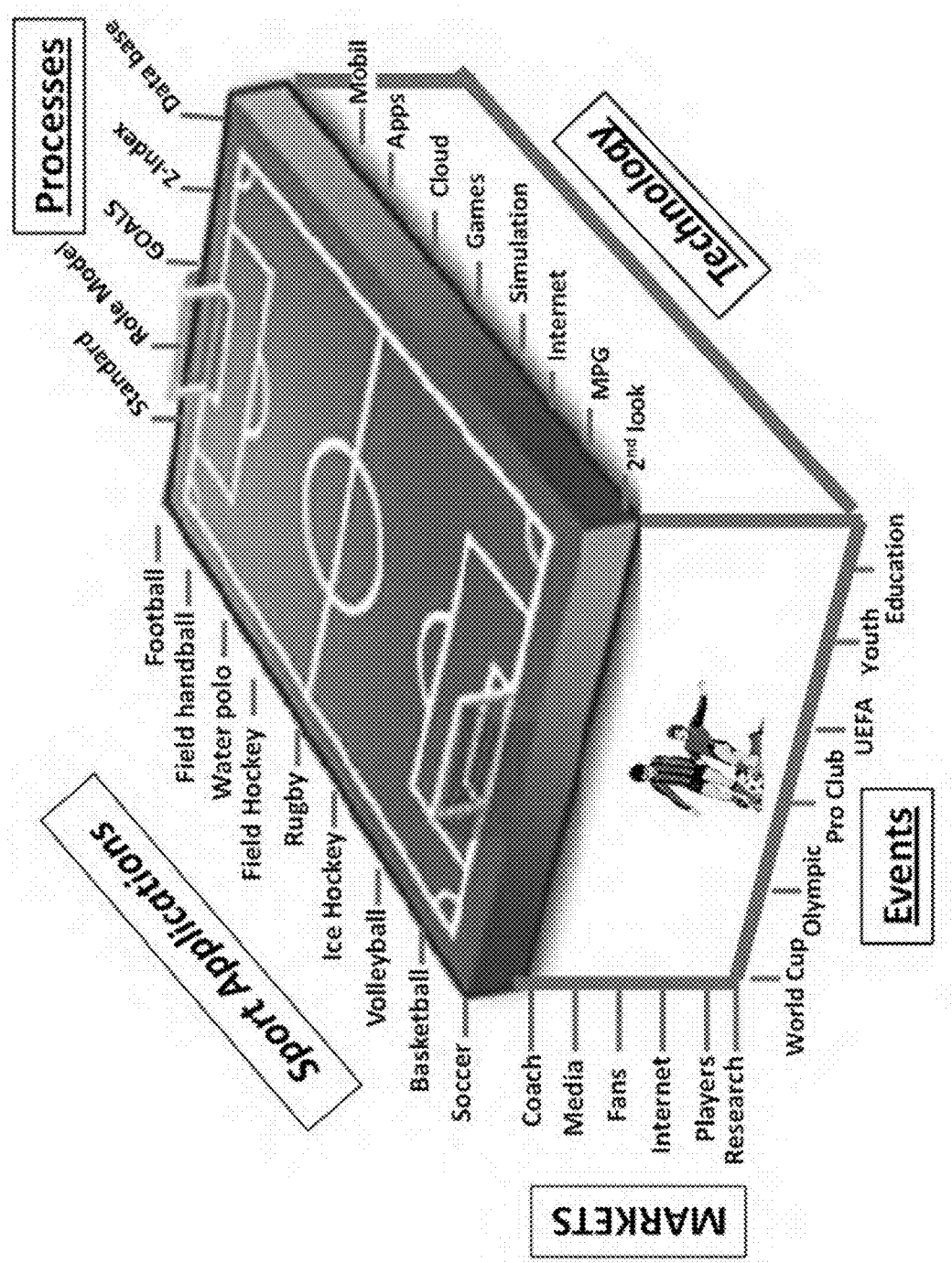
FIG. 9 illustrates an example of the different facets of the described embodiments.
Figure 10:
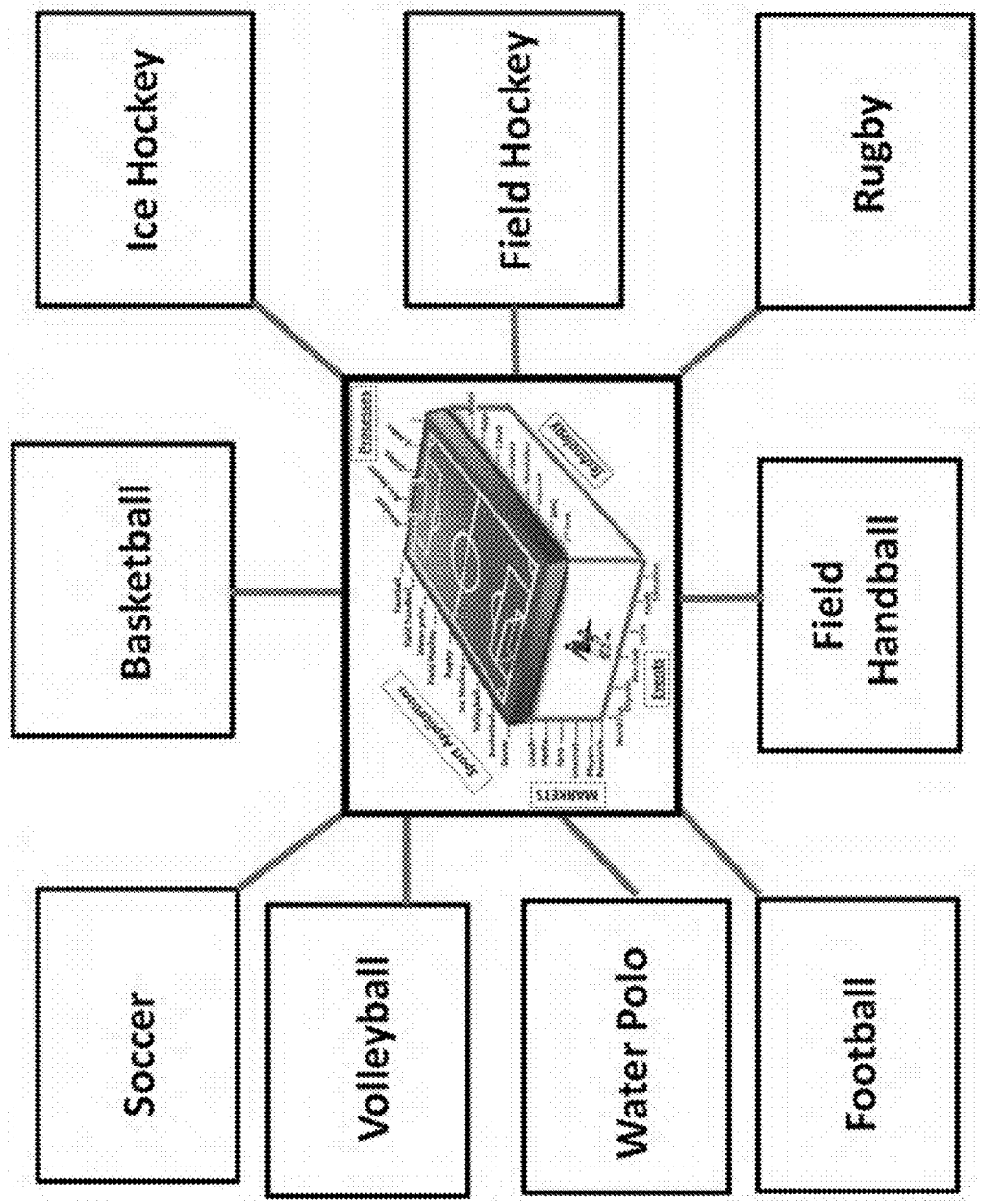
FIGS. 10-14 illustrate examples of the various applications, technologies, and markets that may be used in conjunction with the described embodiments.
Figure 11:
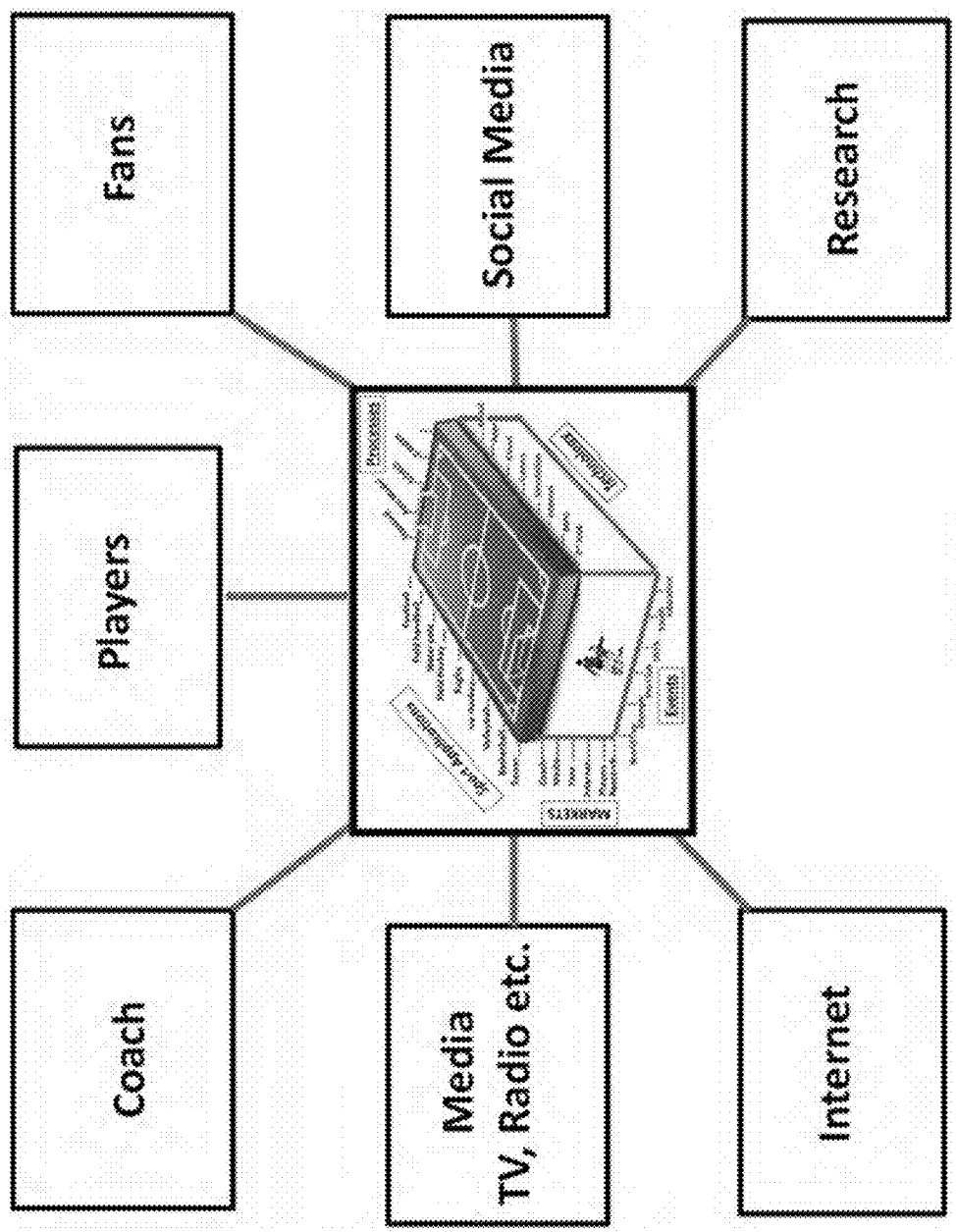
Figure 12:
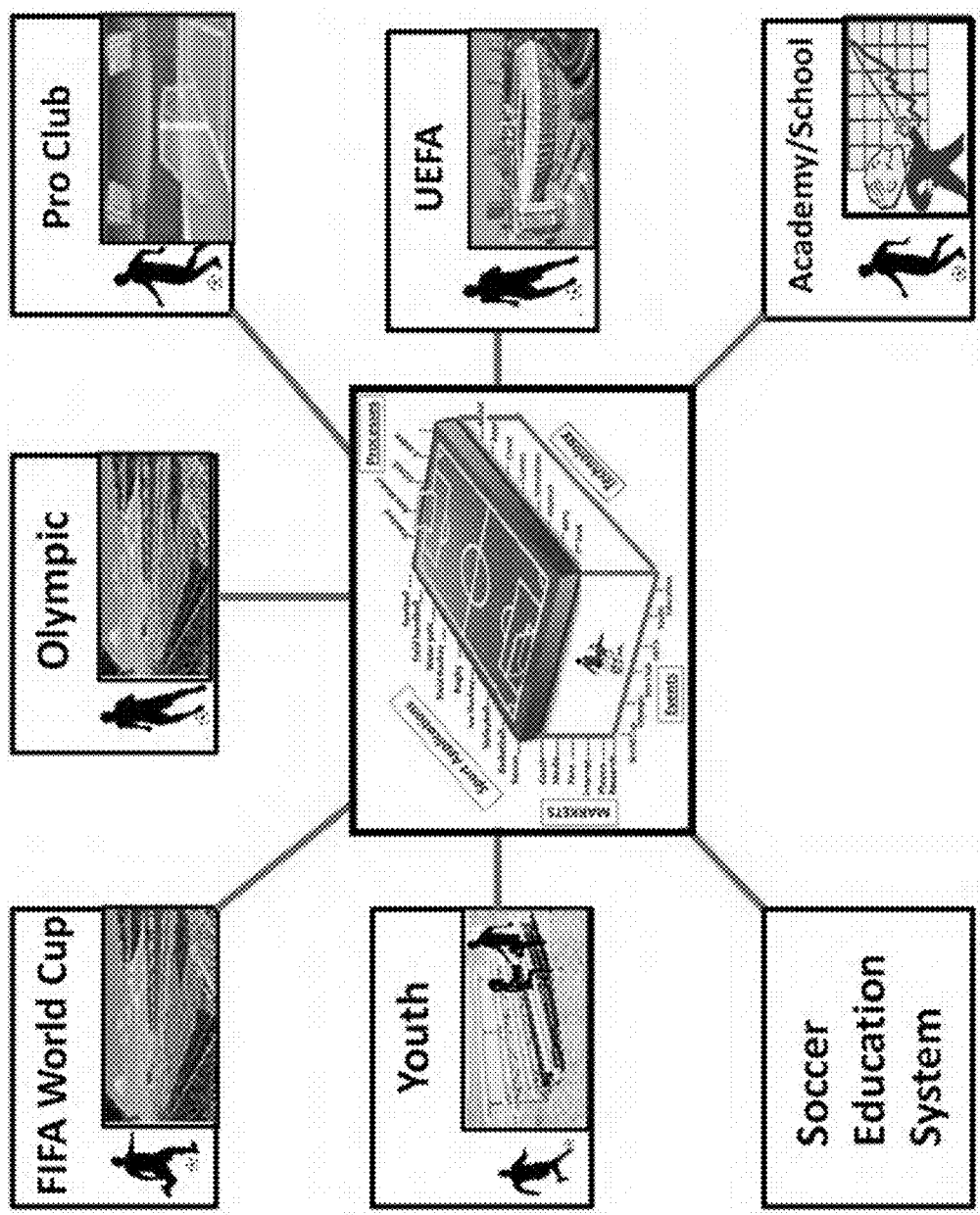
Figure 13:
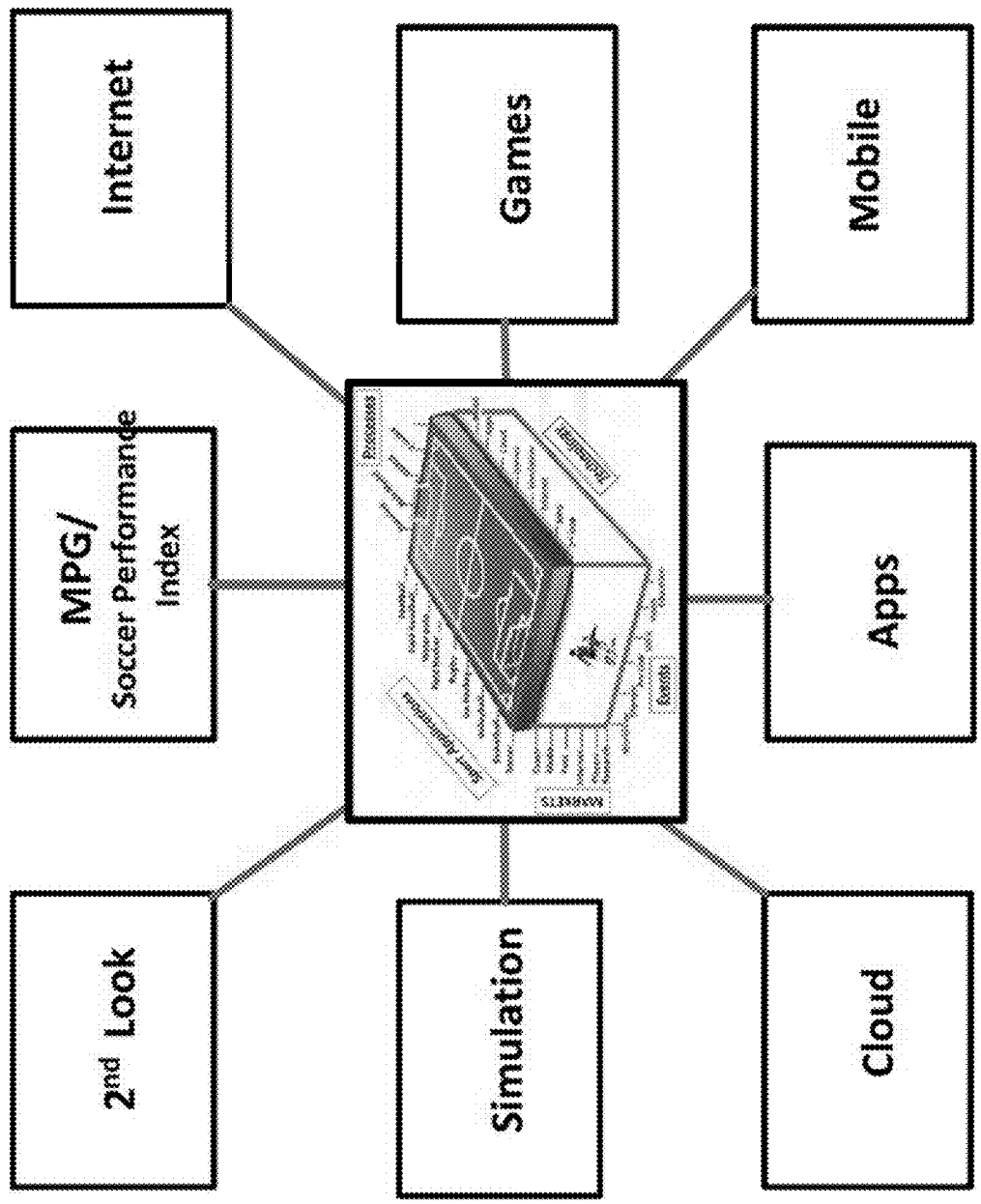
Figure 14:
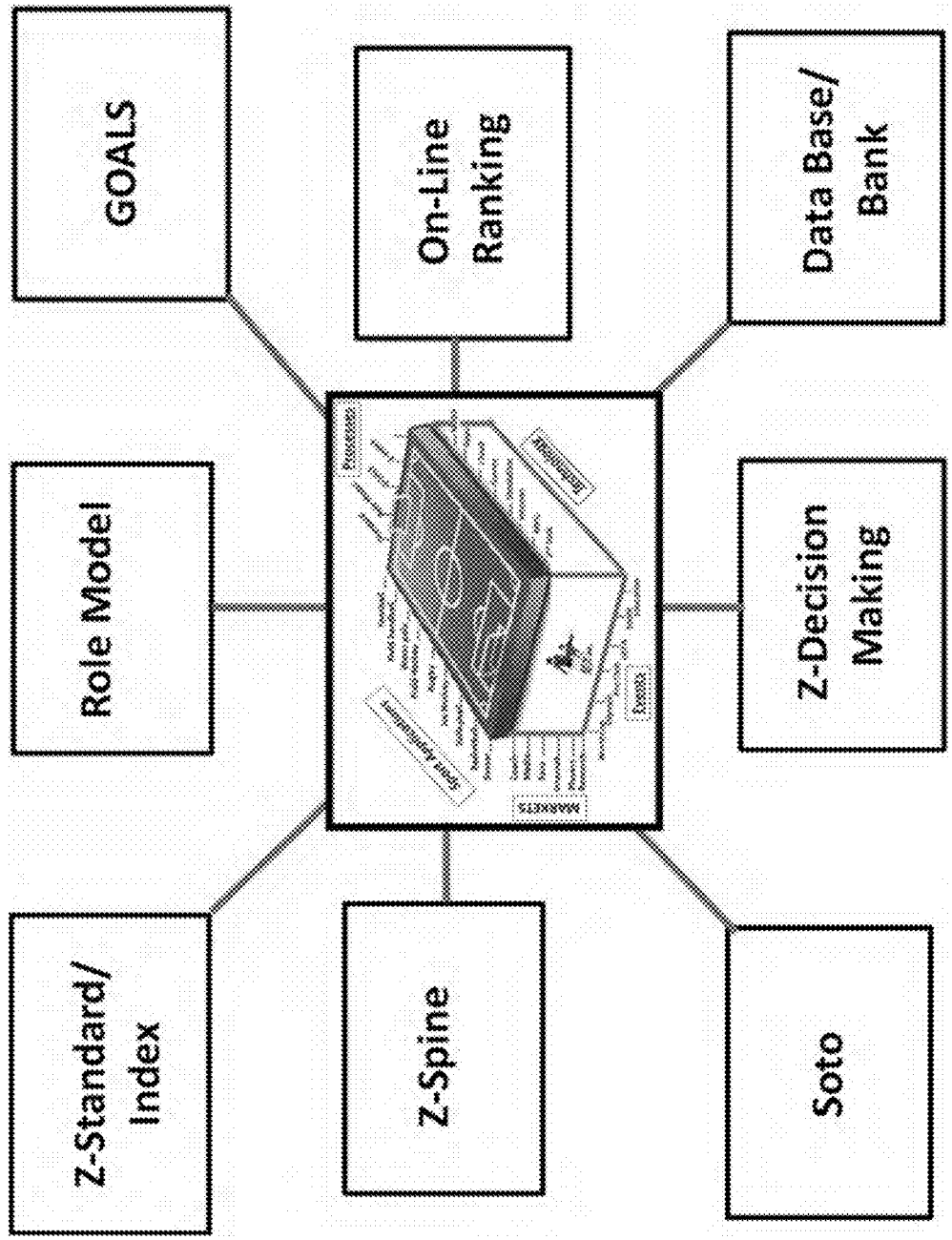

FIG. 9 is an overview of various sports applications, markets, events, technologies, and processes that can be benefit from and can be used in conjunction with the disclosed embodiments, as well as the various technologies of the disclosed embodiments. FIGS. 10, 11, and 12, illustrate, in more detail, an example list of applications, markets, and events, respectively, that can benefit from implementing the described embodiments. FIG. 13 is an example listing of technologies that can be used in, or developed based on, the described embodiments. FIG. 14 illustrates an example list of processes that can be developed and/or used based on the described embodiments. It should be noted that in this patent document the prefix Z (such as in "Z-Spine" in FIG. 14) represents a particular example of the entity or data that follows the prefix (e.g., a particular Spine).

Referring back to FIG. 1, in step 5, a Role Model is selected. When a player comes to a new team, he/she needs to understand the team's system of play. This will help him/her and the coach to select the best position suited for the player (e.g., goalkeeper, defender, midfielder, forward, etc.). Once a player's position is selected, he/she can select a Role Model so that the player can emulate the Role Model's performance on the field. This will be his job on the field during the game.

Selecting a Role Model for a player has an impact on the education and development of young soccer players since it is clear that there is no personal criticism in this kind of visual (graphic) and statistical review and comparison. This objective form of critique makes the point without undermining communication between the players and the coach. For many young players, this is important for building confidence. The real value of a Role Model is that it can give performance accountability that can challenge a player to set goals and improve a good teaching tool for both the player and the coach. With one glance, they can see visual trends and tendencies, as well as statistical performances. It will give the player the opportunity to emulate a star player as his/her role model.

Figure 15:
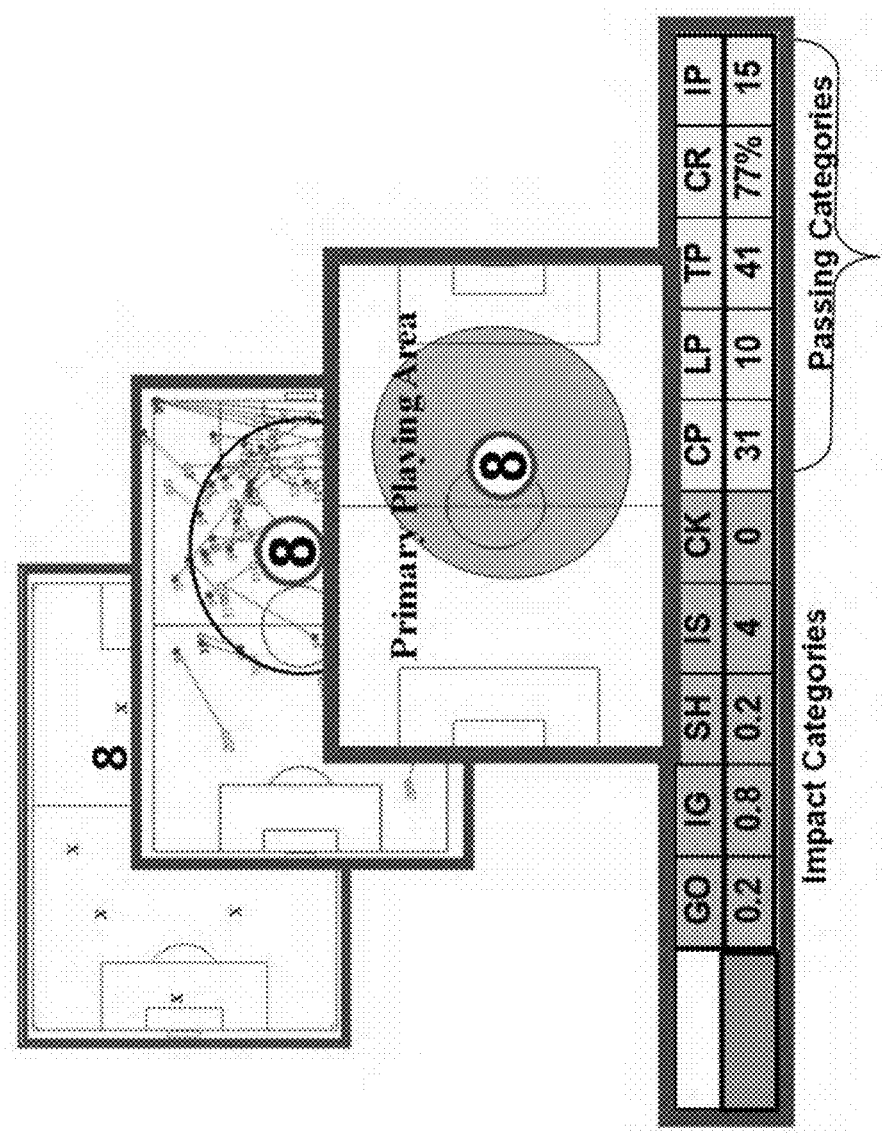
FIG. 15 illustrates an example of a screenshot of impact categories and passing categories, in accordance with the described embodiments.

FIG. 15 provides a screenshot of some of the impact categories and passing categories that are produced in accordance with an example embodiment. In particular, GO represents number of goals scored, IG represents number of impact goals (number of passes resulting in a goal), SH represents number of shots on goal, CK represents number of corner kicks, CP represents number of passes completed to teammates, LP represents number of lost passes, TP represents number of total passes, CR represents percentage of total passes that were completed, and IP represents the number of passes that were intercepted by the opponent.

Figure 16:
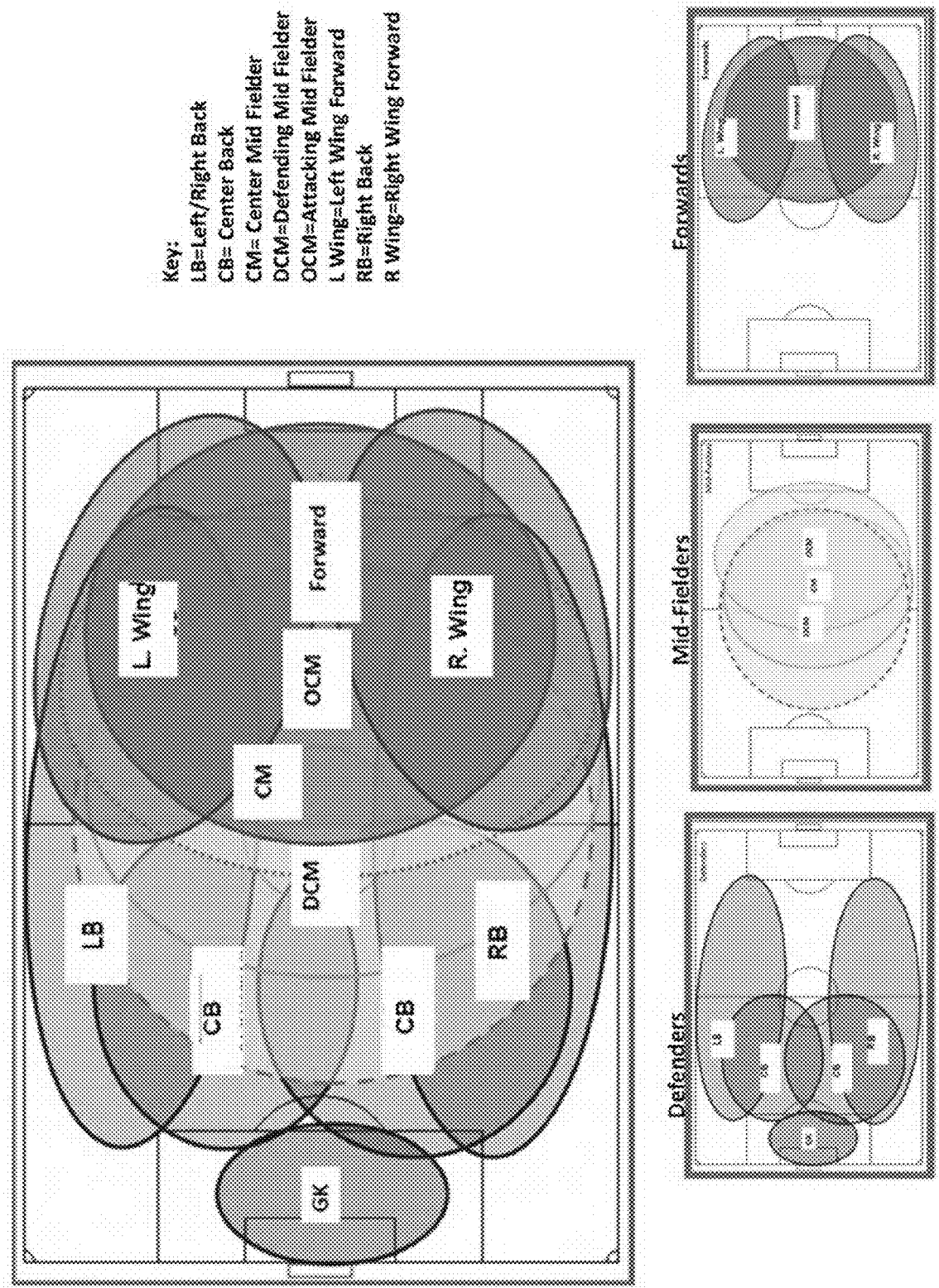
FIG. 16 illustrates an example diagram of a team's system of play, in accordance with the described embodiments.

FIG. 16 is a diagram illustrating an example of a team's system of play. As shown therein, the top section of FIG. 16 shows the position of all players' Role Models that are overlaid on top of the field for a 4:3:3 system of play. The bottom section of FIG. 16 shows the areas associated with Role Models for the defenders, midfielders, and forwards, respectively.

Figure 17:
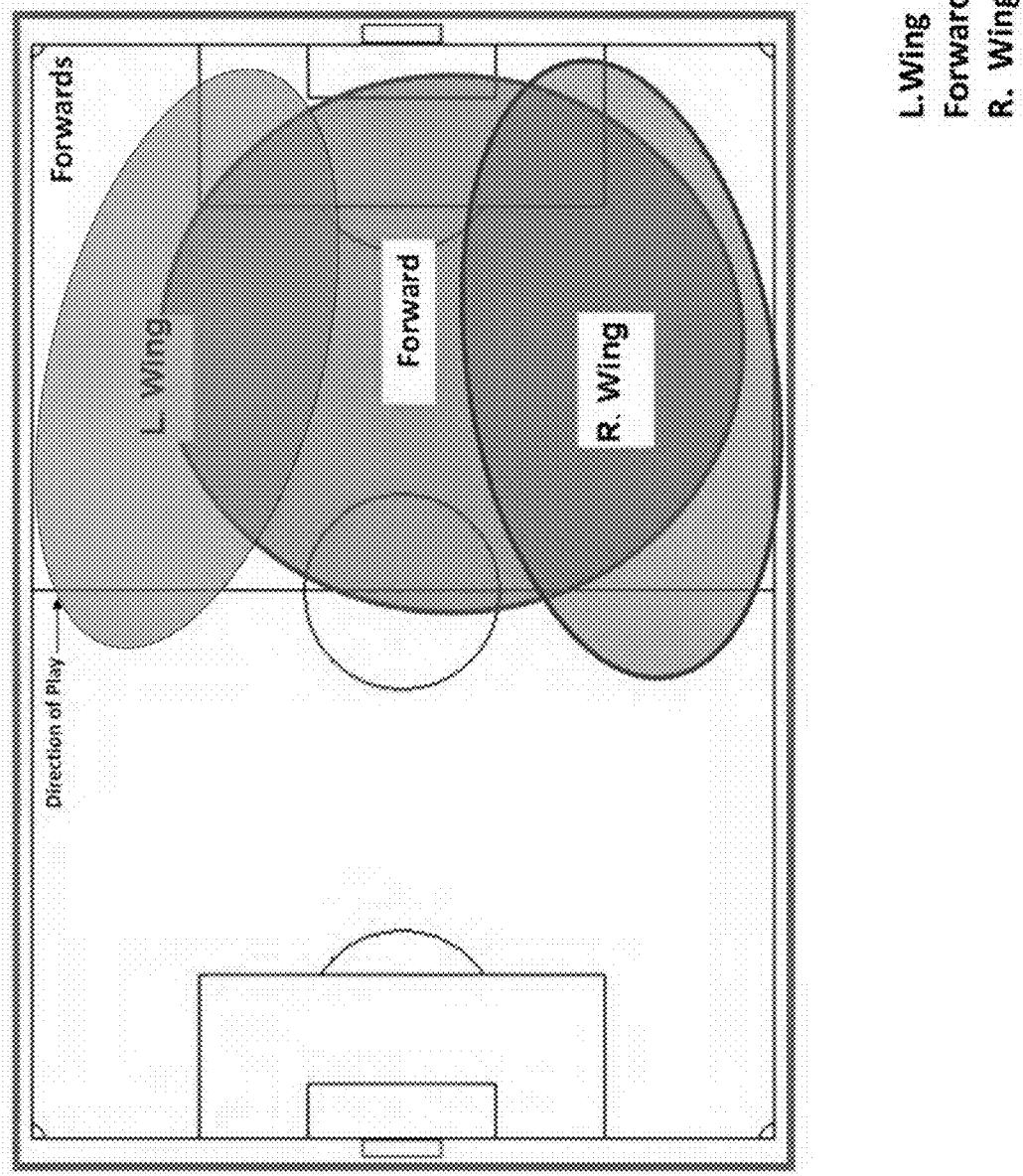
FIGS. 17-18 illustrate example diagrams of forward Role Model position(s), in accordance with the described embodiments.
Figure 18:
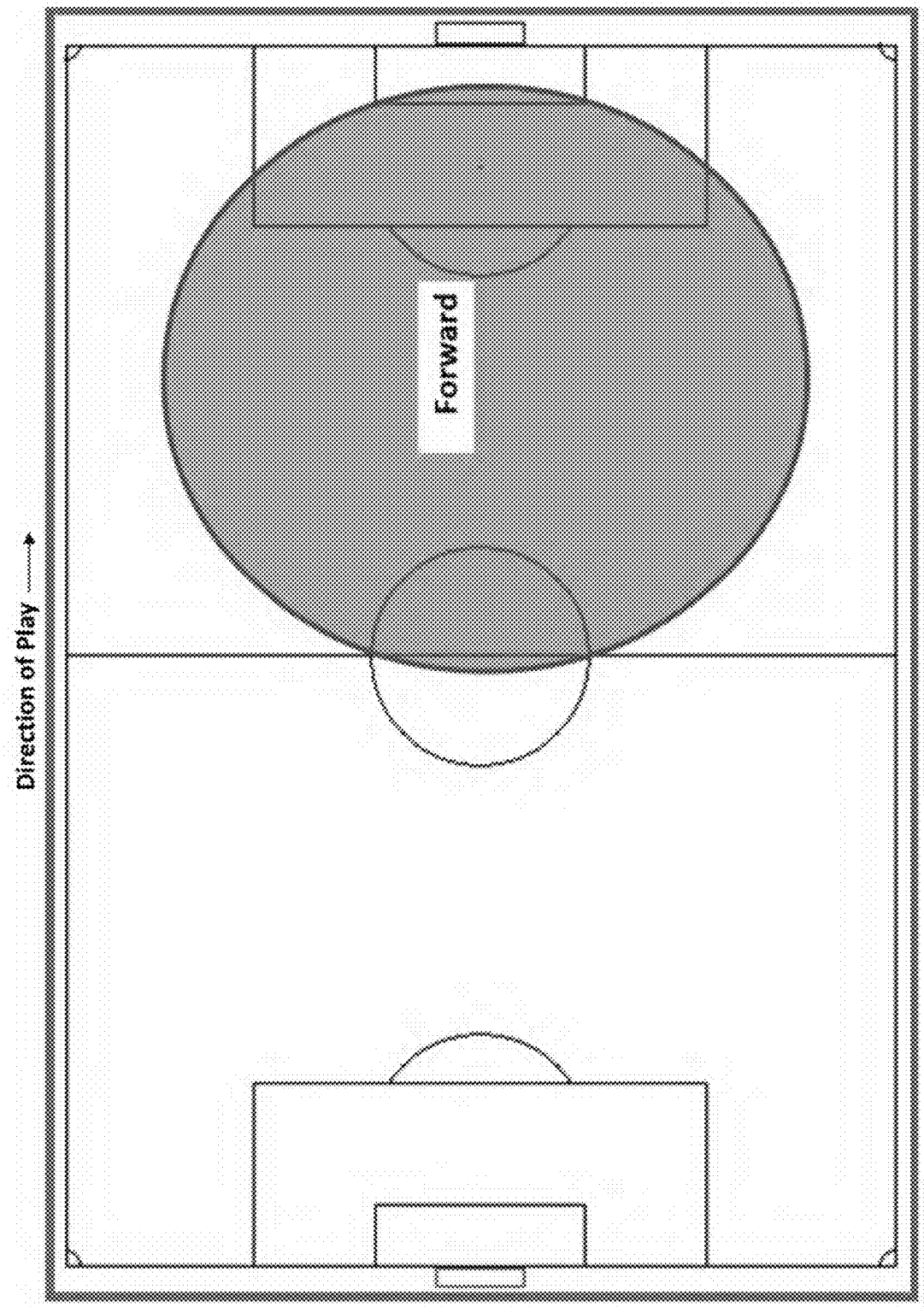
Figure 19:
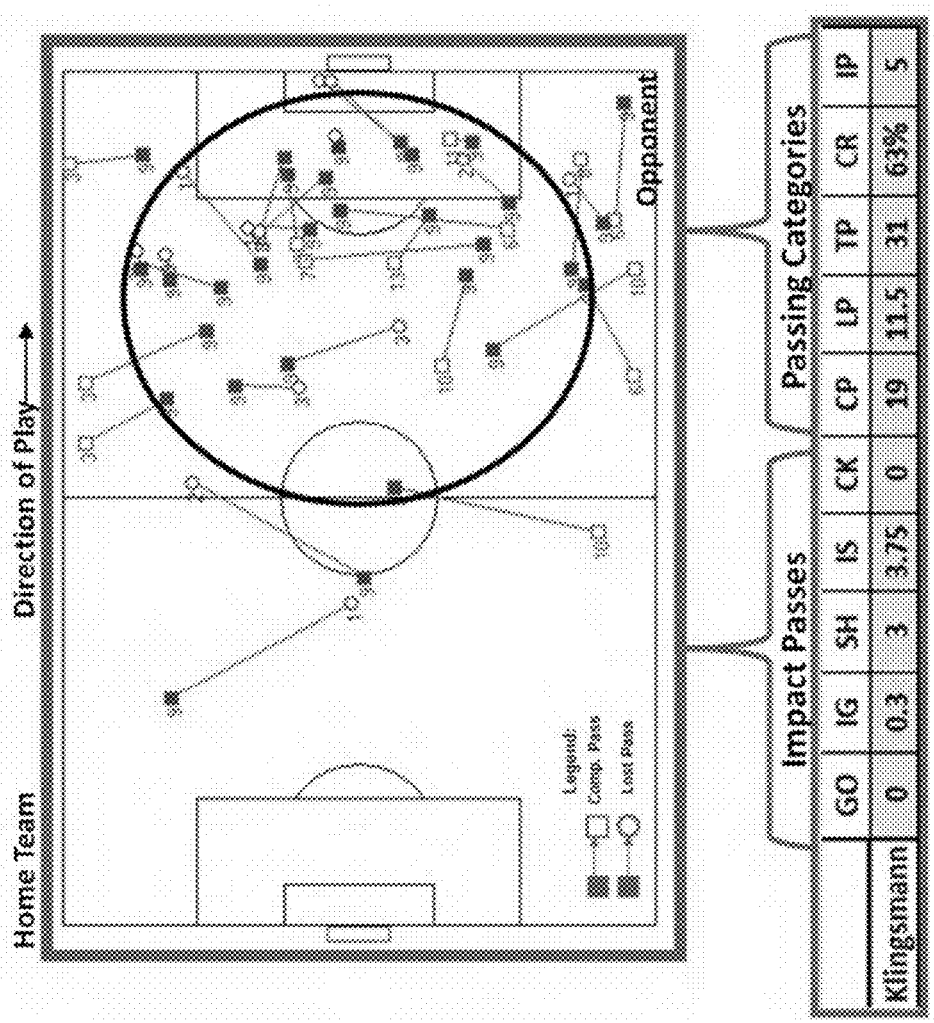
FIG. 19 illustrates example job performance categories for the forward Role Model position, in accordance with the described embodiments.

FIG. 17 illustrates an example of positioning for all three forward Role Model positions. FIG. 18 illustrates the positioning of one forward Role Model position (e.g., center forward) that is selected as a goal, and FIG. 19 illustrates the job performance categories for the selected Role Model forward (e.g., Klingsmann). As shown in FIG. 19, the visual diagram of passes that is superimposed on the field, the table below the diagram illustrates an average performance by a forward player (e.g., Klingsmann). This Role Model performance is used by the coach and the player to set quantitative goals.

Figure 20:
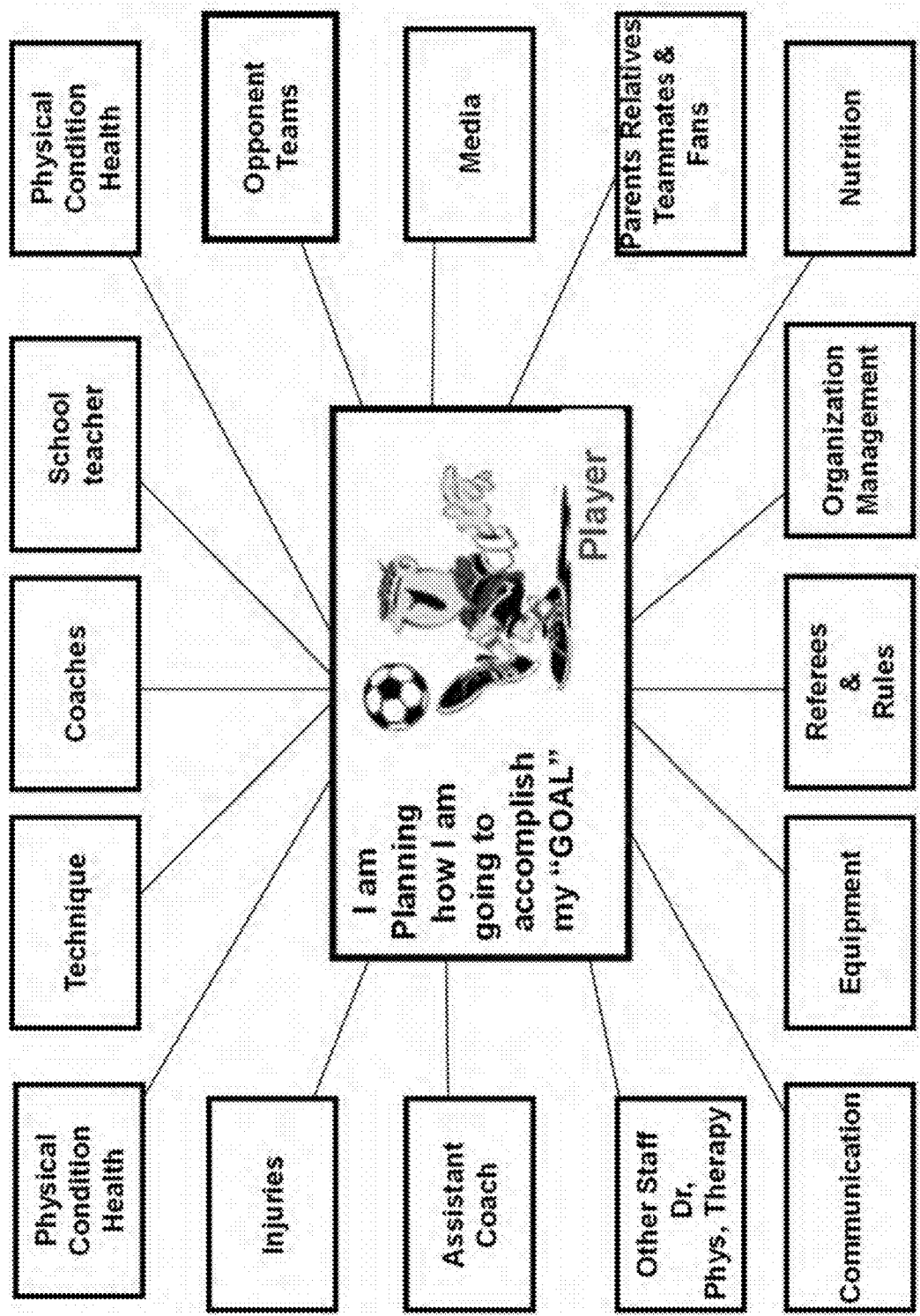
FIG. 20 illustrates examples of the different facets for skill improvement.

FIG. 20 is a diagram that illustrates an example of setting goals, and provides many of the elements, and the environment, that a young player will face on the road to success in soccer or other spots. Almost every young soccer player has first heightened level of anxiety when he first comes to a new environment. This is when you are doing several actions without priority and direction. It creates uncontrolled activities. One objective of the described embodiments is to change this first heightened level of anxiety to a second lower level of anxiety by setting goals, and making a plan to accomplish these goals. As a result, while the player may still have anxiety, it is organized and focused. Setting goals is step 6 in FIG. 1.

Figure 21:
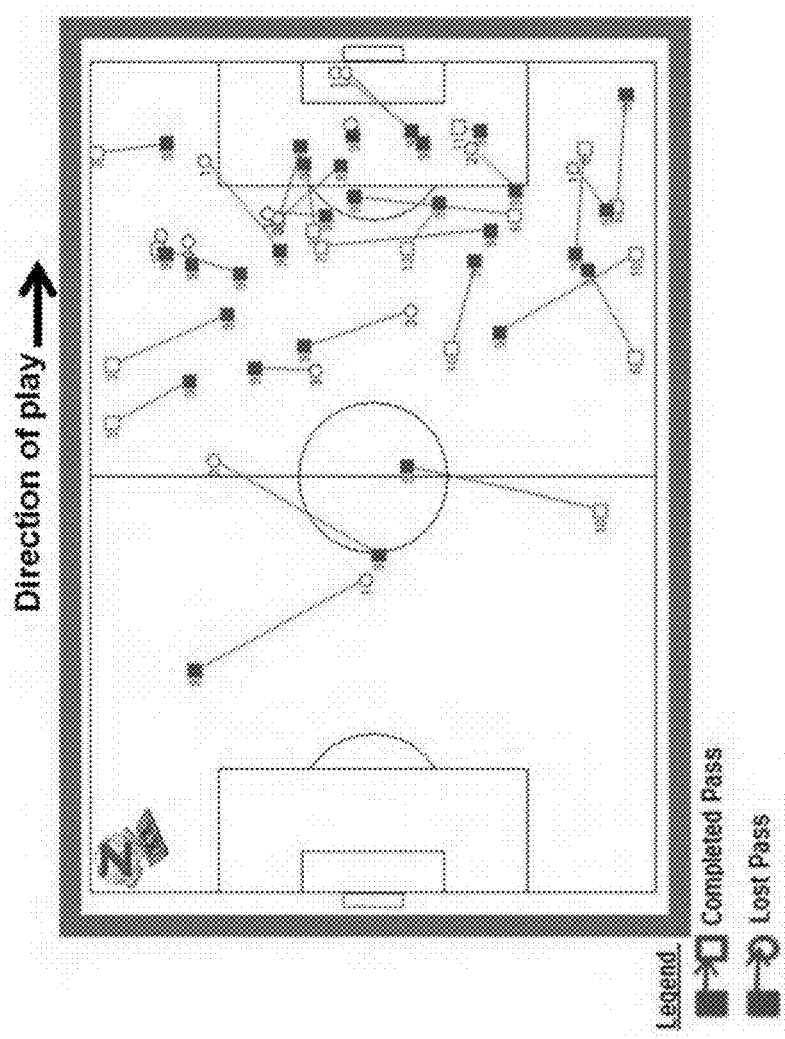
FIG. 21 illustrates an example of a model that provides goals for a player using the goal system, in accordance with the described embodiments.
Figure 22:
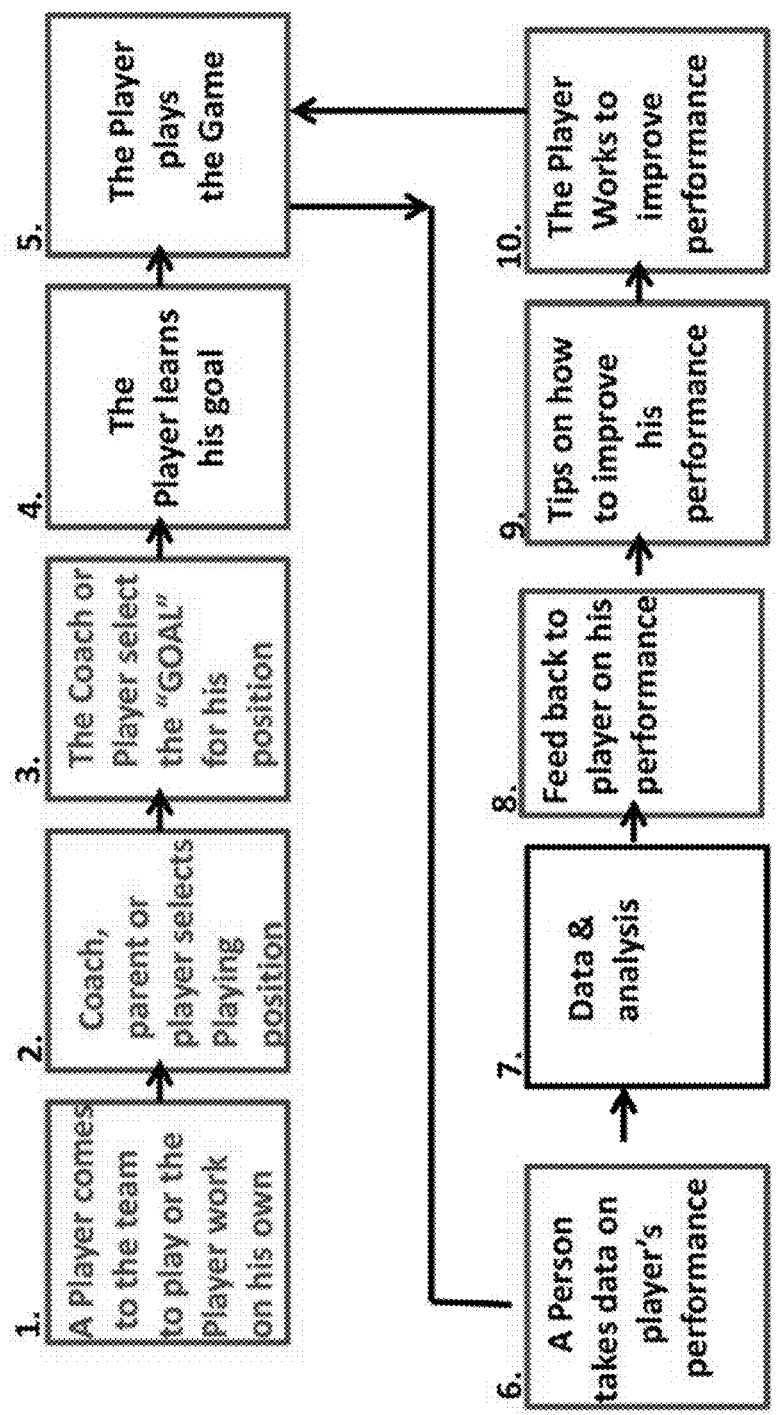
FIG. 22 illustrates a flowchart of an example method for using the goal system, in accordance with the described embodiments.
Figure 23:
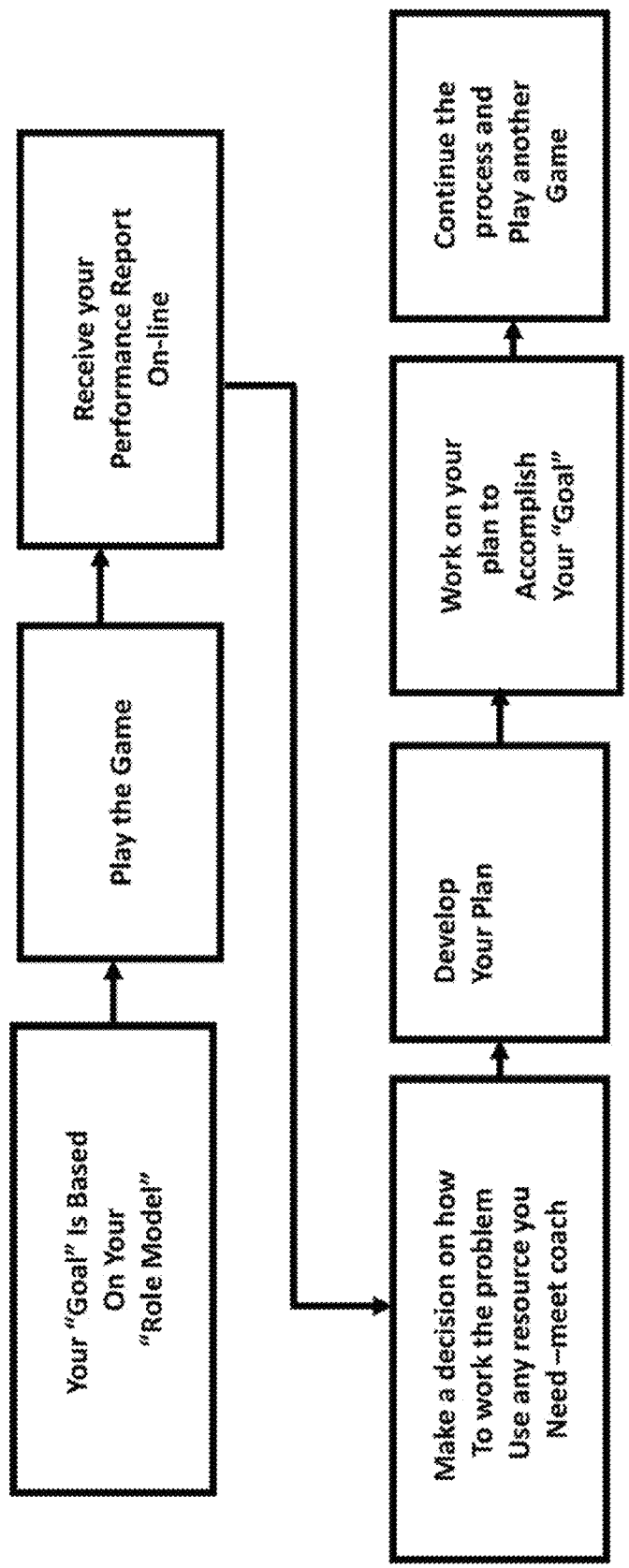
FIG. 23 illustrates a flowchart of another example method for using the goal system, in accordance with the described embodiments.

By the way of example and not by limitation, a "forward" position in soccer is selected to provide how goals are set, in accordance with the described embodiments. FIG. 21 illustrates a Role Model position that provides goals for the player. That is, the Role Model provides a "job description" for the player. FIG. 22 illustrates a set of example operations (or steps) that may be performed when a player is using the goal system for the first time. The operations of FIG. 22 can be repeated until the player achieves the set goals. FIG. 23 illustrates another set of operations that can be carried out when a player is using the goal system.

Example Embodiment for Implementing Goal Setting

Figure 24B:

In some embodiments, FIG. 24A provides a list of primary goals and supportive roles/jobs for a player in a forward position. These goals provide a limited set of roles and responsibilities that the player is striving to fulfill. FIG. 24B provides a diagrammatic view of the goals that are listed in FIG. 24A. A more detailed description of a set of example goals for a player in the forward position are as follows:

Goal 1 is to learn to cover primary playing area (PPA). PPA is the area where the player is touching the ball most of the time when he is playing on the field. In an example, the player's first goal is to learn to move inside his PPA and learn to touch the ball a predetermined number of times (e.g., 24 times). The purpose of Goal 1 is to educate the player of his PPA where he is performing his job (such as passing, receiving, tackling, intercepting the ball, etc.) Another purpose of Goal 1 is to help the player increase his mobility inside his PPA. The goal for the player is to perform his job in the area that he is responsible for in a similar fashion as his Role Model. The Role Model performance for this goal can be, for example, Jurgen Klinsmann ("J. K."), a forward player, who played for the German national team and other top professional teams.

Figure 25:
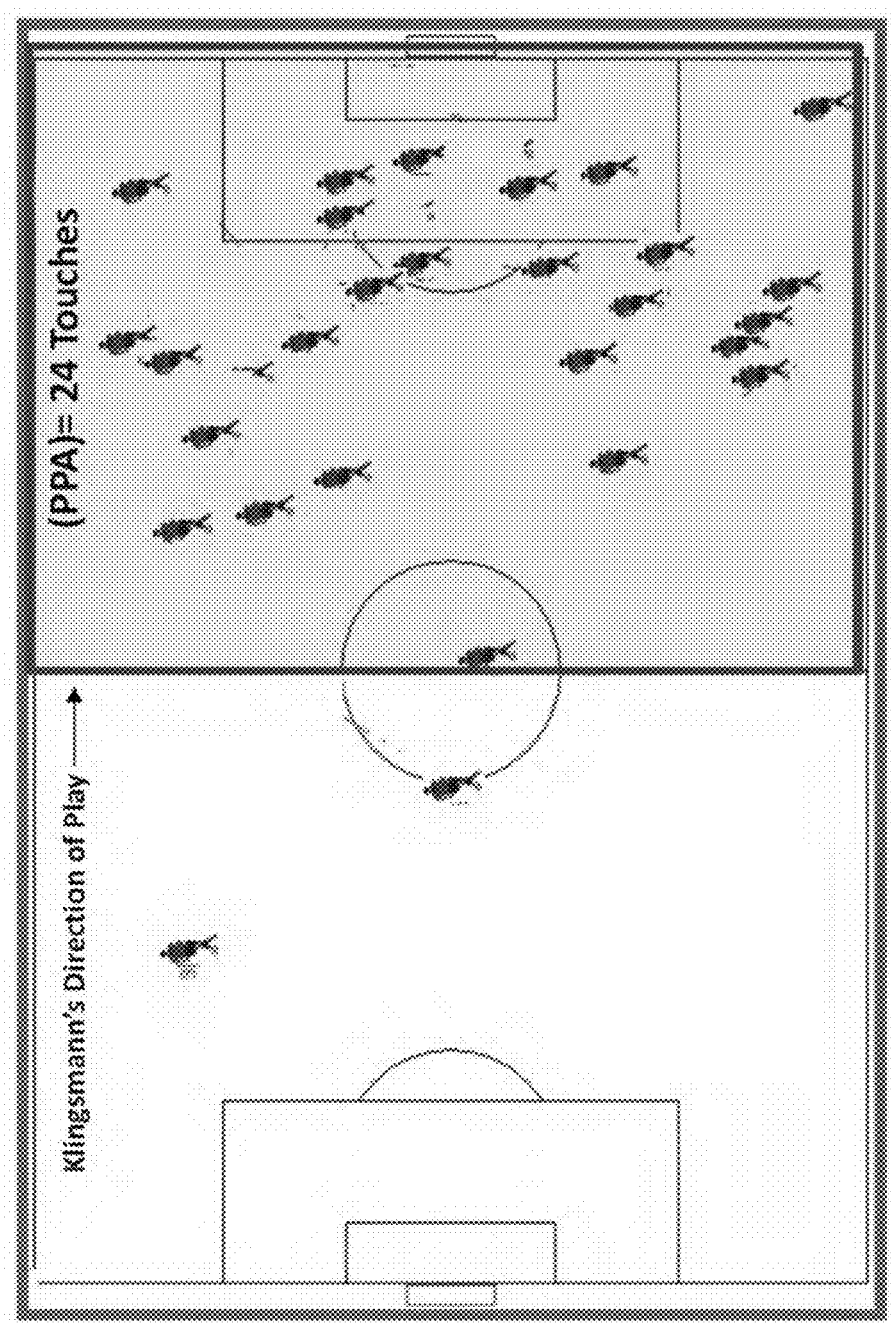
FIGS. 25-56 illustrate examples of diagrammatic views for the different goals shown in FIG. 24A, in accordance with the described embodiments.
Figure 26:
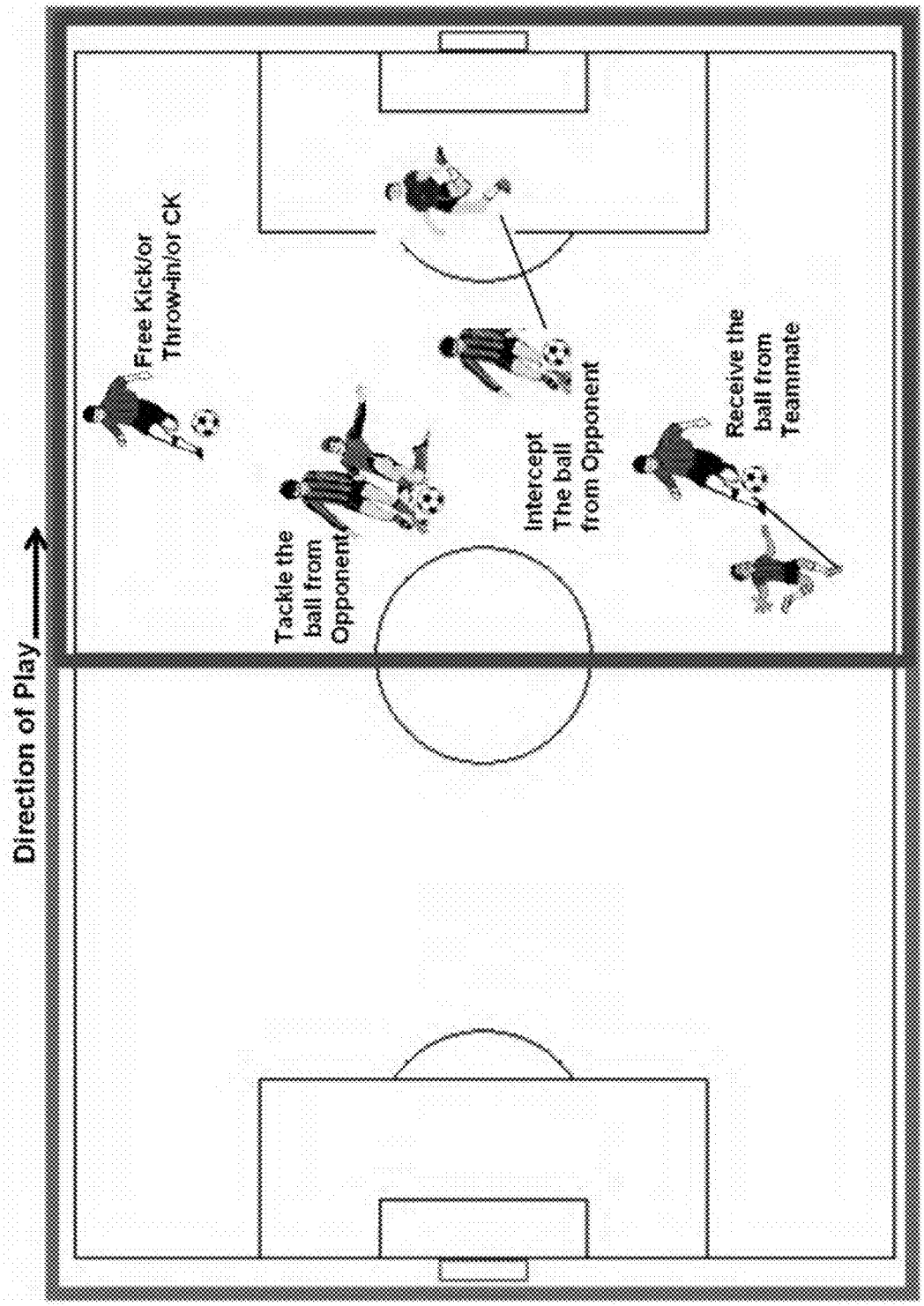

FIG. 25 illustrates an example of step 1 of Goal 1. As shown therein, the player's goal is to learn to move inside his PPA and to perform 24 touches with the ball inside this PPA similar to, his Role Model, J. K. In FIG. 25, the bordered area on the right-hand side of the field is the player's PPA. FIG. 26 further illustrates what it means for J. K. to touch the ball in his PPA, and shows the various player possibilities to touch the ball during the game. These possibilities include, but are not limited to, taking a free kick, a throw-in and/or a corner kick (CK), tackling the ball away from the opponent, intercepting the ball from the opponent, and receiving the ball from a teammate.

Figure 27:
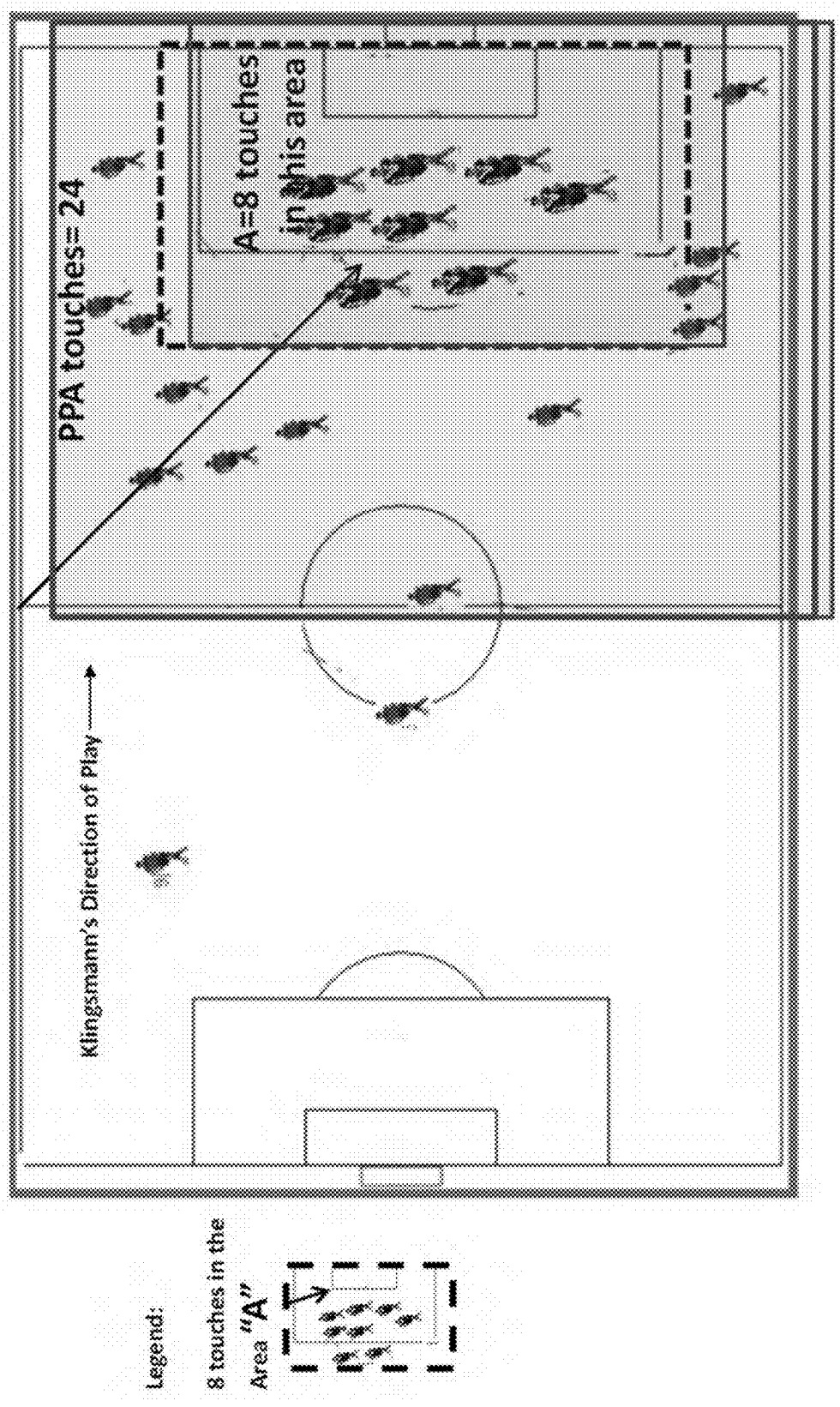

In step 2 of Goal 1, the player learns to focus more and perform at least 8 touches of the ball in area "A" (i.e., an area within the player's PPA) and still keep the total touches in the attacking half to be a minimum of 24 touches. Thus, in step 2 of Goal 1, the player's goal becomes to perform 8 of the 24 touches inside Area "A". FIG. 27 illustrates an example of step 2 of Goal 1 and area A.

Figure 28:
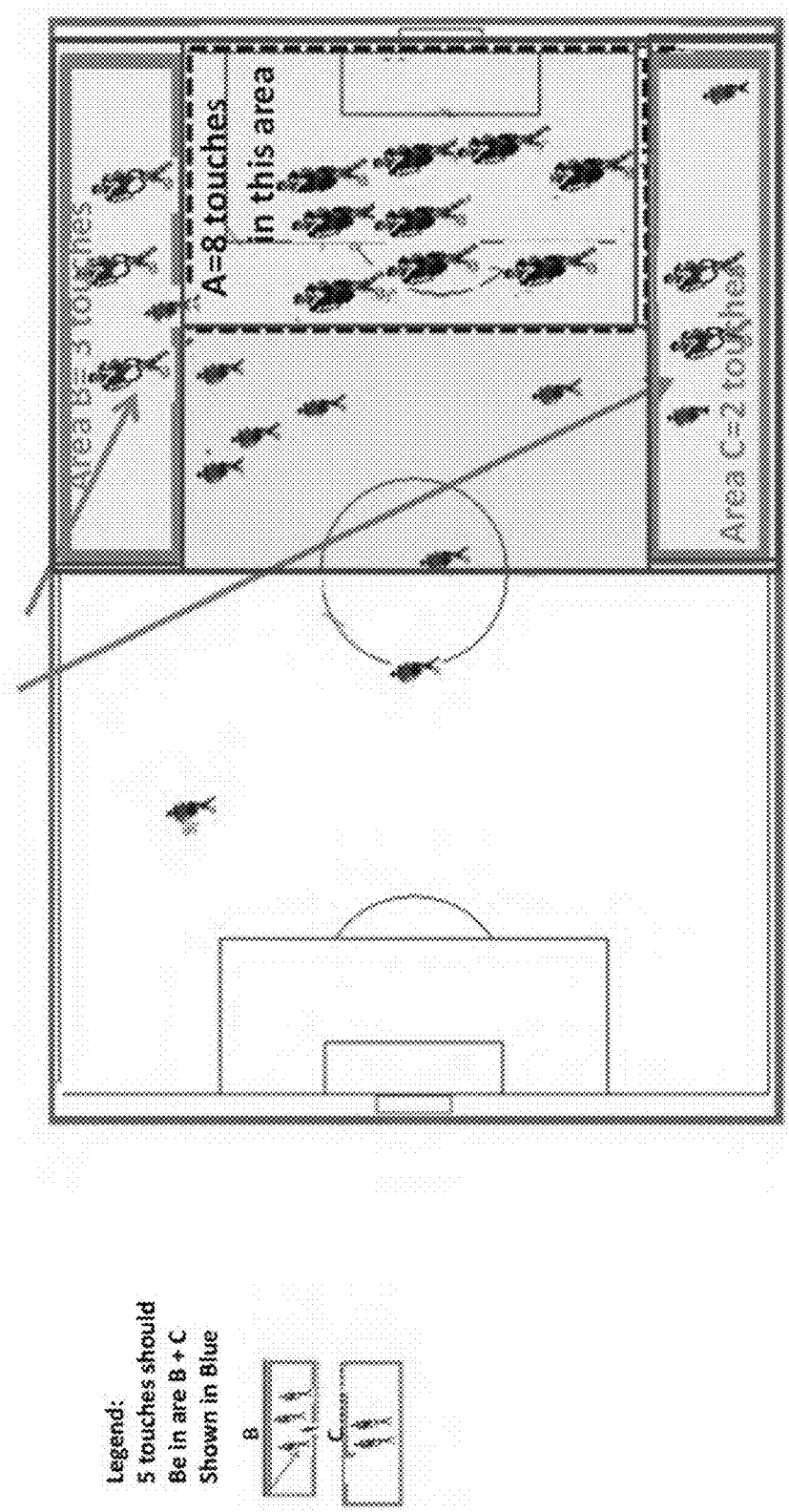

The learning goals of Goal 1 continue with step 3 as illustrated in FIG. 28. As shown therein, the player must perform 24 touches in his PPA, of which he must perform 8 of the 24 touches inside Area "A" and, additionally, must perform 5 (3+2 total touches) of the 24 touches inside areas "B" and "C". As such, in step 3, we are concentrating on expanding the job by focusing on area B and C in addition to the entire attacking half and area "A."

Figure 29:
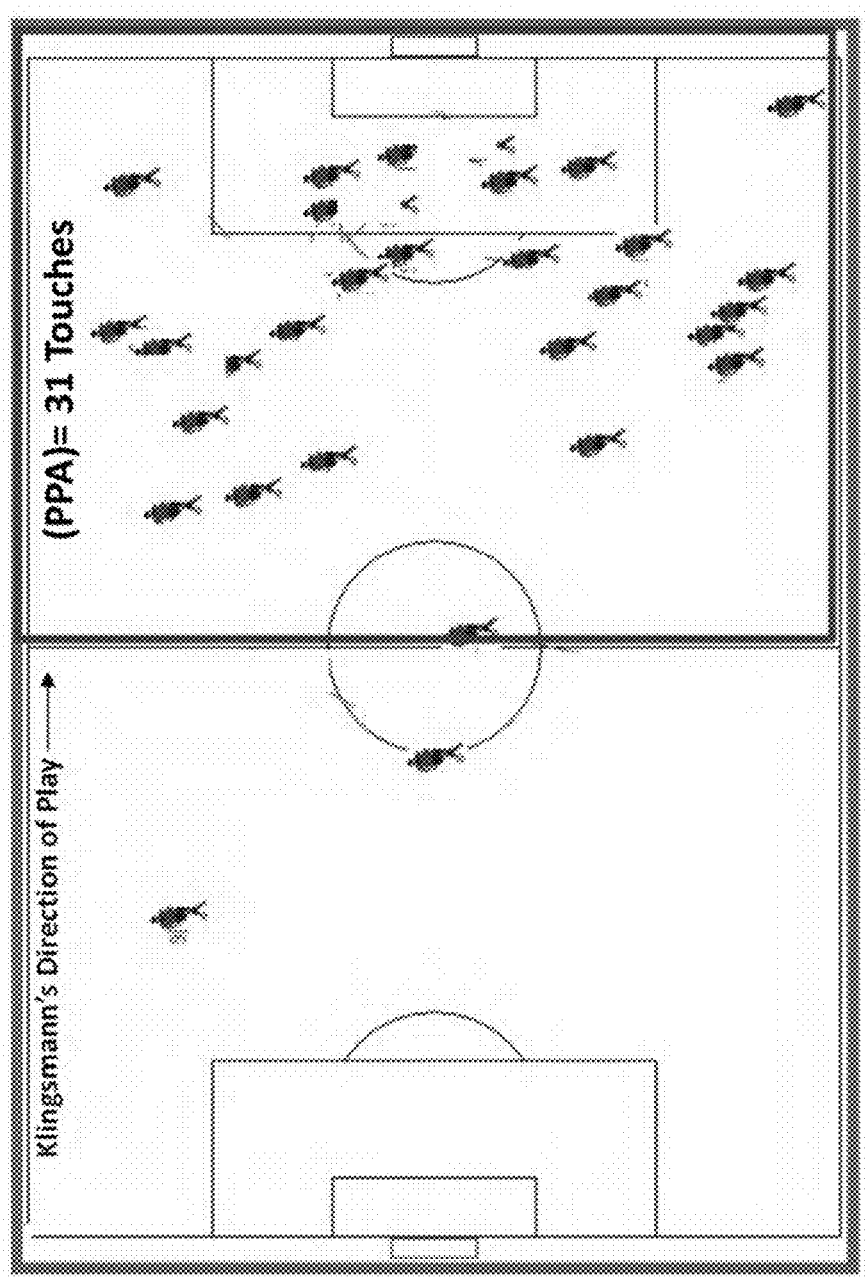

Goal 2 relates to an advanced PPA. In particular, the PPA becomes the area where the player is touching the ball most of the time (e.g., 31 touches) and the player needs to learn to move inside his PPA and touch the ball more in specific areas such as "A" and "B+C." The purpose of Goal 2 is to educate the player of his primary playing area and to help the player to increase his mobility inside his primary playing area. The report of Goal 2 will show the location of the player touching the ball on the field, e.g., as squares. Once again, the Role Model and "standard" performance for this goal can be selected to be J. K. FIG. 29 illustrates an example of step 1 of Goal 2, which is to perform 31 touches inside the PPA (e.g., the bordered rectangle on the right-hand side of the field) similar to those done by J. K.

Figure 30:
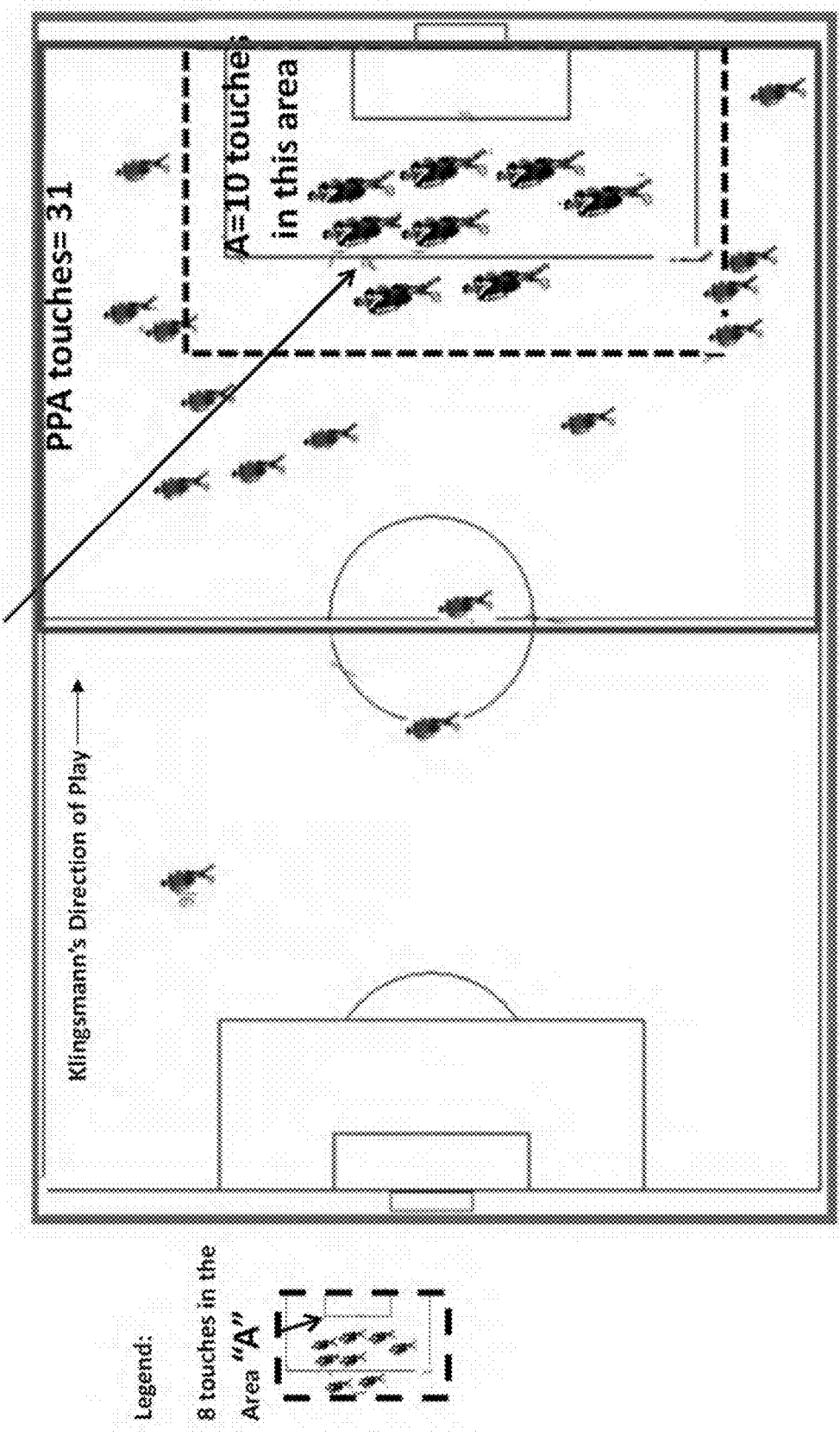
Figure 31:
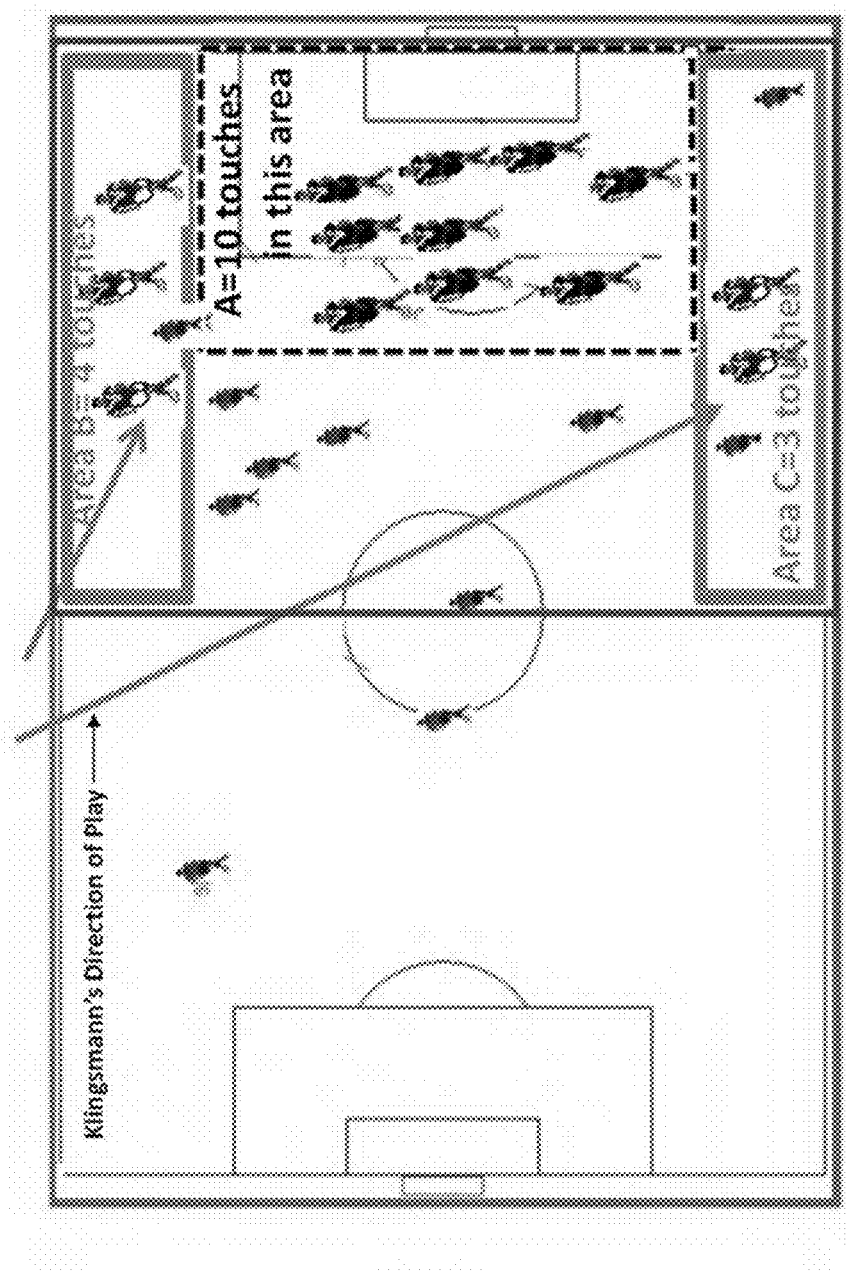

In step 2 of Goal 2, the player is learning to focus more and perform at least 10 touches of the ball in area "A" and still keep the total touches in the attacking half to a minimum of 31 touches, as illustrated in FIG. 30. In step 3 of Goal 2, as illustrated in FIG. 31, the player must perform 31 touches in the PPA, perform 10 of those 31 touches in area A and, additionally, perform 7 touches in areas B and C (e.g., 4 in area B and 3 in area C).

Figure 32A:
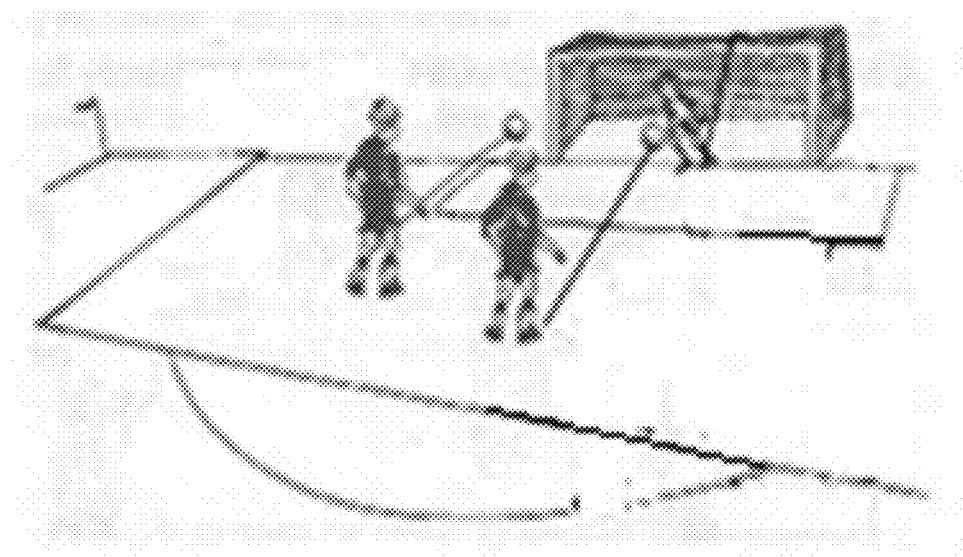
Figure 32B:
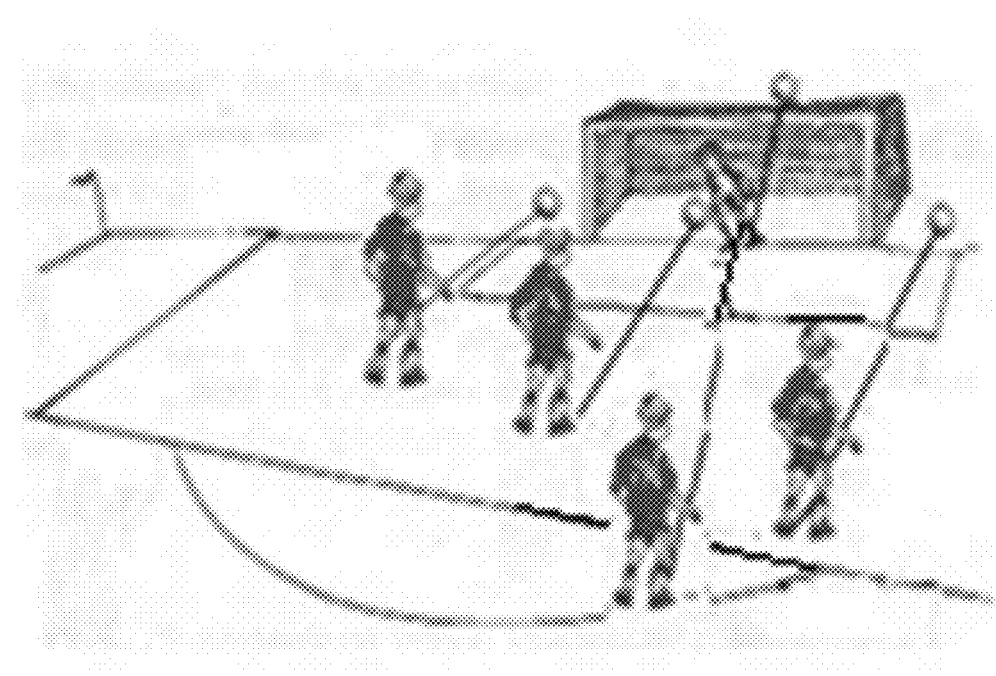

Goal 3 is to perform four shots towards the opponent goal. The purpose of this goal is to motivate and encourage the player to take shots on the goal. This is a preliminary step for the player to be able to perform his job of scoring a goal. In this example, the Role Model is J. K., and a shot is considered a shot on goal if it is initiated from anywhere on the field in the general direction of the opponent's goal. If a shot is initiated from a corner kick and ends inside the goal, it will be considered a shot. If a shot is initiated from a throw-in to the direction of the goal it will also be considered as a shot. Steps 2 and 3 of Goal 3 (illustrated in FIGS. 32A and 32B, respectively) are to perform at least two shots on goal and at least four shots on goal, respectively.

Figure 33A:
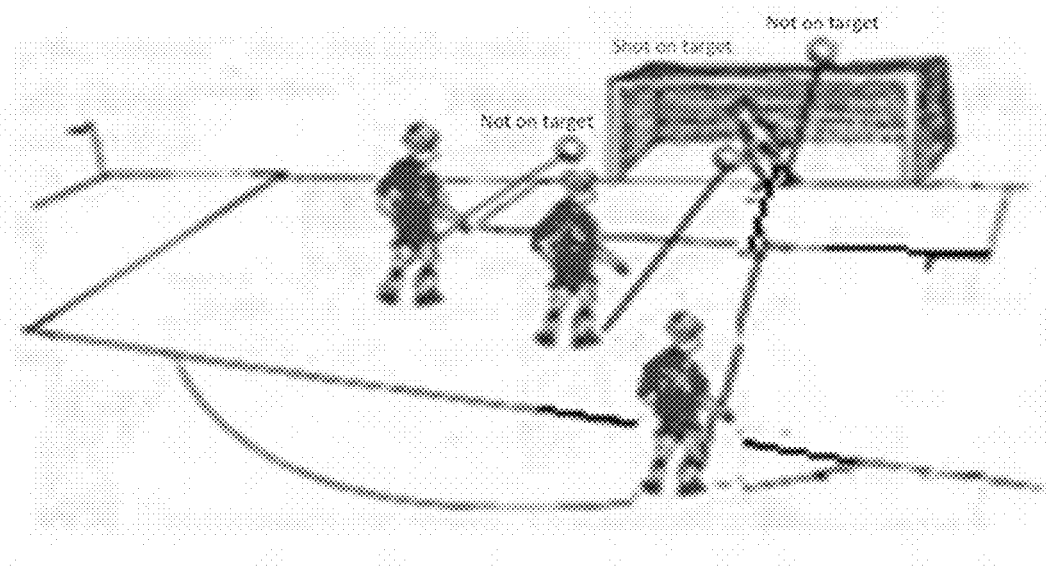
Figure 33B:
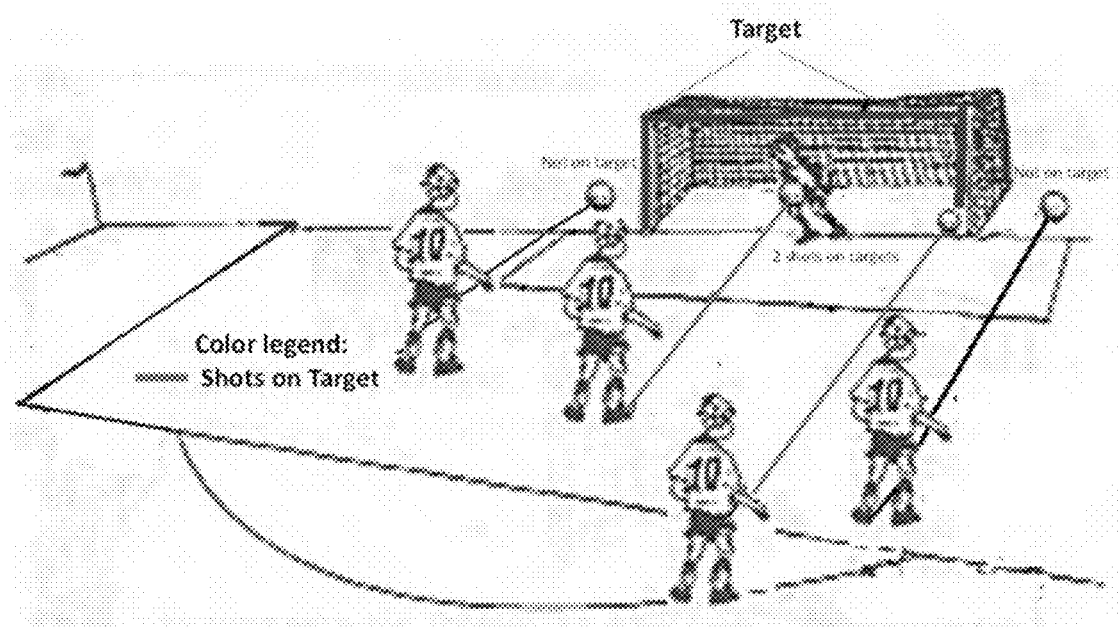

Goal 4 is to perform 2 shots on target, e.g., take a shot in the goal direction and in the direction of the frame of the goal. The purpose of this goal is to motivate and encourage the player to learn to be accurate when taking a shot, to measure the player performance, and to give him feedback on his accomplishment of his goal. Any shots on the frame or saved by the goalkeeper in the area is considered a shot on target. FIG. 33A illustrates step 1 of Goal 4, which is to perform at least one shot on target, and FIG. 33B illustrates step 2 of Goal 4, which is to perform at least two shots on target.

Goal 5 is to score 1 goal. The purpose of this goal is to motivate and encourage the player to score a goal, which is the ultimate prize in soccer, and to measure the player performance and give him feedback on his progress and accomplishment of his goal. In one example, the Goal 5 may be to score at least one goal in two games.

Figure 34:
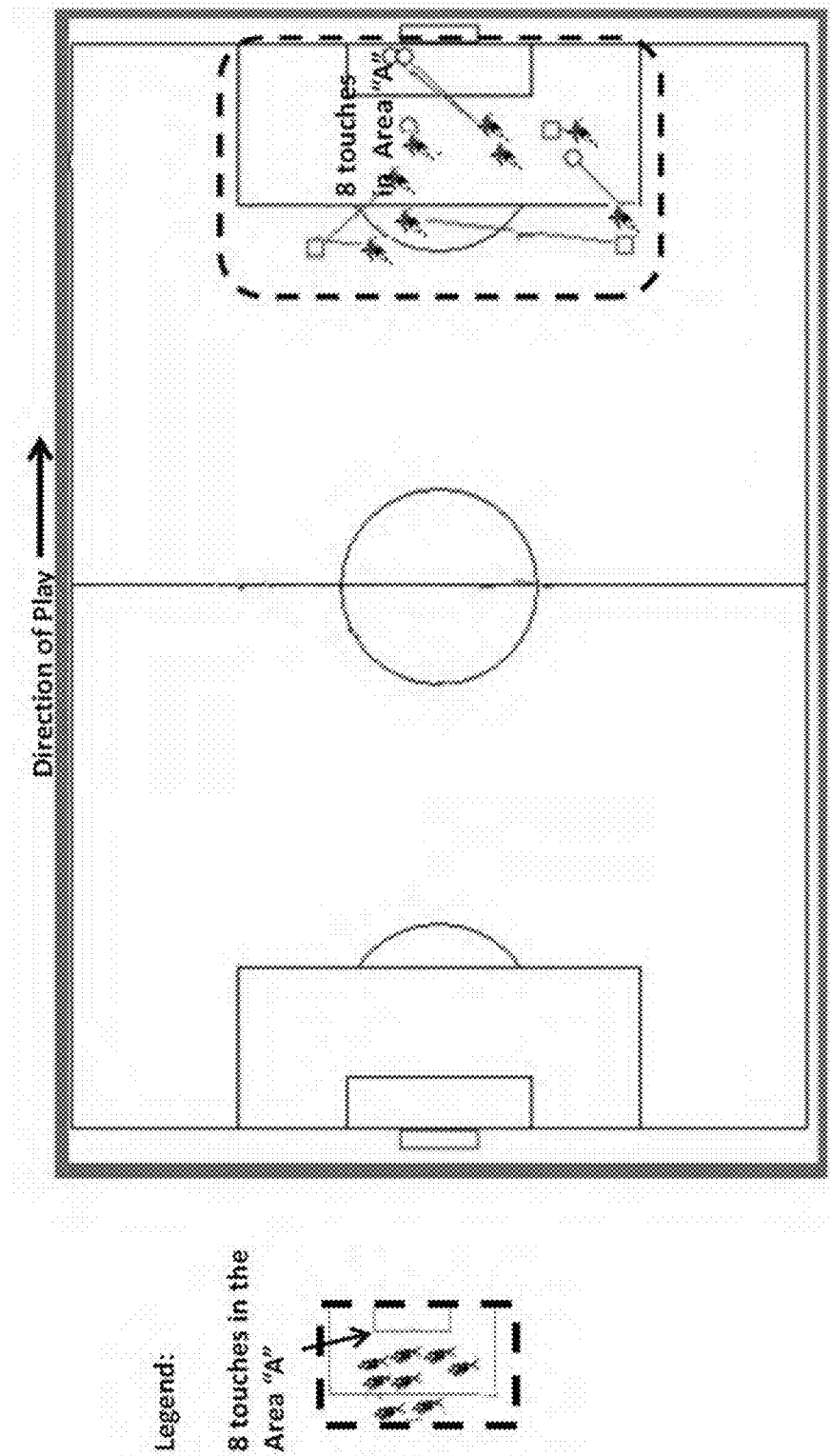
Figure 35:
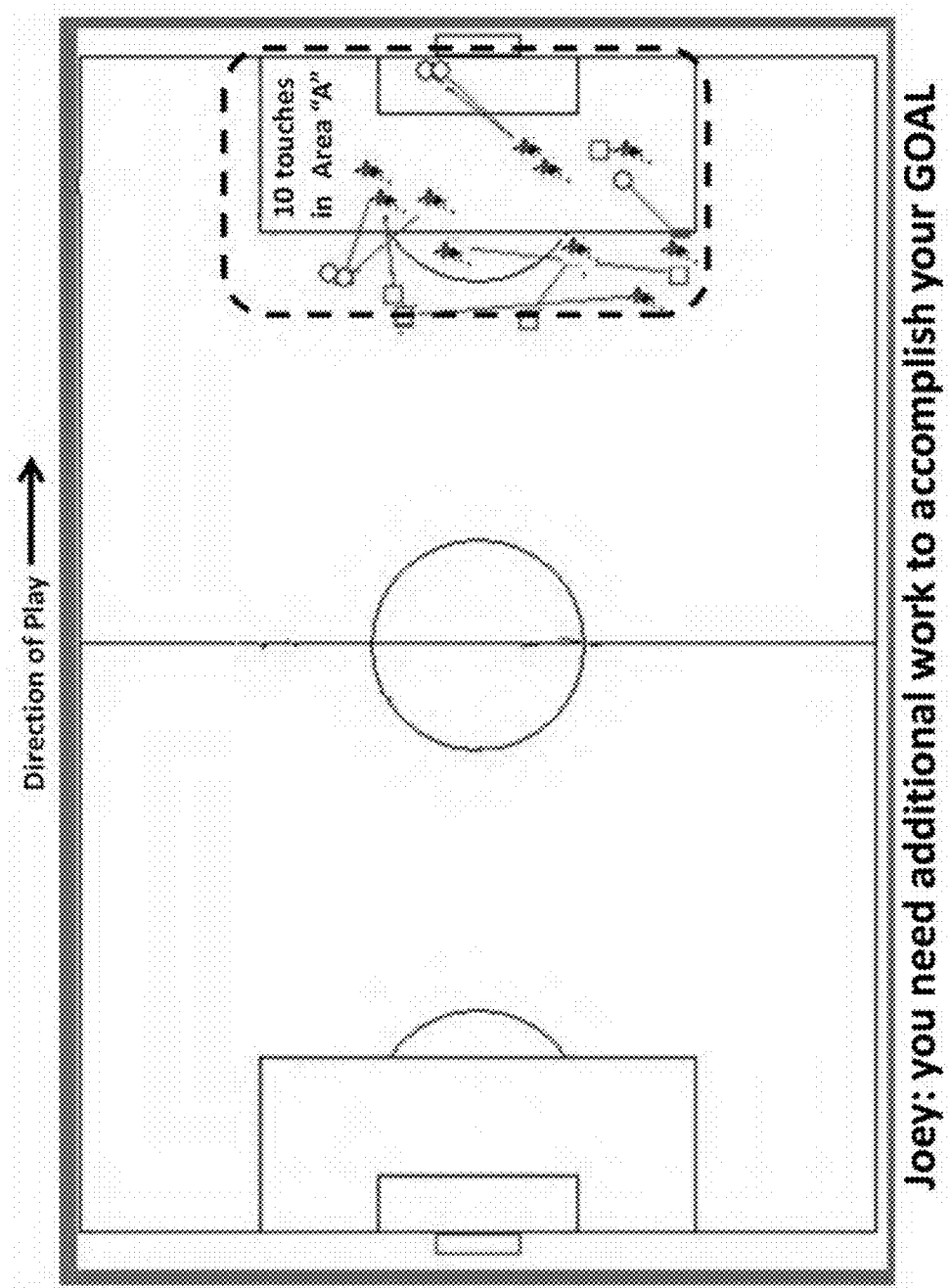
Figure 36:
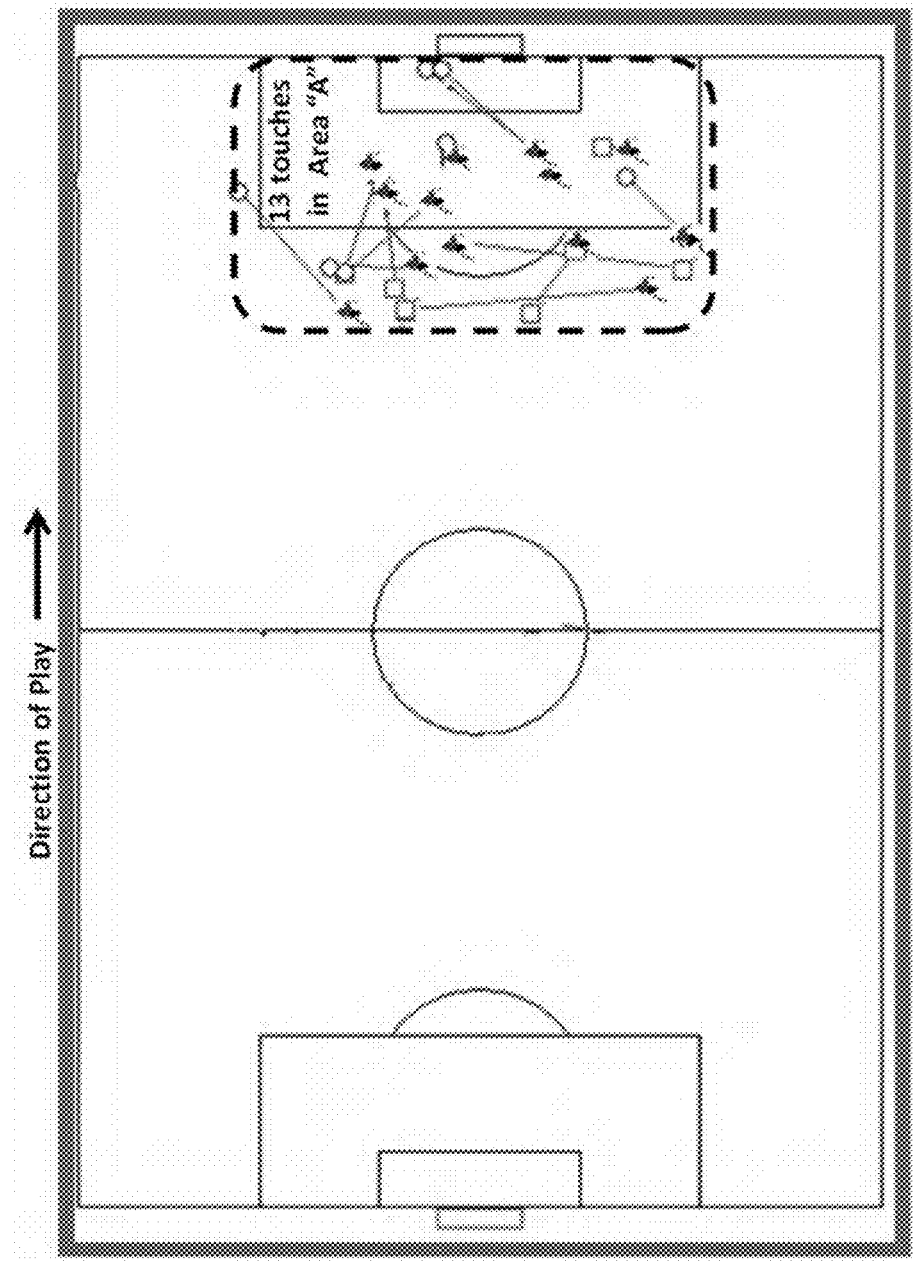

Goal 6 is to perform 13 total passes into the scoring box. In some embodiments, Goal 6 can be accomplished in 3 steps. The purpose of this goal is to motivate and encourage the player to be proactive and perform as many passes as possible passes into the box. Once again, the Role Model can be selected to be J. K. FIG. 34 shows step 1 of Goal 6, which includes performing 8 total passes into the scoring box. Step 2 of Goal 6 can include requiring the player to perform 10 total passes into the scoring box, as illustrated in FIG. 35. Finally, in step 3 of Goal 6, the player is required to perform 13 total passes into the scoring box, as illustrated in FIG. 36.

Figure 37:
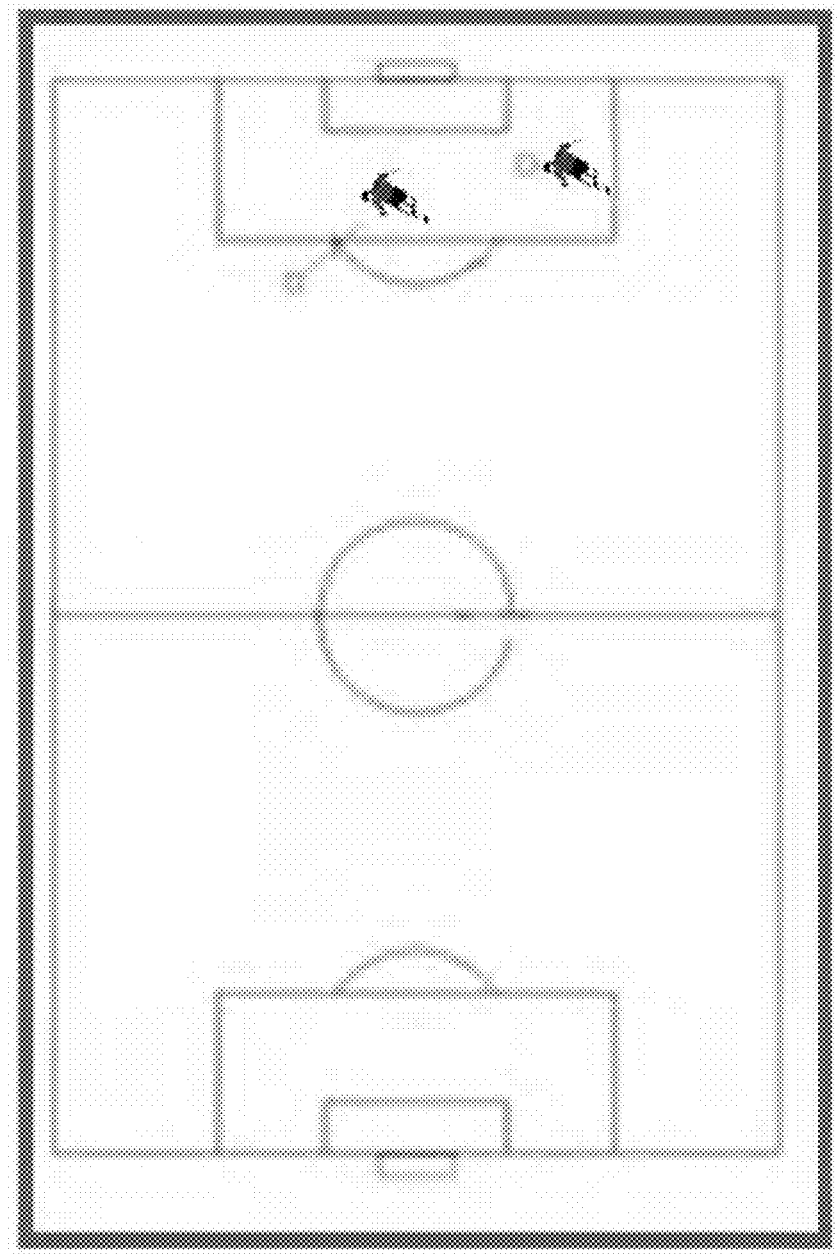
Figure 38:
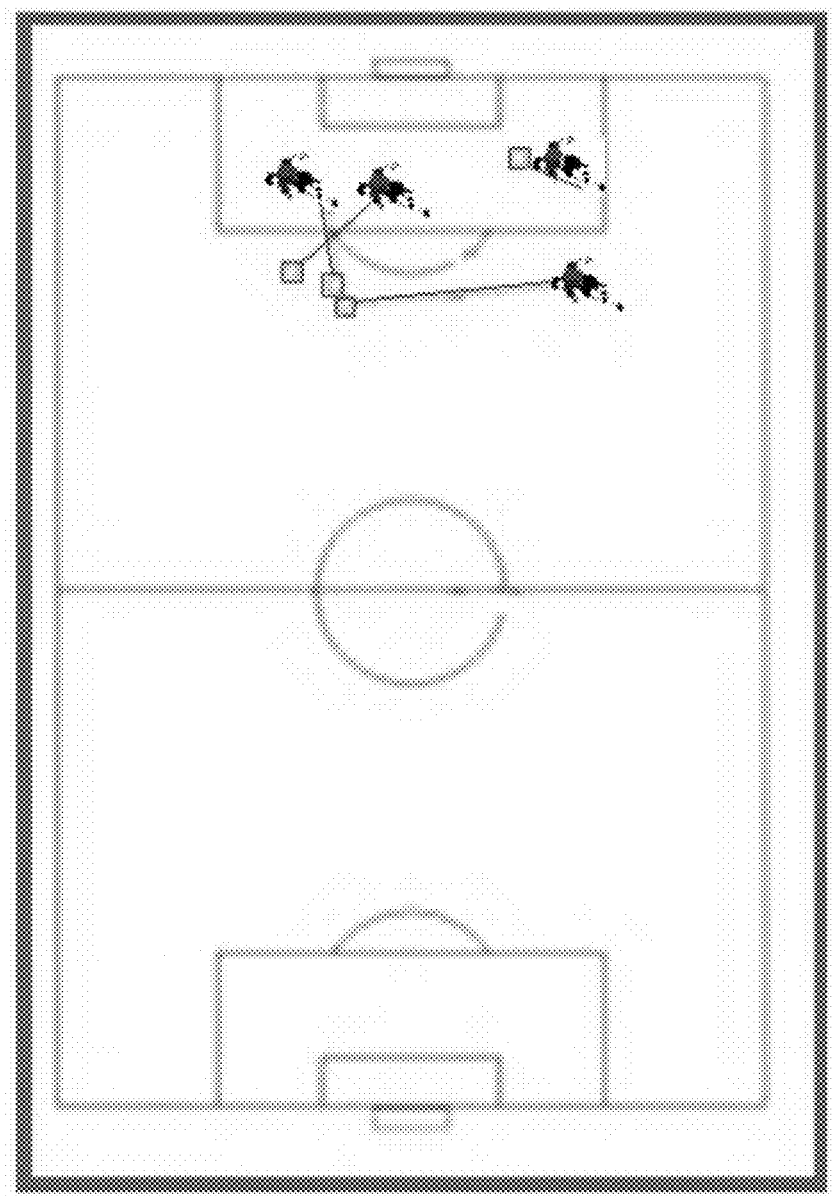
Figure 39:
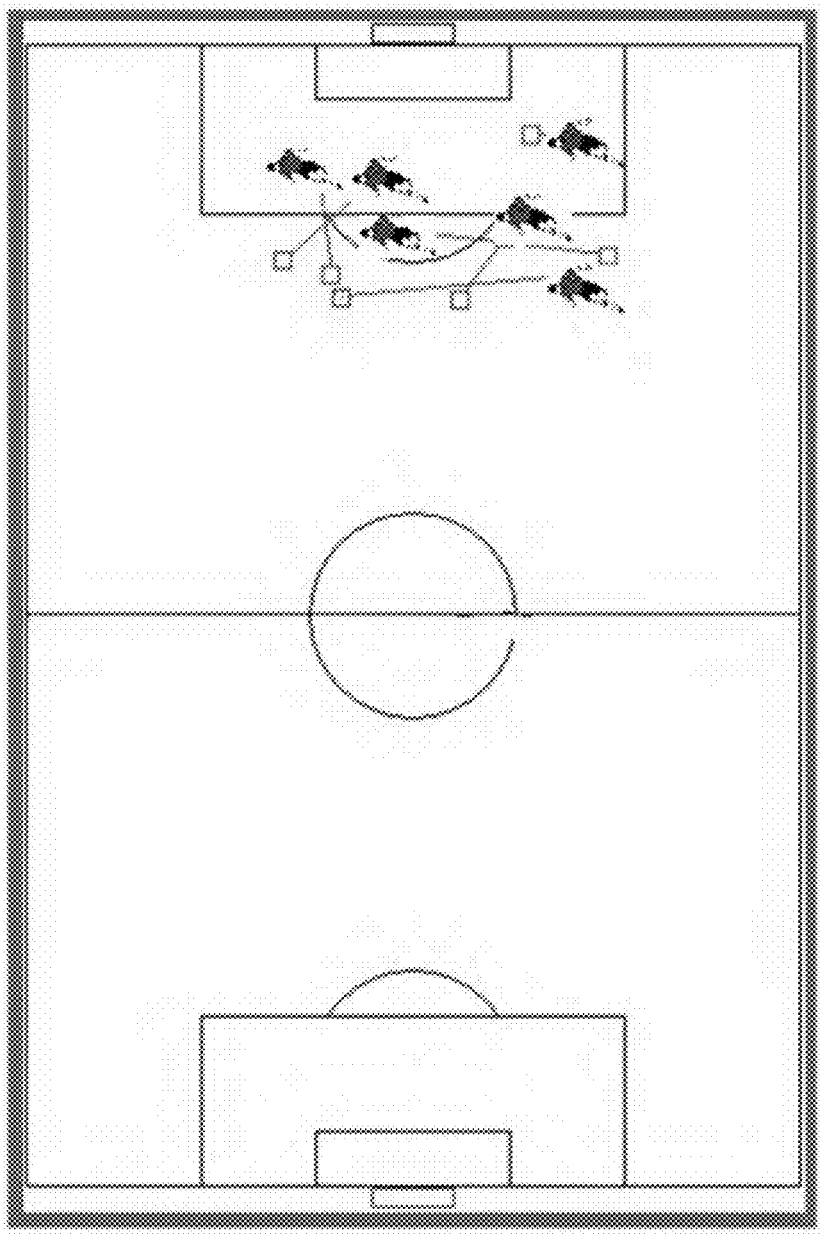

Goal 7 is to perform six completed passes into the scoring box. A pass is considered a completed pass when a player passes the ball to his teammate during the game into the scoring box. The purpose of this goal is to motivate and encourage the player to connect as many passes as possible with his teammates, which can include all completed passes in any direction or location on the field. In some embodiments, Goal 7 can be carried out in three steps. For example, and as illustrated in FIG. 37, step 1 includes performing two completed passes into the scoring box, step 2 can include requiring the player to complete four passes into the scoring box (as illustrated in FIG. 38), and step 3 of Goal 7 can include performing six completed passes into the scoring box (as illustrated in FIG. 39). At each step of this goal, one or more messages can be provided for the player to inform the player as his status and success in accomplishing his goal.

Figure 40:
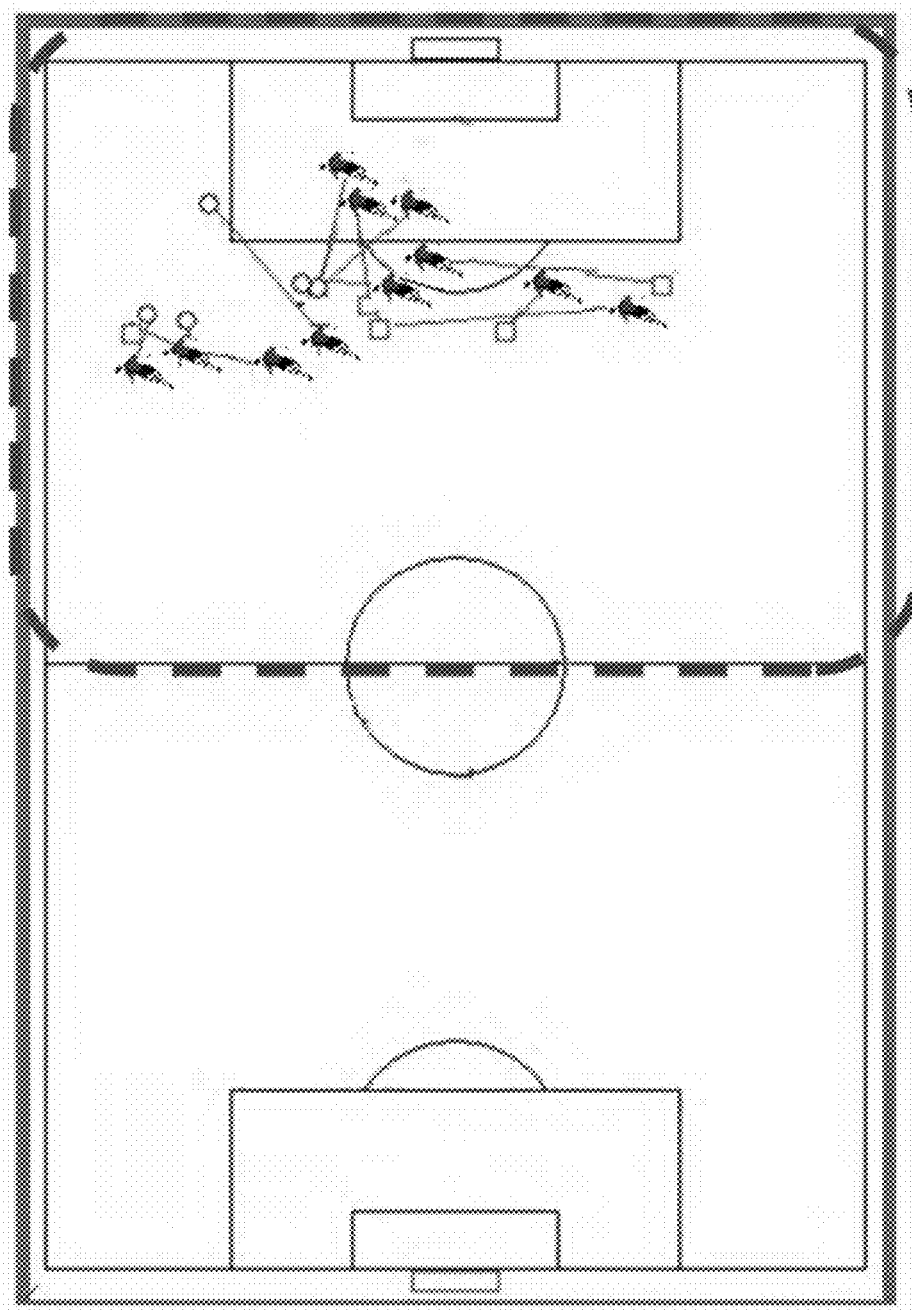
Figure 41:
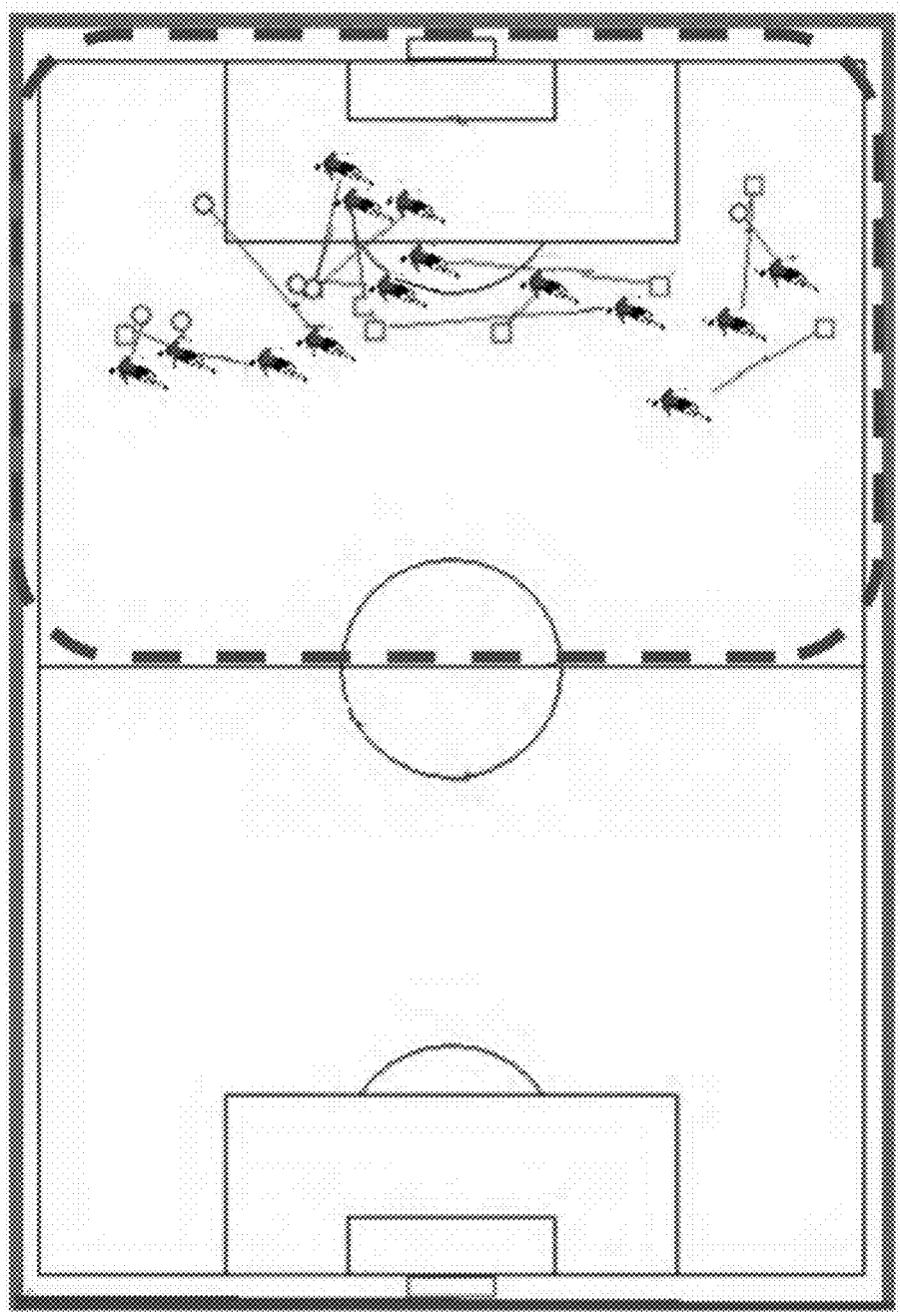
Figure 42:

Goal 8 is to perform 19 forward passes into the Offensive Part of the Playing Area (OPPA). The purpose of this goal is to motivate and encourage the player to perform passes into the offensive part of the playing field, measure the player performance, and give him feedback on his accomplishment. In some embodiments, Goal 8 can be accomplished in three steps. For example, in step 1, as illustrated in FIG. 40, the player must perform 11 passes into OPPA, and in steps 2 and 3 of Goal 8, the player perform 14 and 19 passes into OPPA, respectively, as shown in FIGS. 41 and 42, respectively.

Figure 43A:
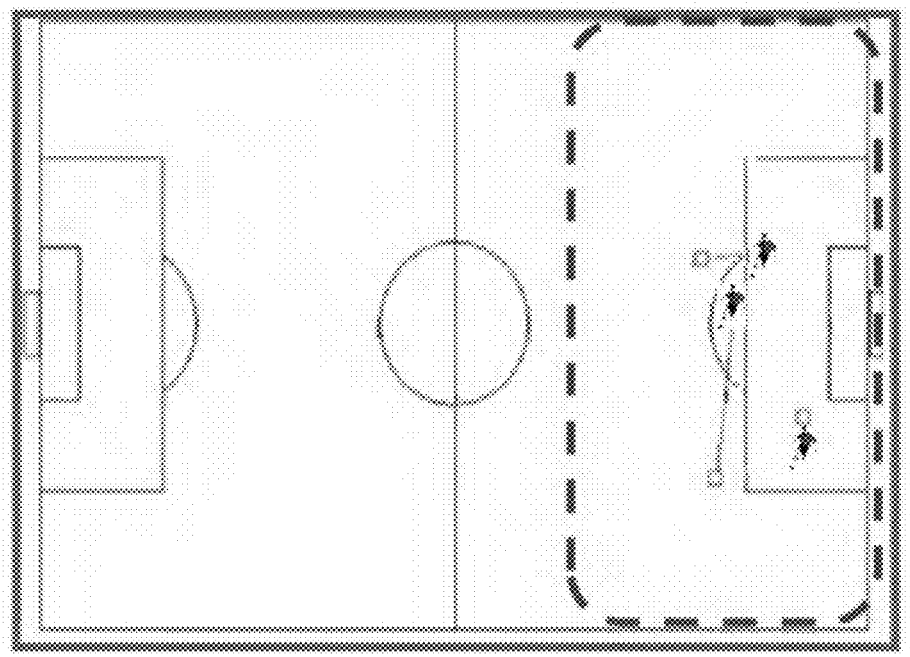
Figure 43B:
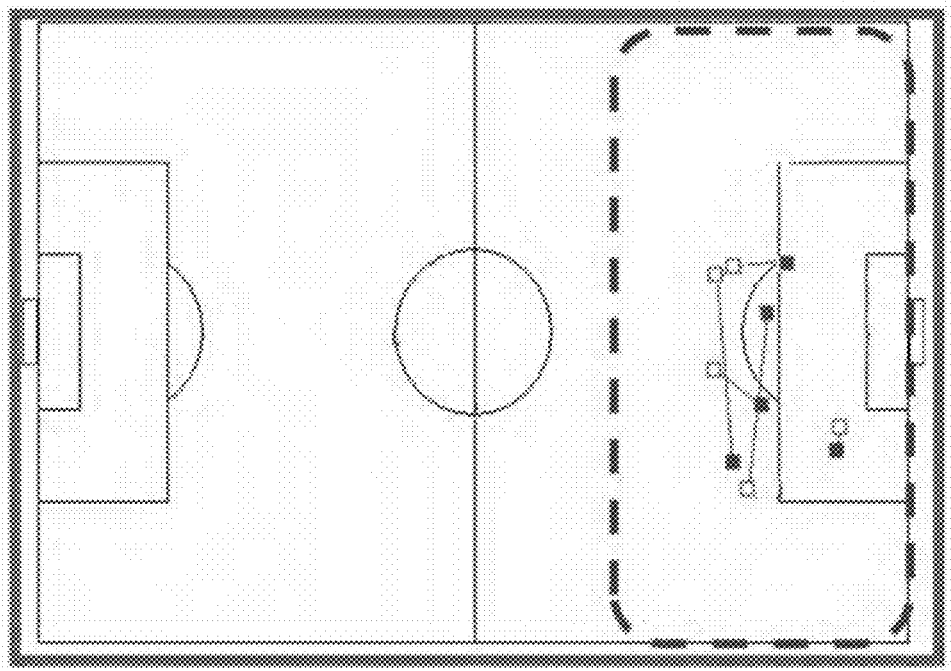
Figure 44:
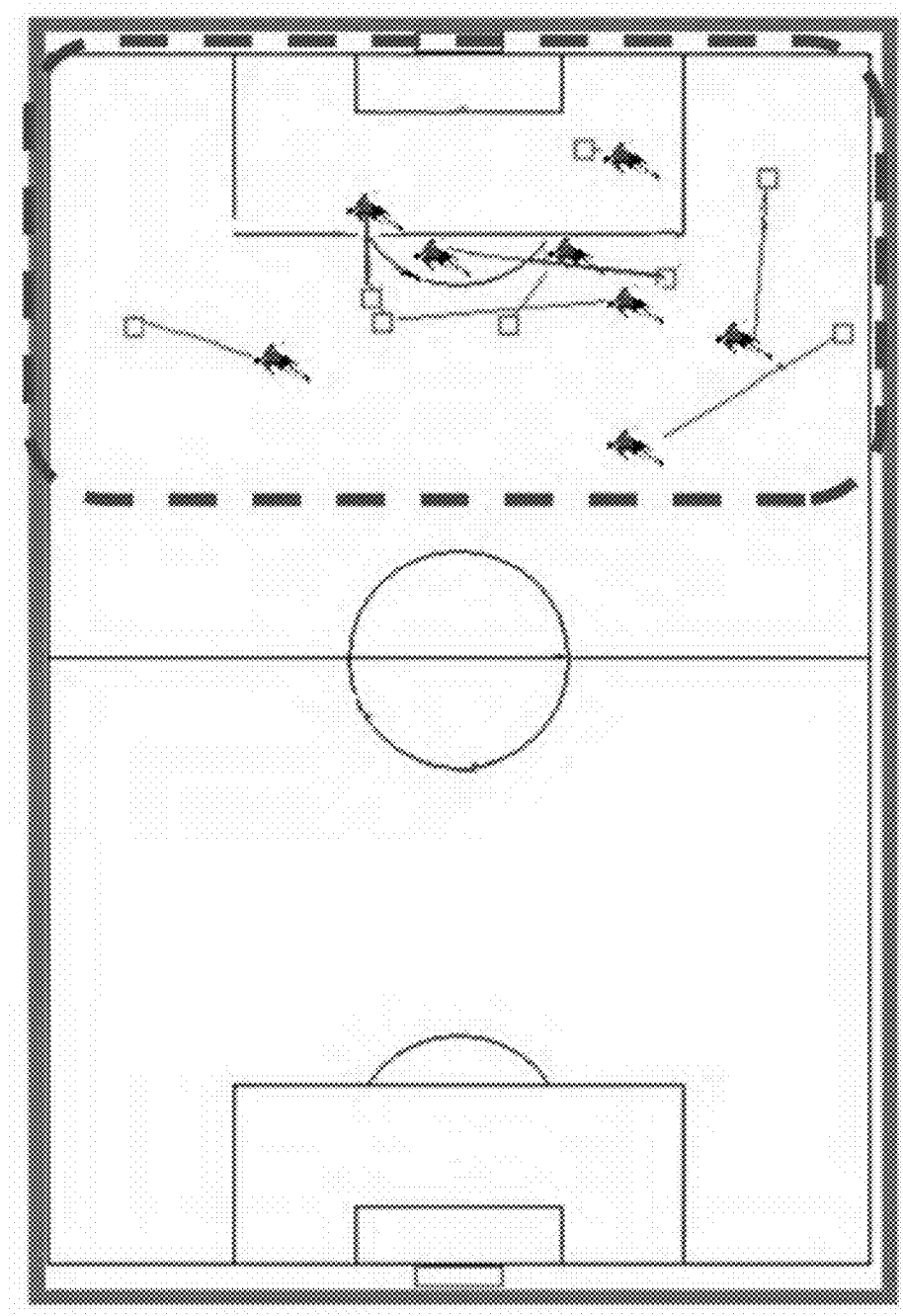

Goal 9 is to perform eight completed forward passes into OPPA. The purpose of this Goal is to motivate and encourage the player to perform passes into the offensive part of the playing field, measure the player performance, and give him feedback on his accomplishment. In some embodiments, Goal 9 can be accomplished in three steps. For example, in step 1, as illustrated in FIG. 43A, the player must perform three completed passes into OPPA, and in steps 2 and 3 of Goal 9, the player must perform five and eight competed passes into OPPA, respectively, as shown in FIGS. 43B and 44, respectively.

Figure 45:
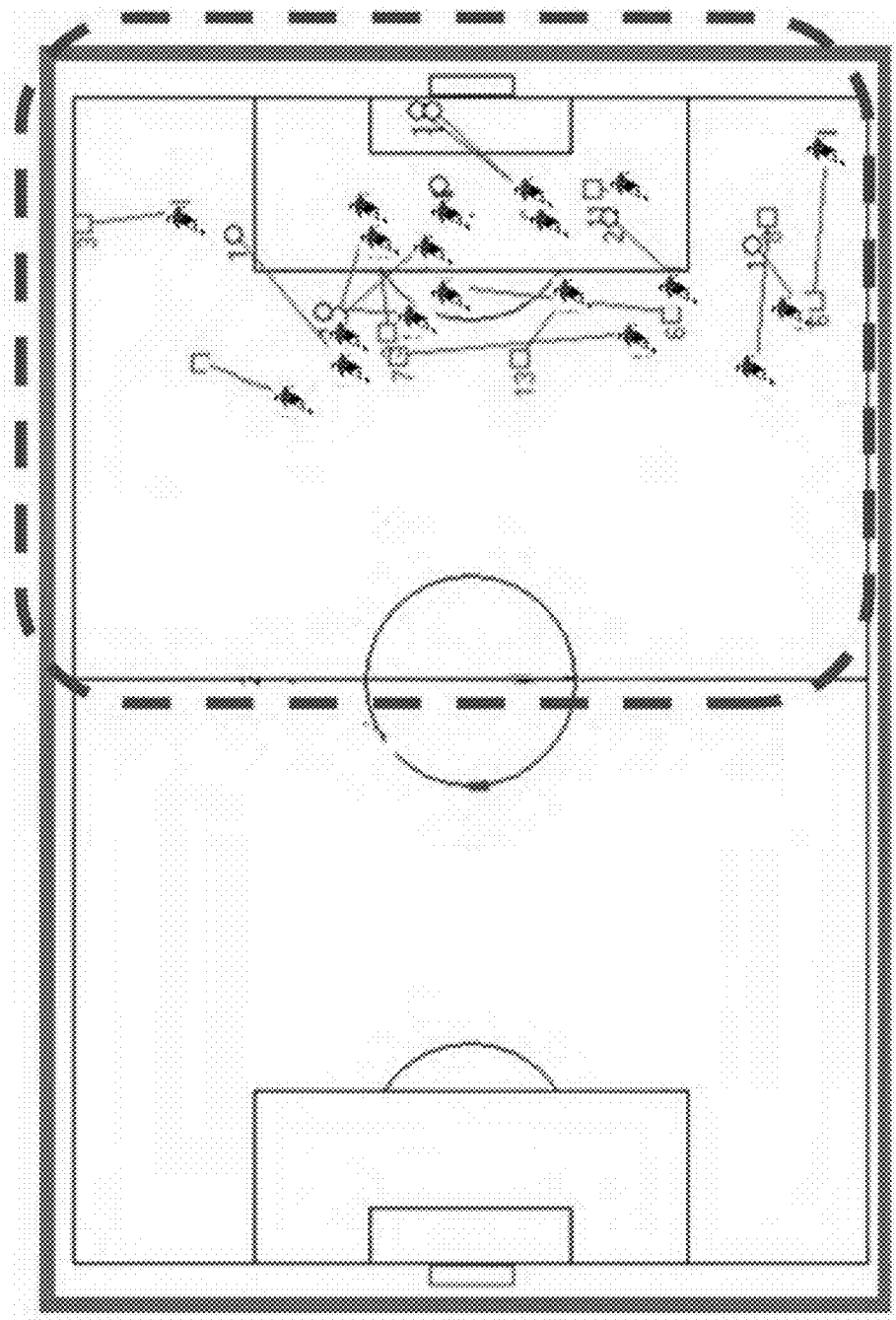
Figure 46:
Figure 47:
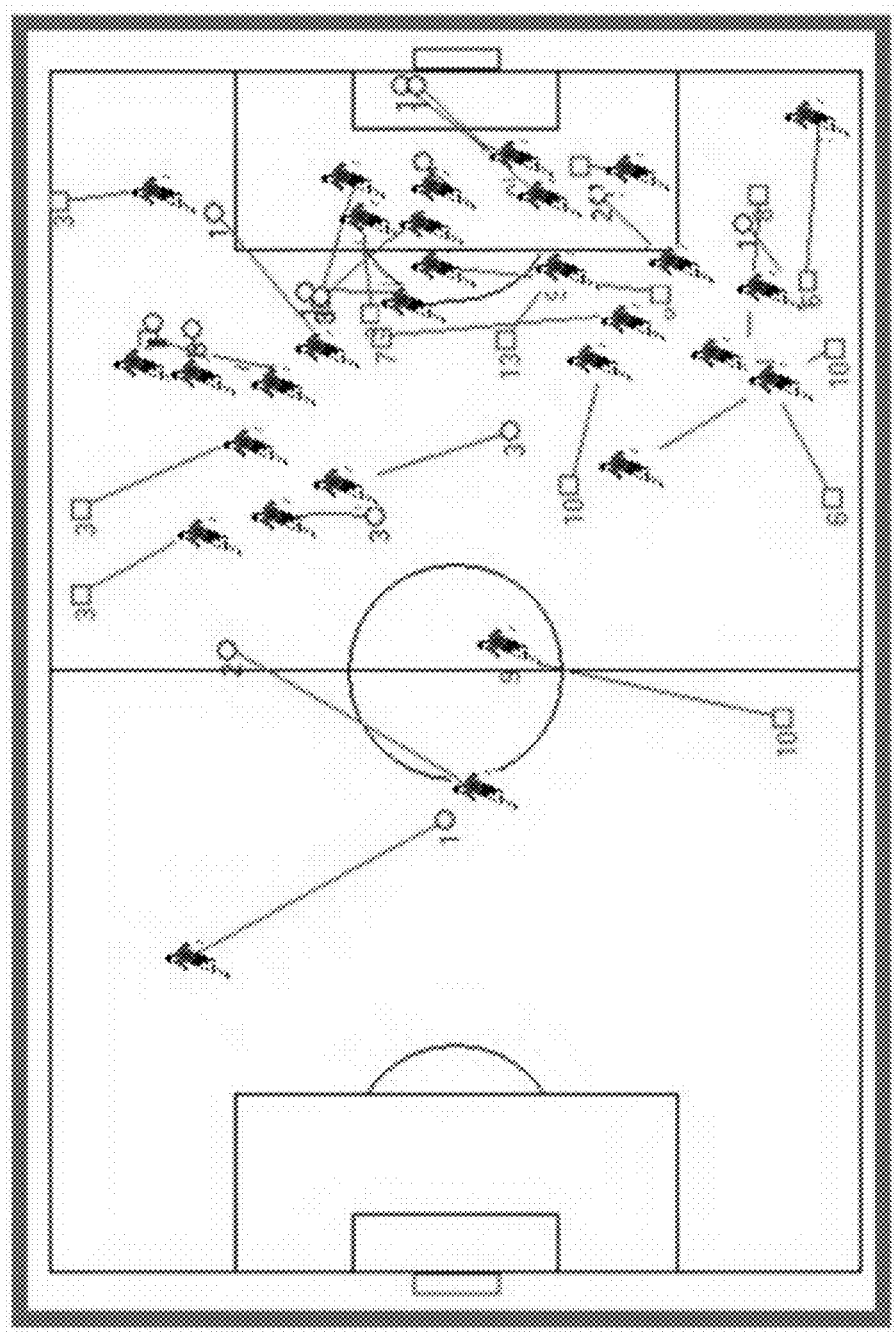

Goal 10 is to perform 31 total passes during the game. The purpose of this goal is to motivate and encourage the player to perform as many passes as possible, measure the player performance, and give him feedback on his accomplishment. In some embodiments, Goal 10 can be accomplished in three steps. For example, in step 1, as illustrated in FIG. 45, the player must perform 10 passes, and in steps 2 and 3 of Goal 10, the player must perform 28 and 31 passes, respectively, as shown in FIGS. 46 and 47, respectively.

Figure 48:
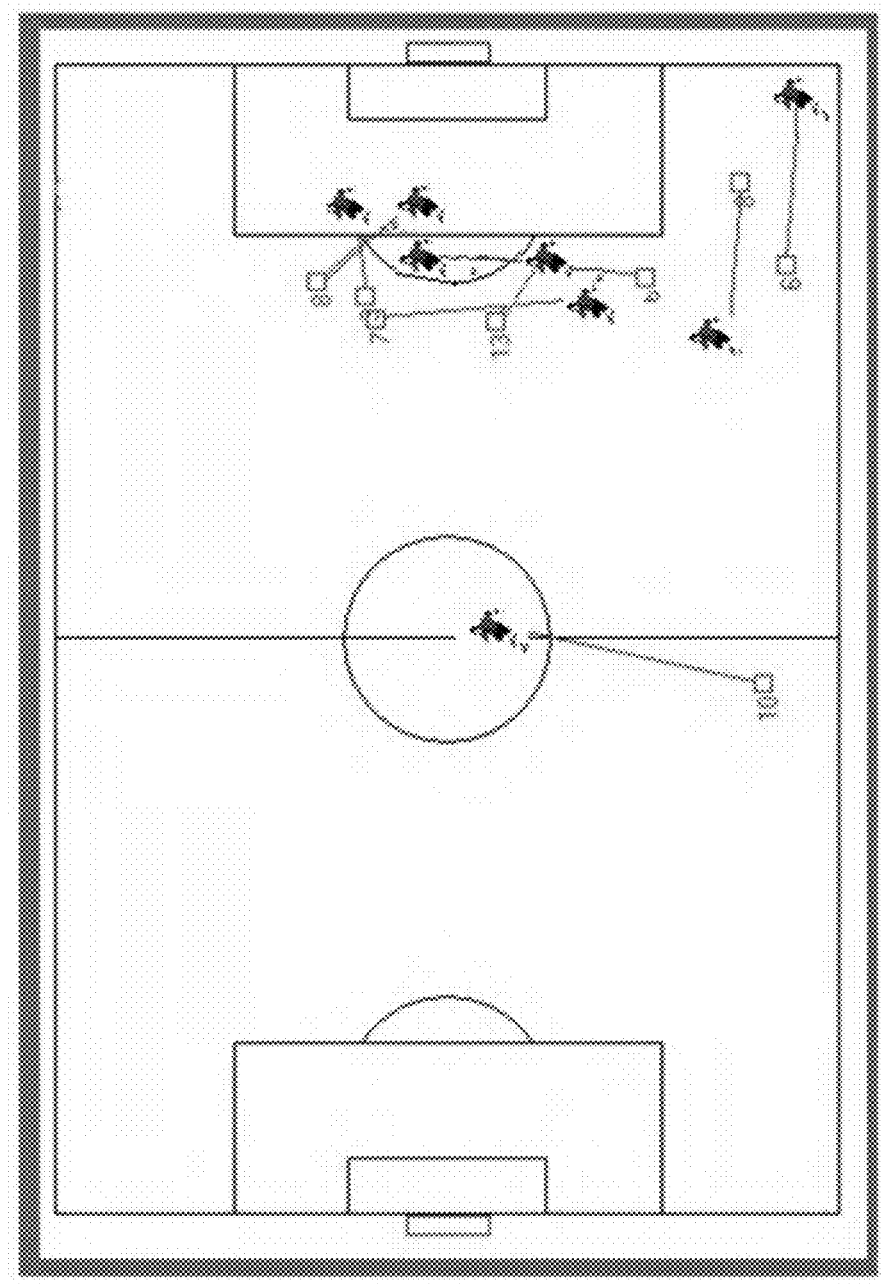
Figure 49:
Figure 50:

Goal 11 is to perform 16 completed passes during the game. The purpose of this goal is to motivate and encourage the player to perform as many passes as possible, measure the player performance, and give him feedback on his accomplishment. In some embodiments, Goal 11 can be accomplished in three steps. For example, in step 1, as illustrated in FIG. 48, the player must perform 8 passes, and in steps 2 and 3 of Goal 11, the player must perform 12 and 16 passes, respectively, as shown in FIGS. 49 and 50, respectively.

Figure 51A:
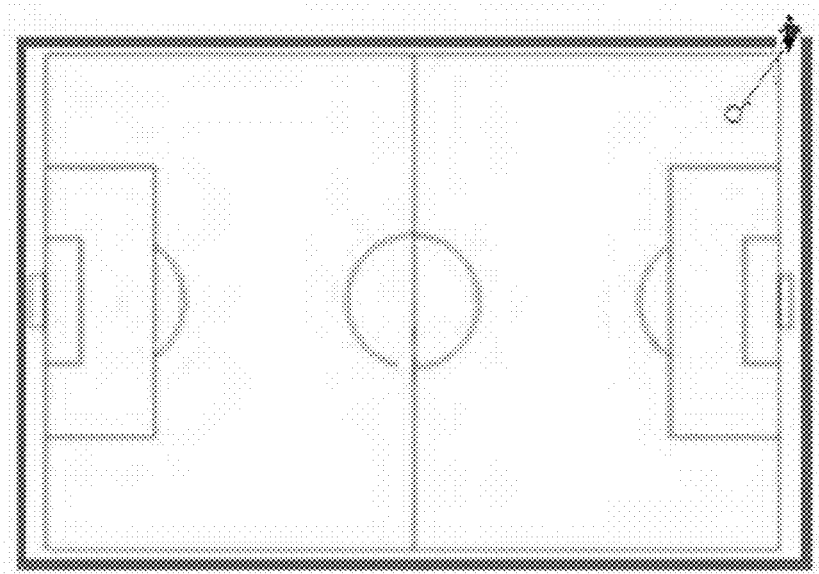
Figure 51B:
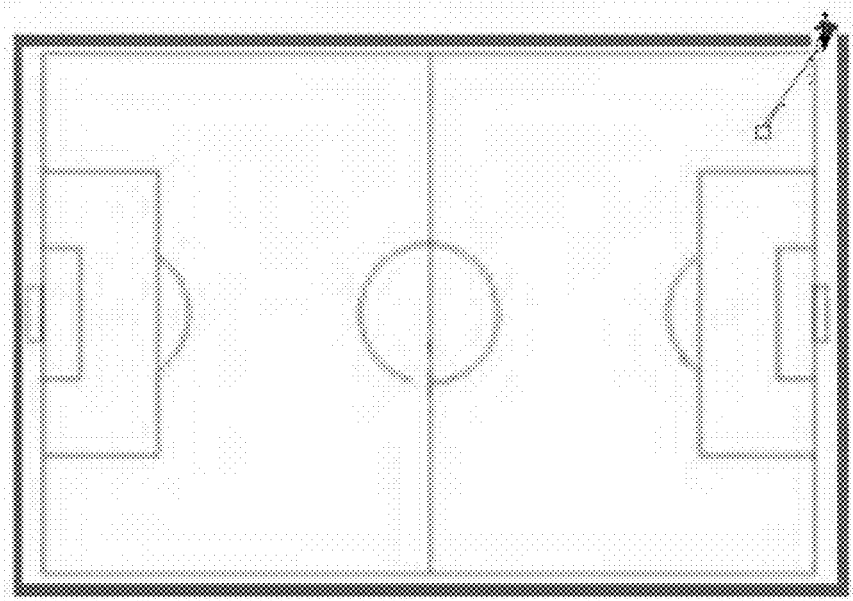

Goal 12 is to perform one complete corner kick. The purpose of this goal is to motivate and encourage the player to be proactive and to perform as many corner kicks as possible. The purpose is to also measure the player performance and give him feedback on his accomplishment. In some embodiments, Goal 12 can be accomplished in two steps. For example, in step 1, as illustrated in FIG. 51A, the player must perform a corner kick, and in step 2 of Goal 12, the player must perform and complete a corner kick as shown in FIG. 51B.

Figure 52:
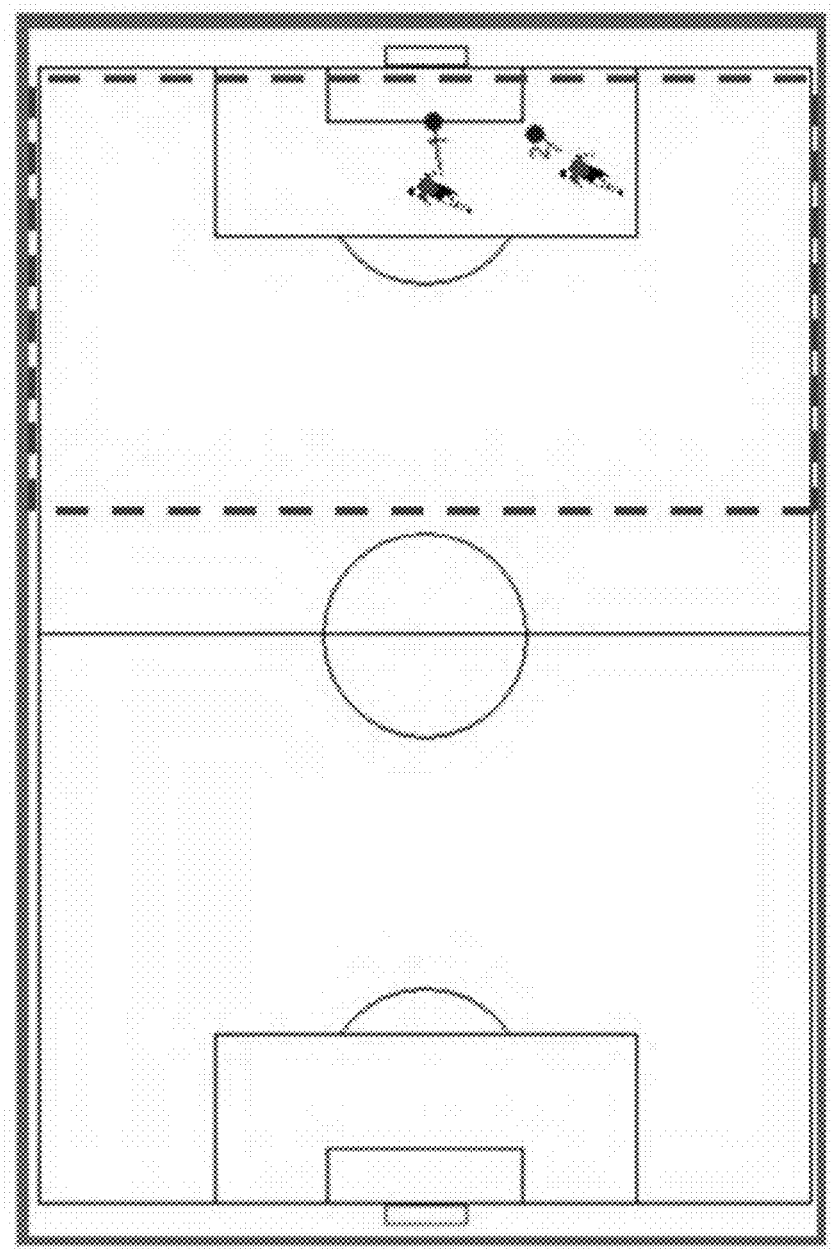
Figure 53:
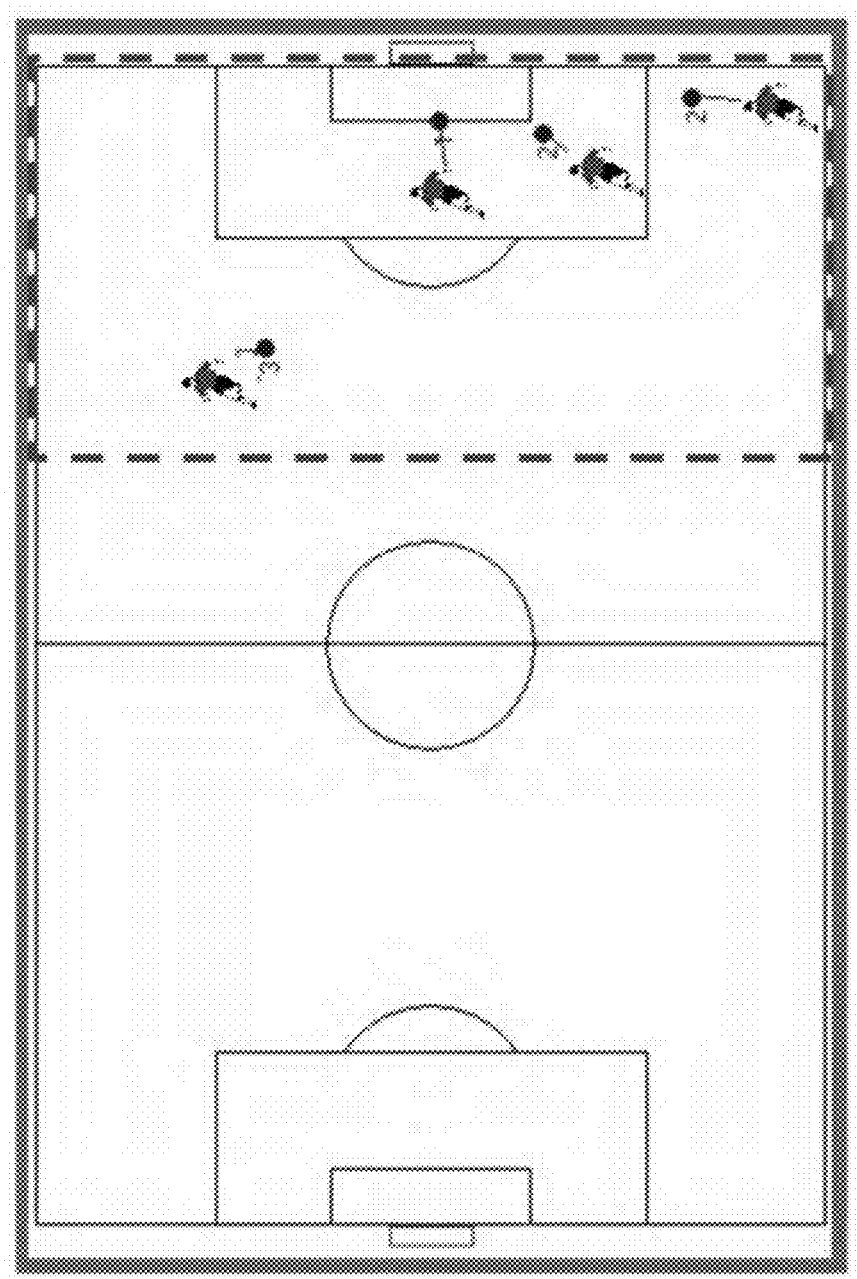
Figure 54:
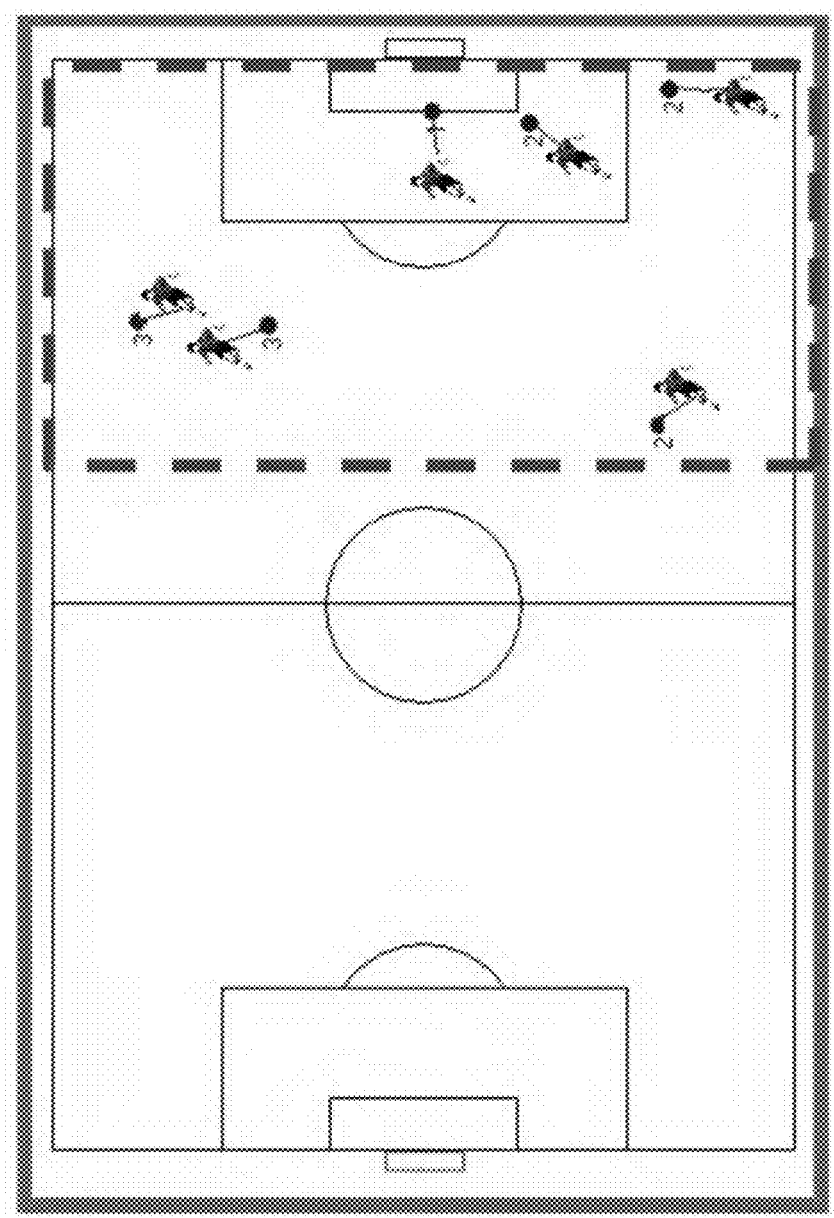

Goal 13 is to intercept a total of 6 passes in the attacking ⅓ of the field (i.e., ⅓ of the field that is closest to opponent's goal). The purpose of this goal is to motivate and encourage the player to be proactive in intercepting passes by the opponents. The purpose is to also measure the player performance and give him feedback on his accomplishment. In some embodiments, Goal 13 can be accomplished in three steps. For example, in step 1, as illustrated in FIG. 52, the player must intercept 2 passes in the attacking ⅓ of the field, and in steps 2 and 3 of Goal 13, the player must intercept 4 and 6 passes in the attacking ⅓ of the field, respectively, as shown in FIGS. 53 and 54, respectively.

Figure 55:
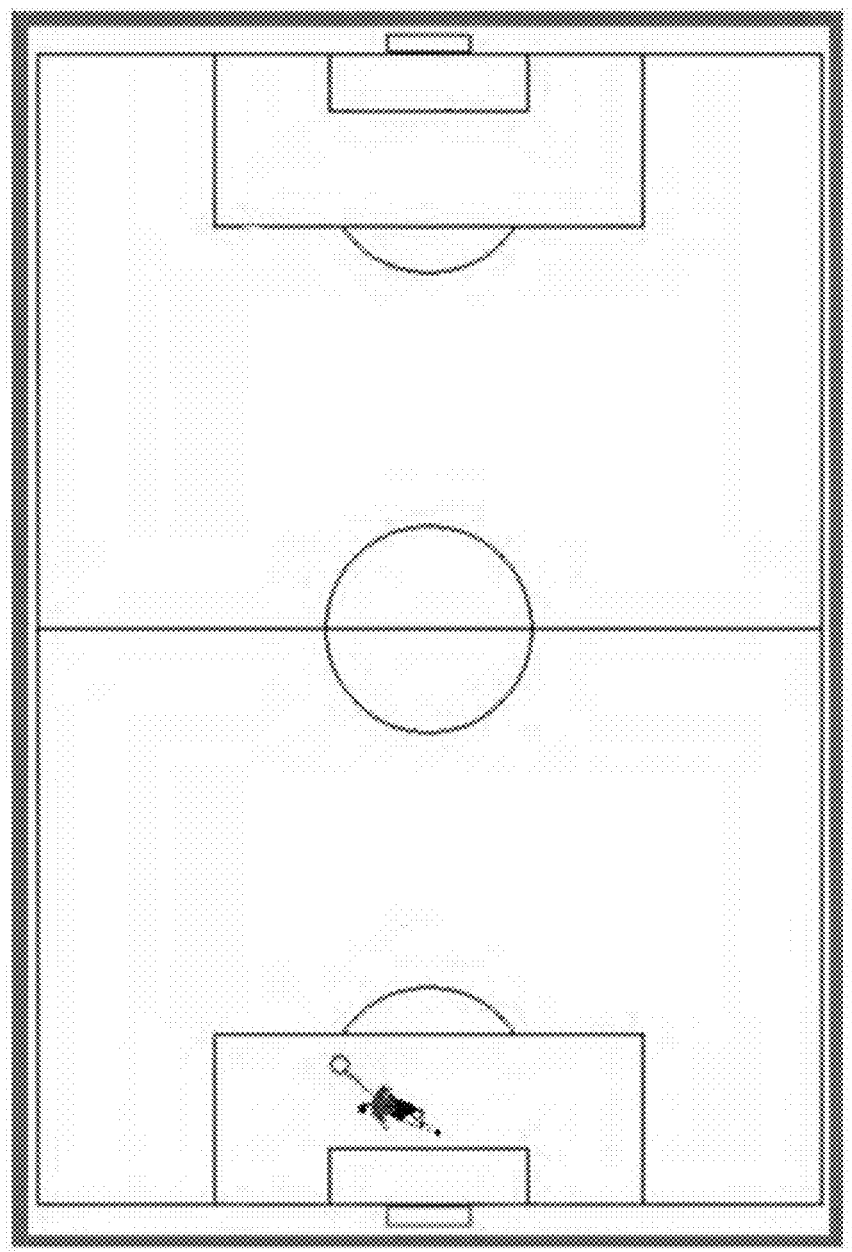
Figure 56:
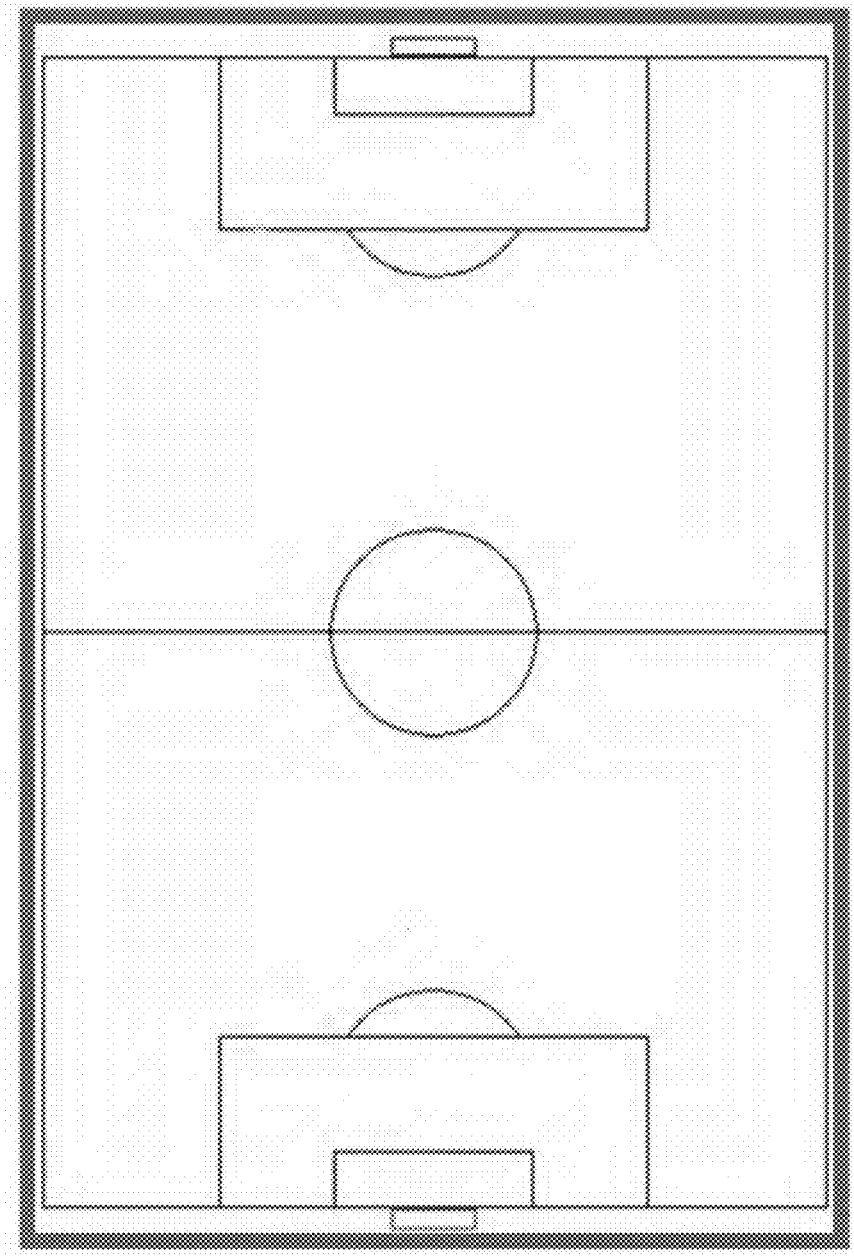

Goal 14 is to not to lose any passes in the defensive ⅓ of the field (i.e., ⅓ of the field that is closest to the player's own goal). The purpose of this goal is to motivate and encourage the player to be proactive in not losing any passes in an important part of the field that has a higher likelihood of producing goals for the opponent. The purpose is to also measure the player performance and give him feedback on his accomplishment. FIG. 55 shows an example scenario in which the player has lost one pass in the defensive ⅓ of the field, thereby prompting the message that his goal was not obtained. In contrast, FIG. 56 shows a completed goal of not losing a ball in the defensive part of the field.

It should be noted that in describing Goals 1 through 14, various numerical values were used to illustrate the underlying concepts related to the number of shots, passes, kicks, etc. that must be performed by the player to successfully complete a particular goal level, or to complete one or more steps within a goal level. It is however understood that other numerical values and number of steps may be selected for completing a goal level. In addition, the number of goals can be changed as needed based on a variety of factors such as the type of sports (e.g., soccer versus basketball), the level of player's skill (e.g., professional league versus youth league), and the like.

Referring back to FIG. 1, step 7 includes the player practicing and/or playing games to achieve the goals that were set in step 6. In step 9, the player can work with his team and at home. The information corresponding to the user is collected, analyzed, and presented using, for example, software applications that run on a computing system such as a laptop, a tablet, or even a smart phone.

Figure 57:
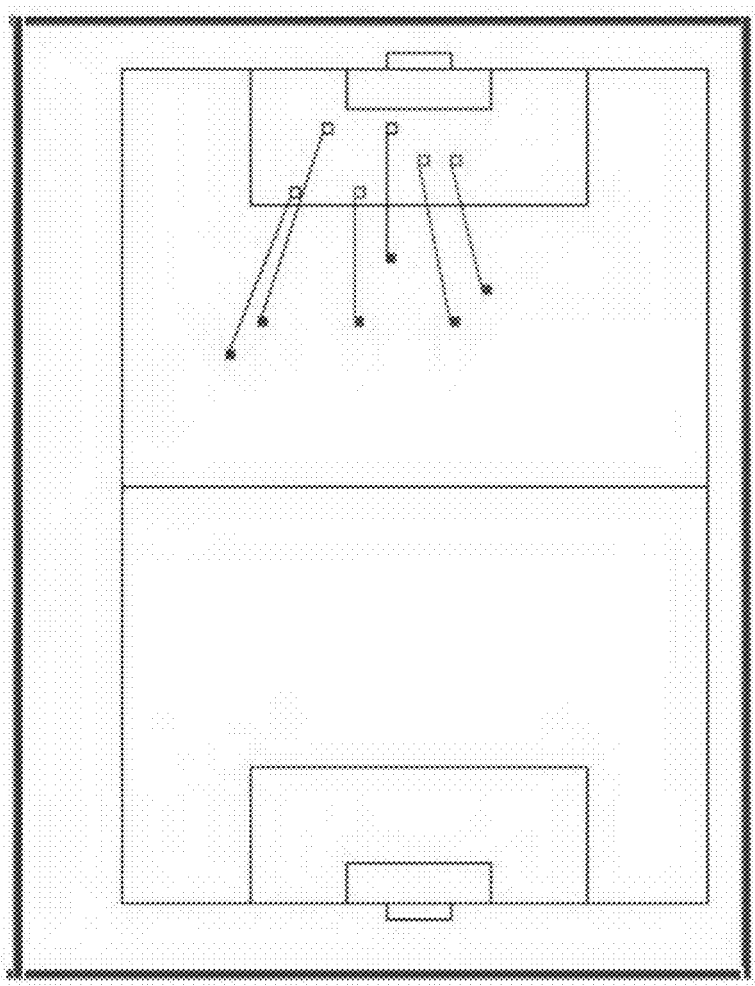
FIGS. 57 and 58 illustrate example screenshots for feedback results, in accordance with the described embodiments.
Figure 58:
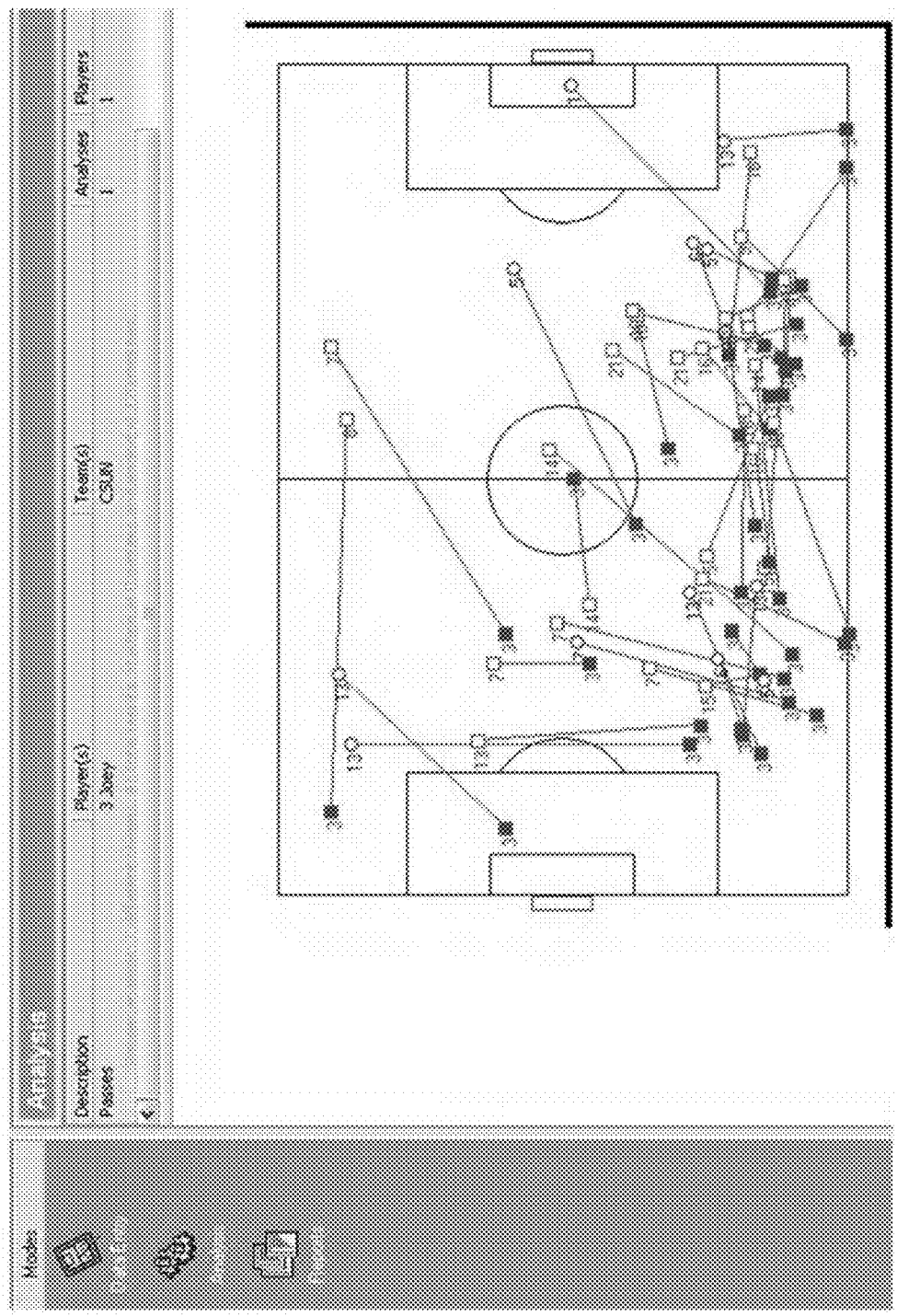

Referring back to FIG. 1, step 8 relates to performance feedback provided to the player. In this regard, one of at least two different technologies may be used to provide feedback to the player. The first technique is referred to as MPG, which gives the player immediate results of his goal performance. The second technique is referred to as Second Look™, which requires several steps to provide the results of the player's performance. FIGS. 57 and 58 provide example screenshots of MPG and Second Look™ performance feedback results, respectively. Additional examples of feedback provided to the player were previously described in connection with, for example, Goal 7 and corresponding FIGS. 37 to 39.

Referring again to FIG. 1, step 9 of the flowchart relates to providing solutions, which can include, for example, providing training tips to the user of the system to allow the player to achieve his/her goals. For example, if the player has failed to successfully complete the goal, or steps within the goal, at a particular level, solutions and tips can be provided to illustrate how the player can improve his/her performance to facilitate achieving the goals.

The following provides an example of tips and explanations that can be provided to a player. In this example, it is assumed that the starting point is to complete step 1 of Goal 1 that was described earlier. As discussed above, Goal 1 requires learning how to cover primary playing area (PPA). In step 1 of Goal 1, the player has to learn to move inside his PPA and to perform 24 touches with the ball inside this PPA similar to, his Role Model, J. K. The explanation provided to the player can include the following:

1. Explain to the player the borders of the area we call PPA so he is aware what the borders are and why it is beneficial to him and the team.
1.1 The borders of the player PPA are as shown in the diagrams, such as the one in FIG. 25. It covers the entire attacking half.
1.2 The player is moving everywhere, which is making it difficult for the defense to cover him and defend against him.
1.3 The player is moving around his area, but tries to get closer to the ball, which means that if his teammate is receiving the ball, he is ready to get the next pass from his teammate. If an opponent has the ball, then the player is ready to defend and possibly take the ball back for his teammate.

2. This explanation can be performed in several ways, e.g., by showing a visual diagram and/or giving actual references from around the field or on the field, such as trees, buildings/structures, goal post, and other field markings.
3. This may be performed as follows:
3.1 Walk through your area (PPA) before the game or practice to get familiar with your area of play. Make some mental notes to yourself about the location of the PPA. For example, note the location of trees, benches, the position of the sun at a particular time, etc.
3.2 Start running around the PPA for a few minutes, and get a feel for the space.
3.3 Run around the PPA using the interval method: walk slow/stop, then run sprints, then run slow, then continue for a few minutes to evaluate your condition (e.g., record the time for reference for the next time).
3.4 Repeat step 3.3 the next day, and try to lengthen the duration by a few minutes. Then, record the time for reference for the next time.
3.5 Continue to repeat for the next few days continue until the activity can be performed for the duration of the entire game (e.g., 90 minutes).

In order to have more fun you may team-up with another player who can be using a ball. In particular, try first to talk to him about communication; that is, how you exchange signals about passing the ball to him. Learn about his skills and learn to be in the right position so you can receive the ball.

3.6 Each time you receive the ball, it will count as a touch for you, and you will get closer to achieve your goal of touching the ball 24 times in the PPA.
3.7 The second way the player will get credit toward his goal is to intercept the ball in the PPA. This way, the player will perform more touches.
3.8 The third way of performing touches, it to take free kicks.
3.9 The next step for the player is to practice with a teammate, and if possible, with a player who will be assigned to play next to him during the actual game.
3.10 The next step is to play in real practice game.
3.11 The real test is during the real game.

In some embodiments, performance records are kept in all phases (or goals) as this will help the player to evaluate his performance. Recording the performance may be done manually or with a computer.

Another Example Embodiment for Implementing Goal Setting

In soccer, "flooding zones" is a term that is used to describe patterns of runs up top when the team is attacking through flank midfielders. When you flood zones, your strikers are all "flooding" over onto one side of the field to create numbers around the anticipated service zones. It also clears the opposite side of the field if the defense is tracking the striker. This technique is designed to pull defenses apart. Flooding zones requires a lot of energy from the players, and employing this technique all the time places very high demands on all the players. Thus, the best time to implement flooding zones is when the ball is on the flank in midfield, at which point, all strikers should be within service distance of the ball.

Figure 59:
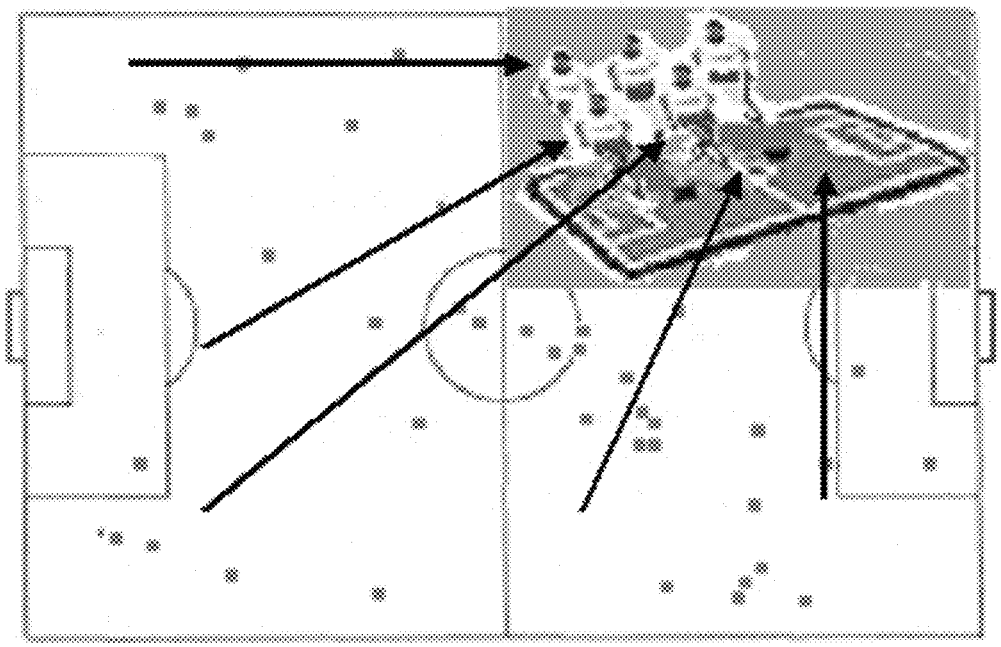
FIG. 59 illustrates an example of the flooding zones technique in soccer.
Figure 60:
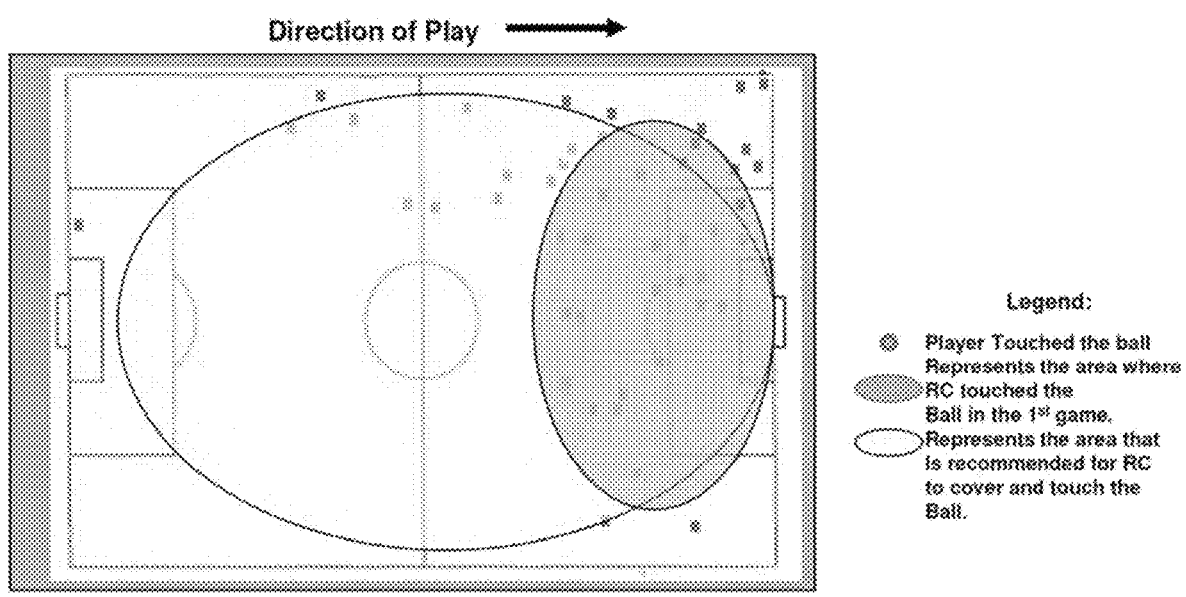
FIG. 60 illustrates an example of the current and desired coverage for a player that can be achieved using embodiments of the disclosed technology.
Figure 61A:
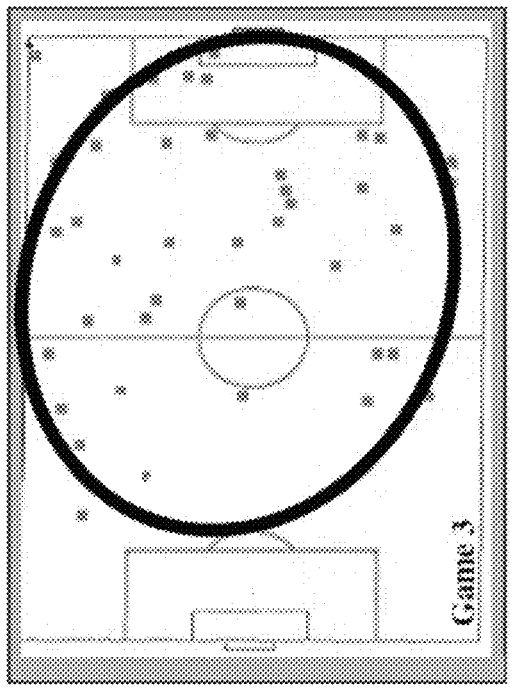
FIGS. 61A-61D illustrate an example of the improvement in coverage through a season that was achieved using embodiments of the disclosed technology.
Figure 61B:
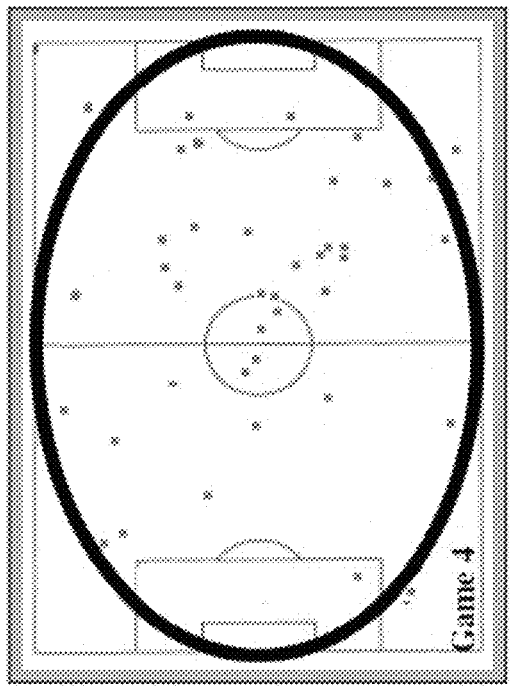
Figure 61C:
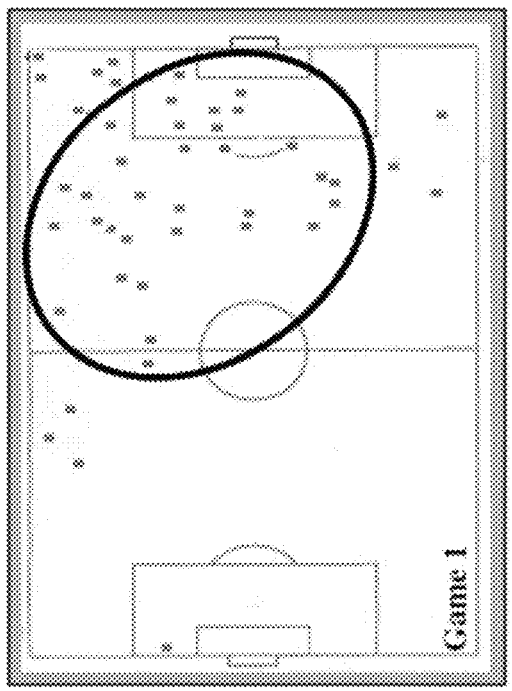
Figure 61D:
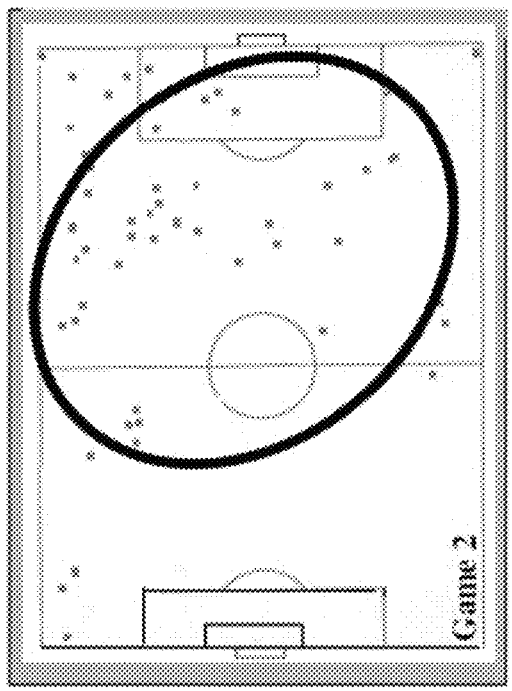

FIG. 59 illustrates an example of flooding the zone for a player "R.C.," wherein each dot represents where a player touched the ball. FIG. 59 shows R.C.'s mobility and range during a single season. Because flooding zones is a sideline-to-sideline demand, it is critical that the front-runners cover a lot of ground. To effectively flood zones, R.C. should be receiving the ball at a variety of points on the field. We also want our front-runners to track their marks back into the midfield and into the defensive third. In this example, R.C., a forward, was not playing with enough mobility, e.g., she was not checking back, not showing enough for the ball, and not playing defense outside of her area. FIG. 60 illustrates an example of current and desired performance for R.C., which requires her to increase the size of the area of the field that she was covering, both offensively and defensively. Using the Goal Setting as described herein, R.C.'s improved mobility is shown in FIGS. 61A-61D. As shown therein, there is steady improvement as R.C. started to cover more ground—both offensively and defensively—as the season progressed, with each dot representing an instance of R.C. touching the ball.

Example Embodiments for Data Collection, Analysis, and Presentation

Figure 62:
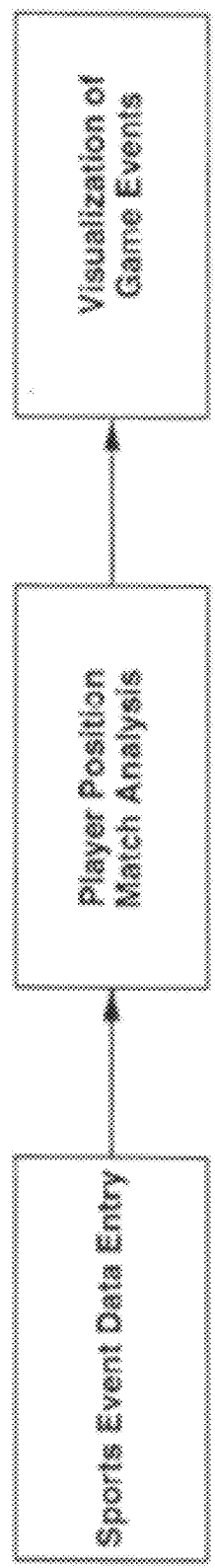
FIG. 62 illustrates an example of data entry, analysis, and presentation of analyzed data, in accordance with the described embodiments.

FIG. 62 shows an example of data entry, analysis, and presentation of analyzed data. As shown therein, the data entry process comprises of collecting general information on the sporting event, the team rosters of the participants and the field locations of all player ball touches as they occur during active play during the game. Data entry can be performed after the sporting event has occurred by viewing a video or in real-time during the event at the stadium. One difference between the two procedures is that the operator must manually increment the game clock during the video viewing data entry procedure. The game clock during real-time data entry is controlled by the computer, as discussed below. Also, the is data collection may be done completely electronically. In that event each player and even the ball may have its own transmitter and the receiver monitors the activity automatically.

Figure 63:
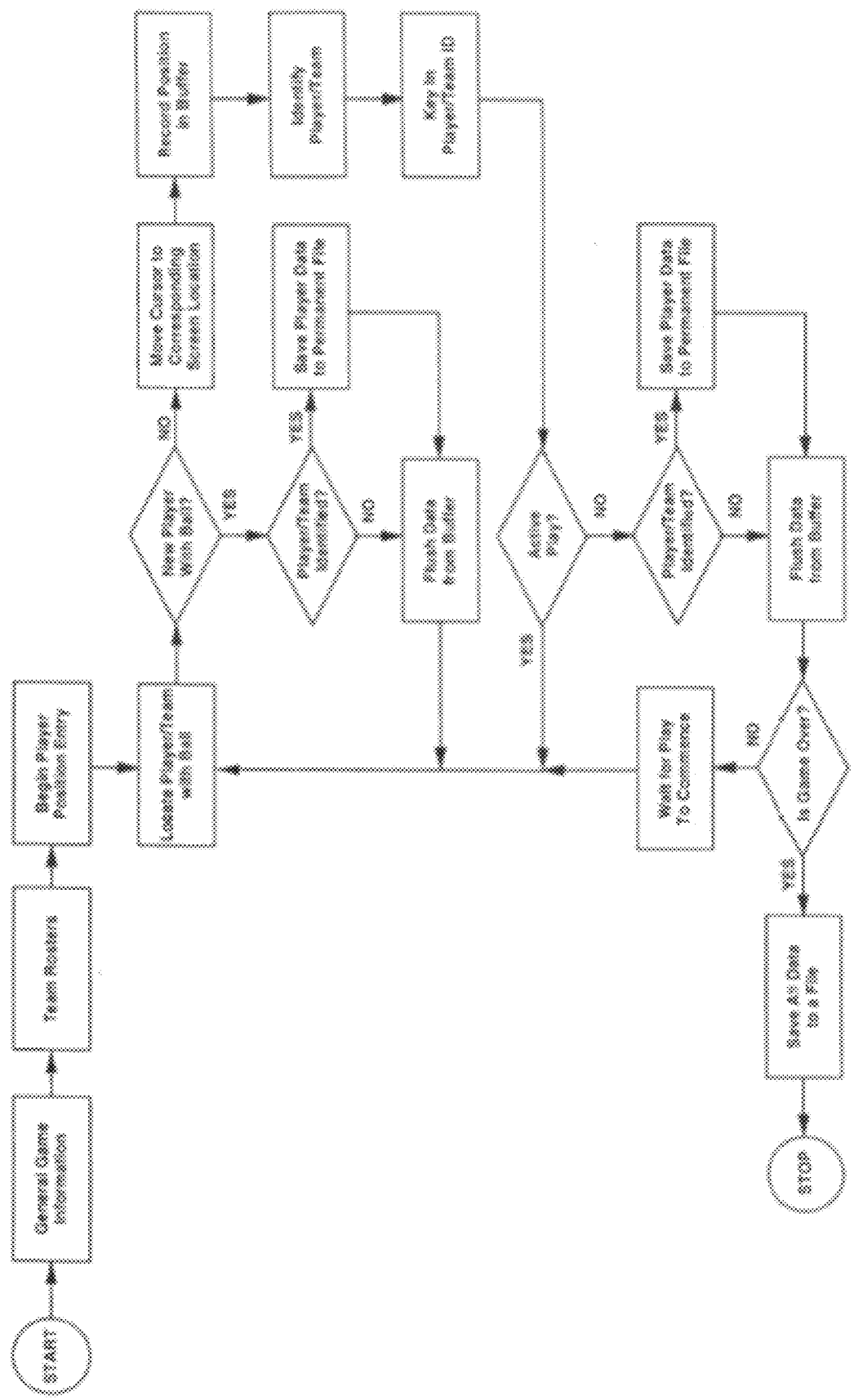
FIG. 63 illustrates a flowchart for an example method of data entry, in accordance with the described embodiments.

In some embodiments, the details of the sporting event data entry process are presented in FIG. 63. The general game information (event description, date, team names, scores, input mode for each team) and team roster information (first, last names, jersey number) are entered before the event commences. This information is entered using standard dialog boxes in the software. The team input mode for each team can be either player level, meaning that each player that touches the ball on the field will be individually identified or team level, where only the team of the player touching the ball is identified. If the input mode is selected to the player level, the positions of each player in the starting lineup are identified and set when the starting rosters of each team are known. The method automatically assigns a key on the computer keyboard in the numeric row (1 to -) to each starting player for the first team and assigns a key in the second row (q to [) to each starting player for the second team. The operator prepares labels with the jersey number of each player and affixes each label to the corresponding key. This is done to identify each player touching the ball during active play. The manipulating software has the capability to add and delete players, modify player positions, and even move them from team to team.

When the input mode is selected to be team level, the method automatically assigns three keys on each row to the unspecified players. In this case, it is not necessary to enter and save the starting lineups. In a real-time situation, player/team field position data is entered when active play commences. At this point, the operator starts the game clock to initiate data entry. When player field position data is entered manually from a video the operator must manually set the clock to the correct time and increment the clock accordingly. Video data entry gives the operator great latitude to set the clock at any time during the sporting event.

Figure 64:
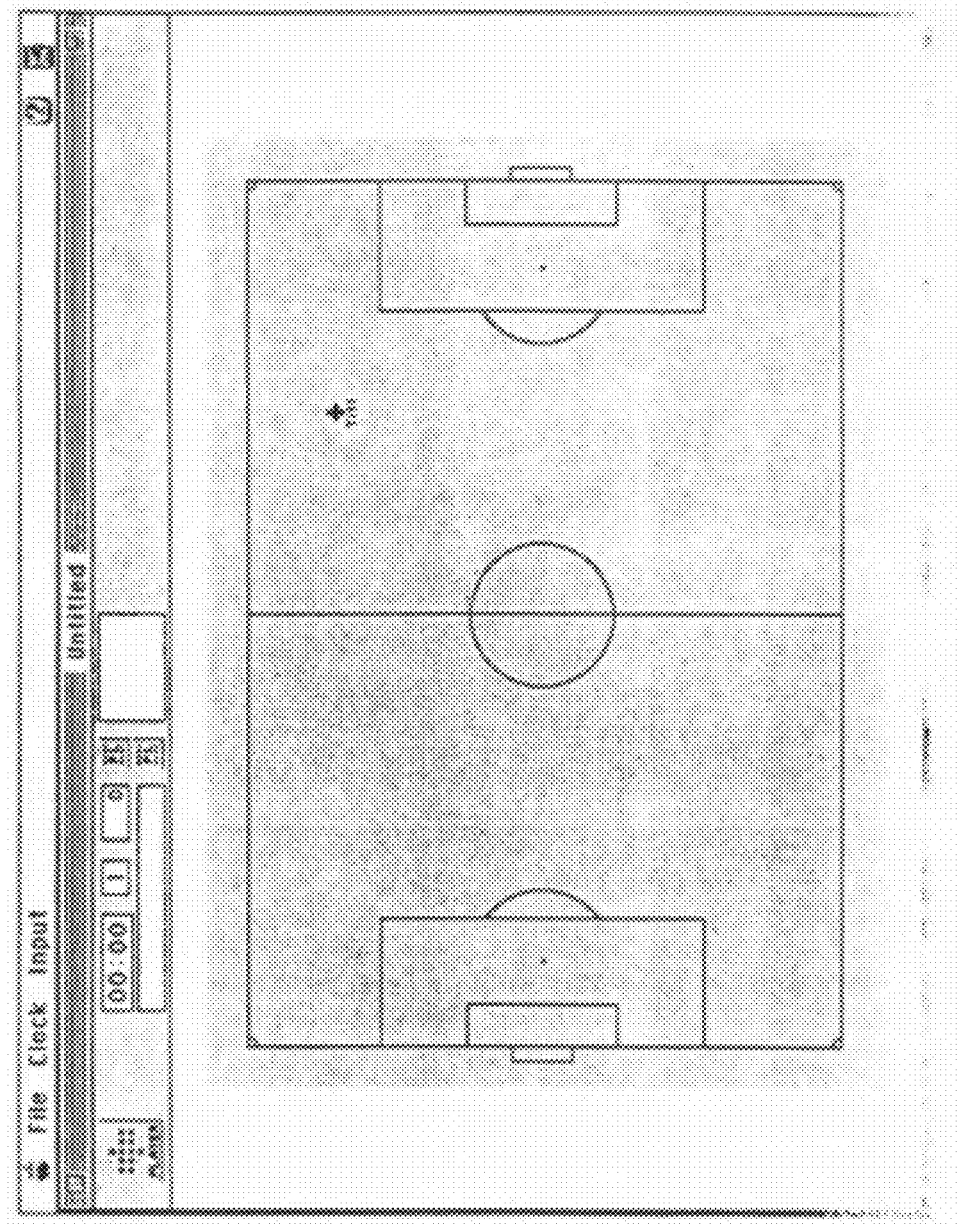
FIG. 64 illustrates an example of a soccer field schematic used for data entry, in accordance with the described embodiments.

The operator utilizes a schematic of the playing field on the computer screen to enter the field position of the player touching the ball. The field schematic is shown in FIG. 64 for a soccer field. Player/team field positions are entered by moving the cursor to the location on the field schematic where the actual player is touching the hall. The location of the cursor on the screen field schematic is determined, converted into field coordinates, and automatically saved at one second intervals. Field coordinates are defined relative to the center of the field, with positive values extending up and to the right and negative values extending down and to the left.

In some embodiments, the process whereby player field position is systematically entered for a period of play proceeds as follows:

When a player receives a ball during active play the operator moves the cursor to the field location on the computer screen where the actual player is touching the ball and depresses the mouse key. This signals that a player/team gained initial hall possession at that particular field location. Once the player is identified the operator depresses the key on the keyboard corresponding to the actual player. The operator continues to move the cursor over the field schematic and keeps the mouse key depressed as the player moves the ball across the field. When the player passes the ball or loses the ball to the opposing team the operator moves the cursor to that point on the field and releases the mouse button. This signals that the player has lost possession of the ball on the field at that location. The operator then moves the cursor freely over the field to the location on the field schematic where the ball is subsequently touched by the next player, depresses the mouse key, and the cycle begins anew.

If the operator fails to identify the player during the time the player possesses the ball, the field position data may not be saved. Player field positions during active play are usually saved only if the player is identified. When active play is momentarily suspended, player field position data entry is likewise suspended. When the period of play is over, the operator stops the clock and saves the data to a tile. The data saved to the file consists of the general match information, the team rosters, including the starting lineup, and a player field position record for each time during active play data was entered. The player field position record consists of a player index, field coordinates where the player touched the ball, and the time in seconds from the start of the period. This is the information utilized by the analysis operation to filter match events from the proceedings.

The function of the analysis operation is to systematically evaluate the player position records saved in the data file against specified criteria and to expose these events to the operator. The current method specifies thirteen different game events for the sport of soccer. Other sports may have different events and different criteria to expose those game events relevant to their particular activities and rules. In any case, the evaluation of the player field position records to expose the specified game events is the same for all events and for all sports.

Figure 65:
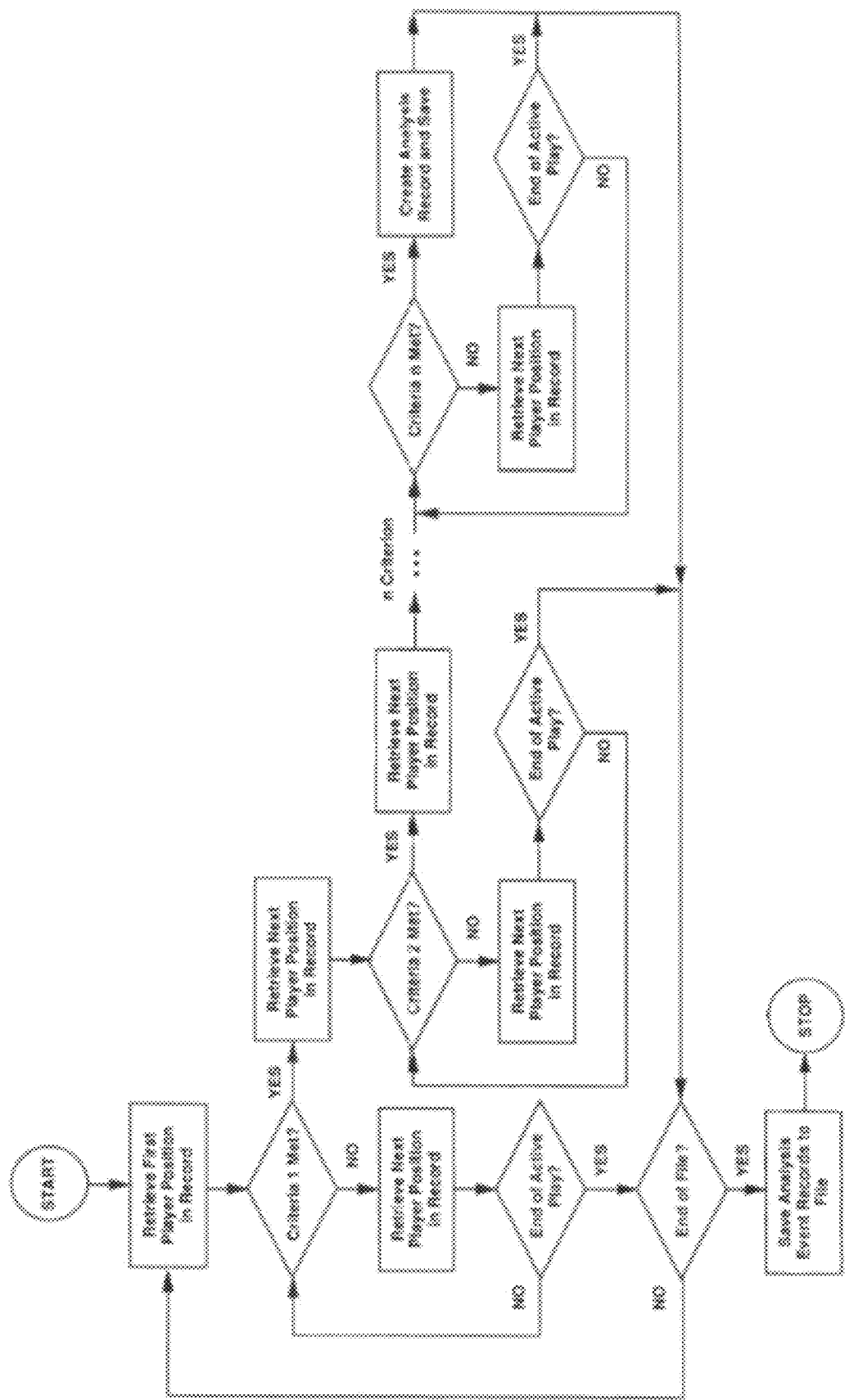
FIG. 65 illustrates a flowchart for a generalization of the analysis process whereby specified game events may be determined from the set of player field position records stored in the data file, in accordance with the described embodiments.

FIG. 65 presents a generalization of the analysis process whereby specified game events may be determined from the set of player field position records stored in the data file. This process is performed automatically for all players on both teams when player level input was specified or for both teams when team level input was specified.

There are two types of analysis event records resulting from the analysis process: field point record and field line record. A field point record specifies the identity of one player, at one field coordinate, at one time during the game. Examples of the field point record for the sport of soccer include the first possession field location, last possession field location, dribbles, and ball touches on the field events. The field line record specifies the identity of two different players, at two field locations, at two different times in the game. Examples of the field line record events include shots on goal, goals, completed passes between team members, lost passes to the opposing team, pass receptions from other team members, pass interceptions from the opposing team, impact passes that lead to a shot on goal, impact passes that lead to a goal, and corner kicks.

The analysis process begins with the first player field position record, which is typically the first ball touch recorded at the beginning of the game and proceeds forward in time to the last record. Each record is evaluated against a set of criteria that is specified for each game event. The first player field position record is evaluated against the first criteria. If it does not pass the test, the next record is examined and so on until a record is found is found that meets the first criteria.

Once the first criteria test is passed, the next record is examined and tested against the second criteria. If it passes the test, the next record is examined and tested against the next criteria. If it does not meet the test, a check is made to determine if there is another record in the very next time slot. If there is, it is examined against the second criteria. This continues until there are no more adjacent records in time, which represents the end of active play during the game. If no records were found to satisfy the second criteria prior to the suspension of play, the process pulls the next record, which will be the first ball touch at the start of active play again. and assess it against the first criteria. If a record is found that satisfies all the specified criteria for a game event, an analysis event record is created. The process continues until all player position records were evaluated for the specified game event. The resulting set of analysis event records is saved to the same data file as the player position records.

Any changes to the team rosters or set of player field records after the analysis is originally performed and the set of analysis event records saved to a file necessitates another analysis evaluation. The software implementation of the method will inform the operator of any changes made to the data file prior to exiting the software so as to provide an opportunity to redo the analysis function. When this analysis process is performed for all specified game events a complete set of game event records is saved to the data file. The next step in the method, the game event visualization operation, utilizes this information to display the visual representation of the analysis results.

The visual presentation of the analysis results is initiated by a query by the operator. The software implementation presents a menu upon which all game events are listed. The operator selects the event of interest, and the software presents a dialog that requests the identity of the team or player and the time interval during the game. Once these selections are made and the operator initiates the query, the software implementation immediately pulls all records of the specified game event. A linear search for the specified player/team and time is conducted through this set of records. All records that meet the player and time criteria are sent to the game event visualization routine.

Figure 66:
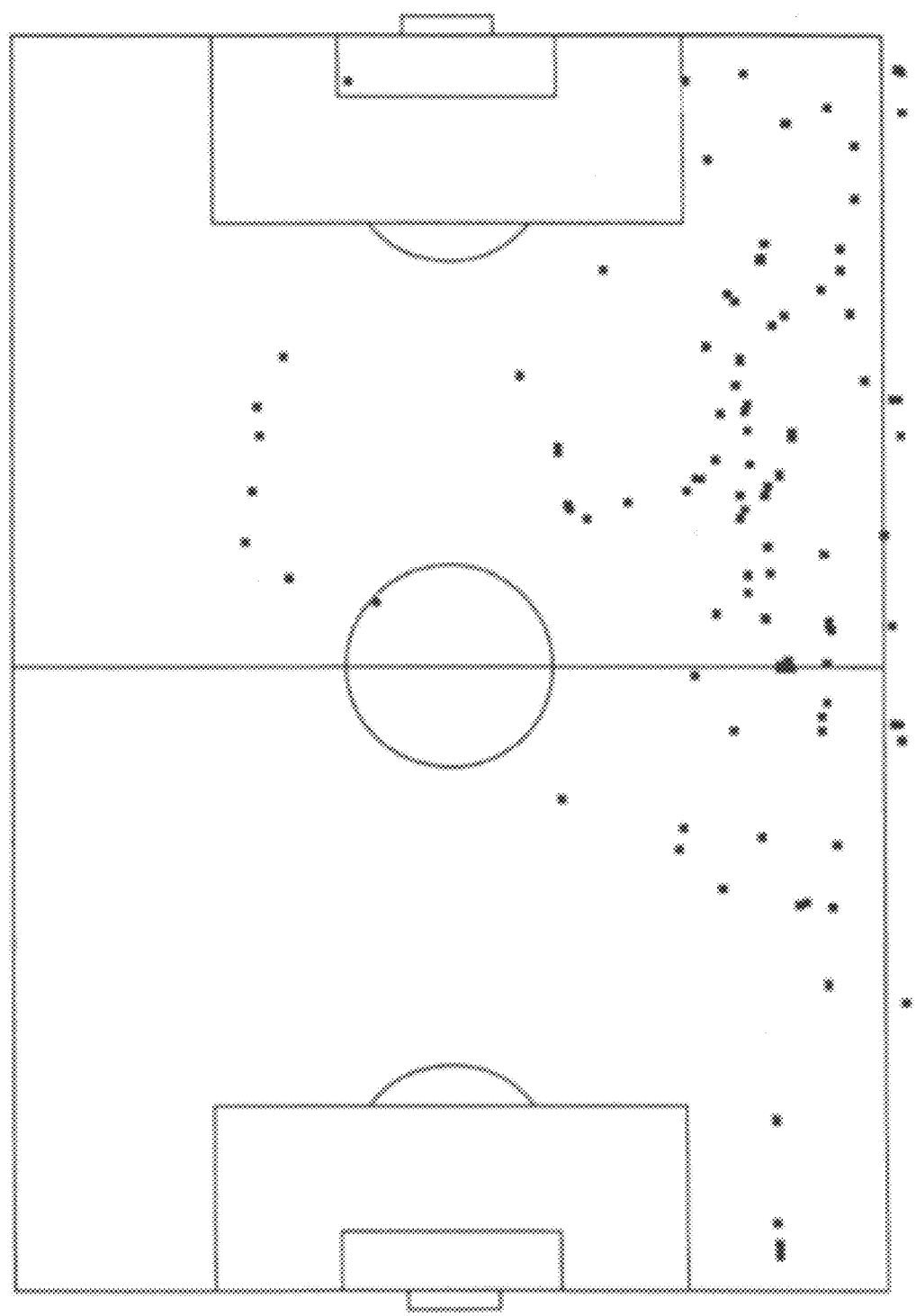
FIGS. 66 and 67 illustrate examples of a field point record and field line record, respectively, in accordance with the described embodiments.

As noted earlier, there are two types of analysis results, the field point and field line records. Both are visually presented to the operator in the same manner: the set of all results are plotted at the location on the field where the event actually occurred during the game. The field point record is plotted at its specified field coordinate, as shown in FIG. 66. The field line record, which consists of two individual point records, plots each record at its specified field coordinate. These two points are joined by a line to indicate the movement of the ball between them.

Figure 67:

Two different symbols are used to designate each team. The field line record, as shown in FIG. 67, draws the symbol as a solid at the start of the play and clear at the end of the play, thereby illustrating the movement of the ball between the players. When the full set of analysis results are plotted together in this manner the trends of play for the team or player in question are exposed in such a visual manner as to be easily understood and intuitive.

Figure 68:
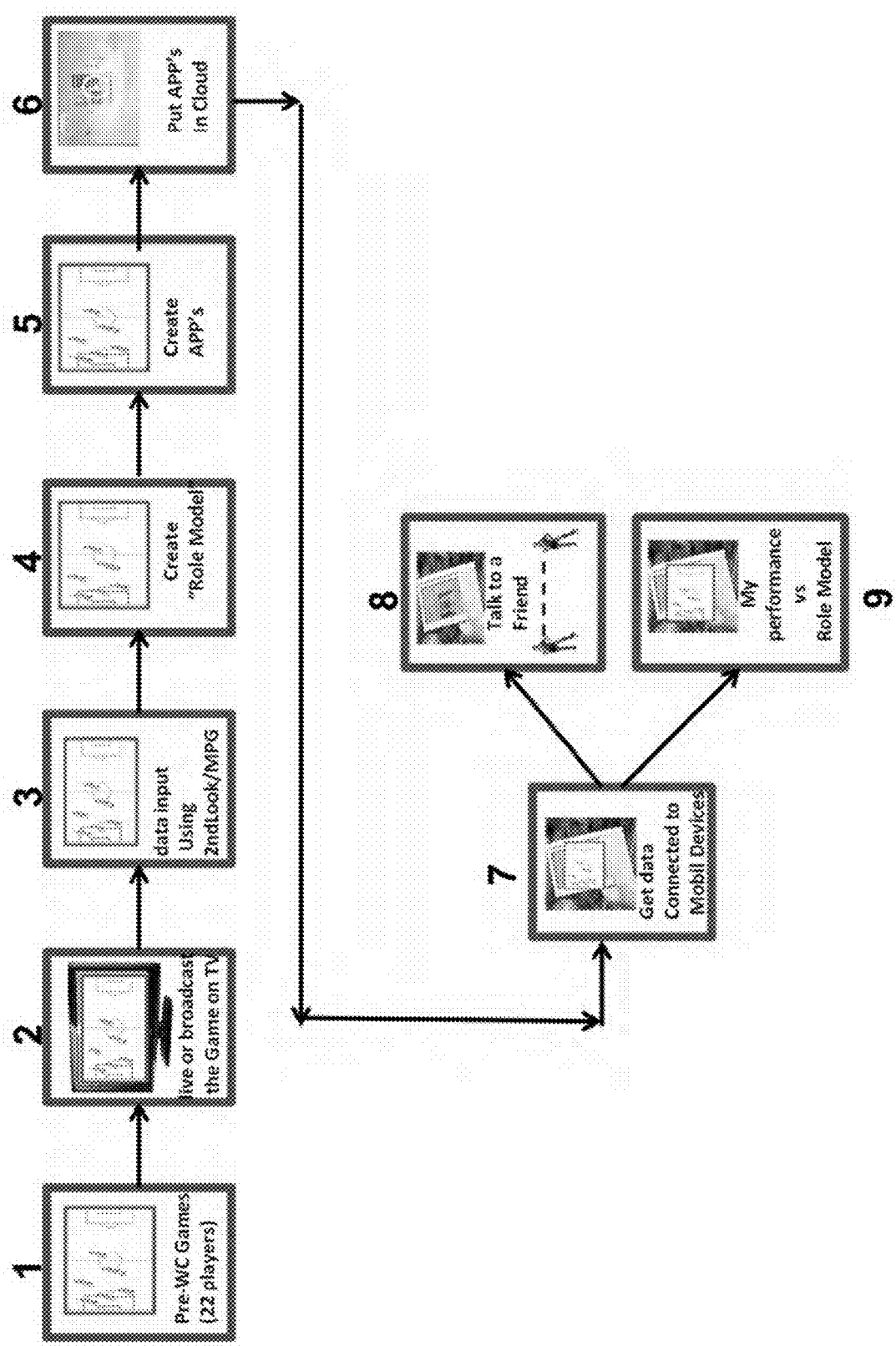
FIG. 68 illustrates different aspects of a cloud-based application that implements one or more embodiments of the disclosed technology.

In some embodiments, the described embodiments may be implemented using one or more software applications. FIG. 68 shows an example of how such applications can be used. As shown therein, blocks 1 through 4 in FIG. 68 include operations that can be performed by the developer of the training program. In block 5, software applications for public dissemination are developed. Such applications can utilize cloud services for storage, retrieval, and even computations, as illustrated in block 6 of FIG. 68. Additionally, or alternatively, the applications may use local resources. In block 7 of FIG. 68, the applications on a user's device (e.g., laptop, tablet, smart phone, etc.) are used to receive instructions, goals, and feedback, as well as allow a user to track a player movements and log important performance milestones.

Figure 69:
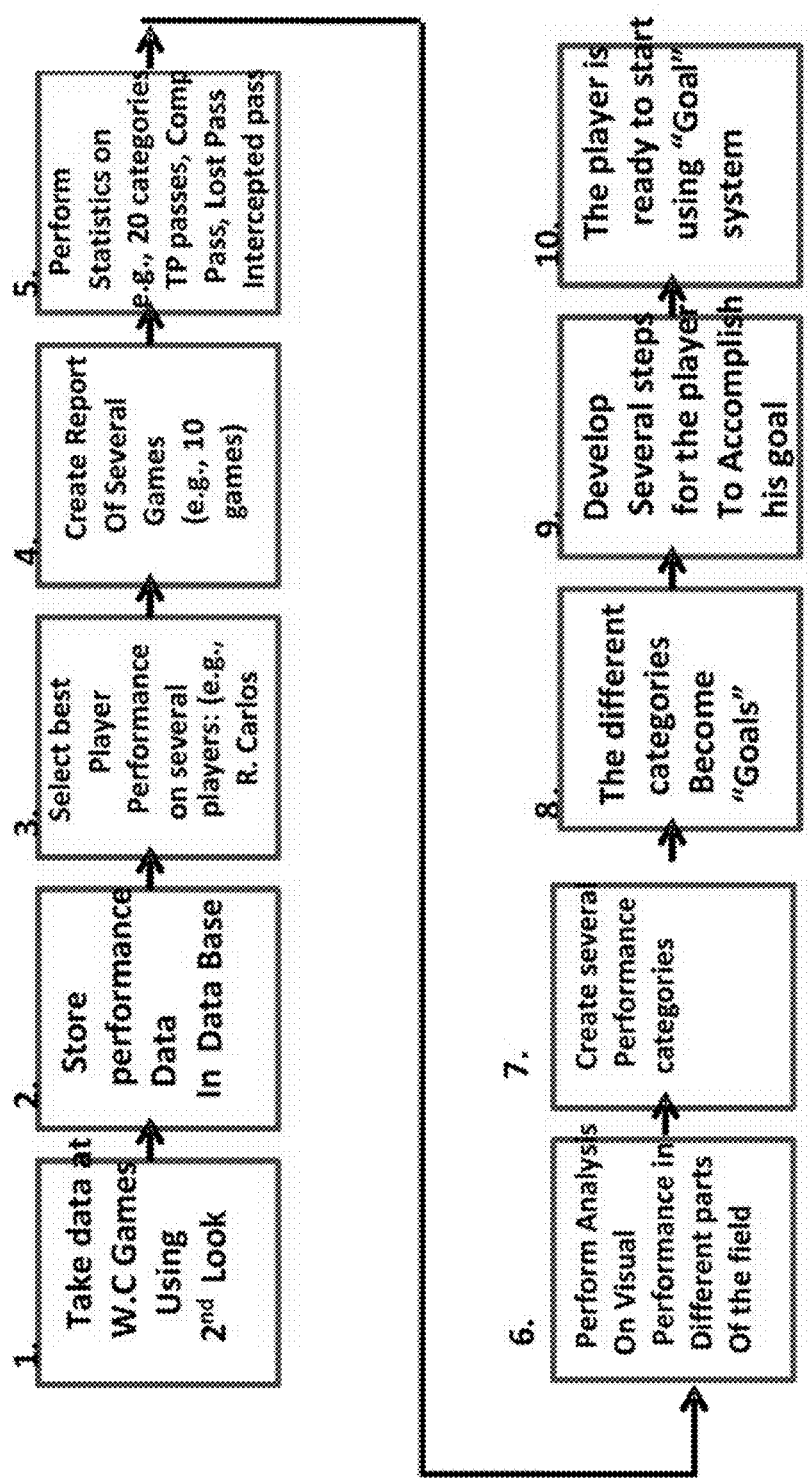
FIG. 69 illustrates a flowchart of an example method that can be performed prior to using the goal system, in accordance with the described embodiments.

FIG. 69 illustrates another example set of operations that can be carried out prior to a player using the goal system of the described embodiments for enhancing his/her skills.

As previously discussed, the described embodiments use collected data associated with the best players in the world to create a Role Model, which can be used as a standard to set goals for a player, against which the player can assess his/her performance during practice or actual games. The data associated with the role model can be used at different levels and at varying degrees. For example, goal scoring characteristics of the role model can be used to set goals for an advanced player, which perhaps only lacks goal scoring prowess, whereas offensive movements of the role model can be used to set goals for a player that intends to improve his offensive movements. As such, the performance of each role model is broken down into many categories for each position on the field, and a list of priorities is created based on the job required by the player position and team system of play. Each of these elements can become the goal. As noted earlier, this process is referred to determining the DNA (e.g., the fundamental characteristics) of soccer as obtained from best players in the world, and creating the role models, which become standards for comparison of players' performance.

In some embodiments, the player's performance is then captured using different tools, such as MPG, which allows real-time (or near real-time) capture. For example, a parent of a young soccer player can stand on the sidelines and, using his/her touch screen record completed passes, corner kicks, goals scored, etc., by the young soccer player. The display on the touch screen can, for example, include specific fields (or buttons) for each action (e.g., corner kick) that are incremented if touched. Additionally, the touch screen can allow the user to, for example, draw a line (or starting and end points of a line) that correspond to a completed pass made by the player. Using such a tool, the feedback can be provided immediately (or during half-time) to the player/coach, as to whether or not a player is meeting his/her performance goals.

In addition, the described embodiments can be used for decision making using weight and grades that can be produced from comparing the performance of players with their Role Models. By assigning a grade to each player's performance (e.g., how well the player met his/her goals, the level of difficulty of goals, etc.), the coach can establish rankings and understand the individual player's performance as compared to other players on the team to determine who should play, start, etc. In some embodiments, a player's value can also be provided to outside entities, which may be interested in signing contracts with, or trading for, a player. The grades can be tabulated based on a Composite Performance Index (CPI), which is based on a player's performance multiplied by the weight of each goal for all the player goals.

Embodiments of the disclosed technology provide a standardized mechanism for objective assessment of a player to allow a team to replace an existing player (e.g., acquire a 'cheaper' player to replace an existing 'expensive' player on their roster with the same skills), or to assess the team's shortcomings and to search for players that can cover those shortcomings.

The tracking of a player performance can be additionally, or alternatively, accomplished using non-real-time tools, such as Second Look™, which allows data collection on the performance of each player on the team (or the opposing team) at a later time based on, for example, viewing of a video recording. The collected information can be used, as noted earlier, to assess the goals.

Example Embodiments Using the Spine and Pass-Distribution Matrix

Figure 70B:
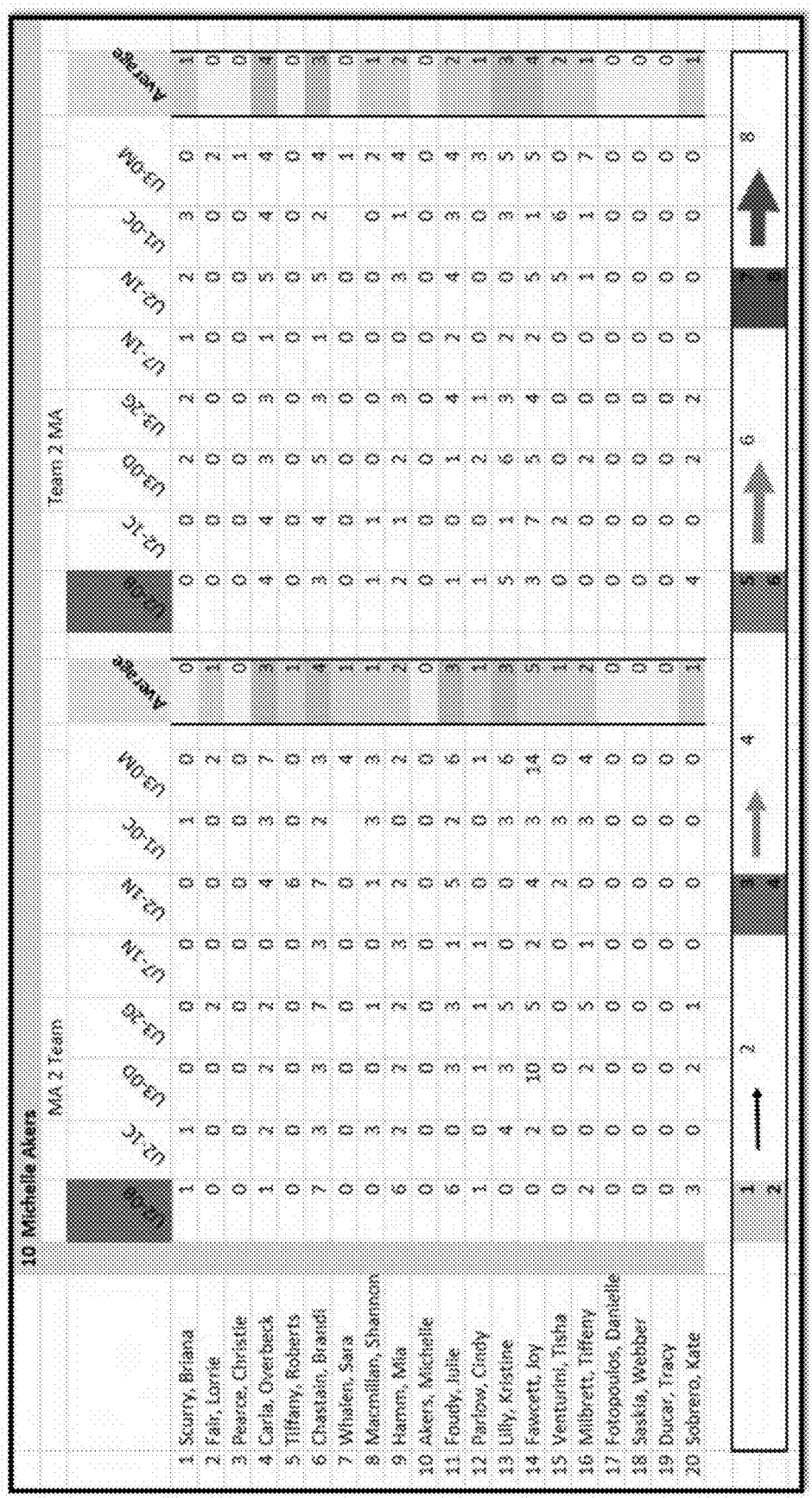
Figures 70C, 70D:
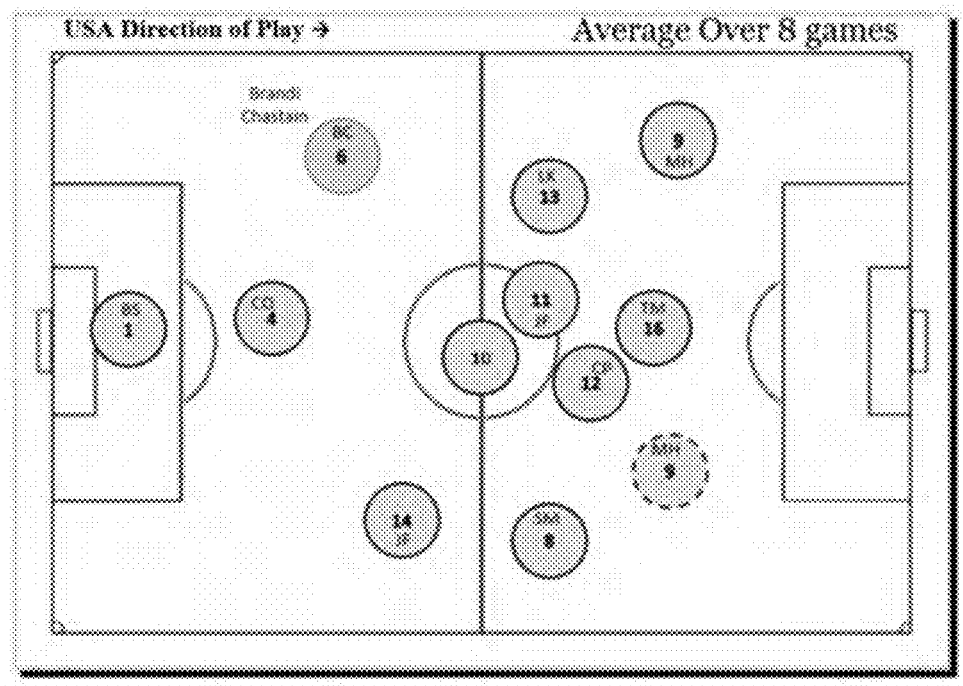
Figure 70E:
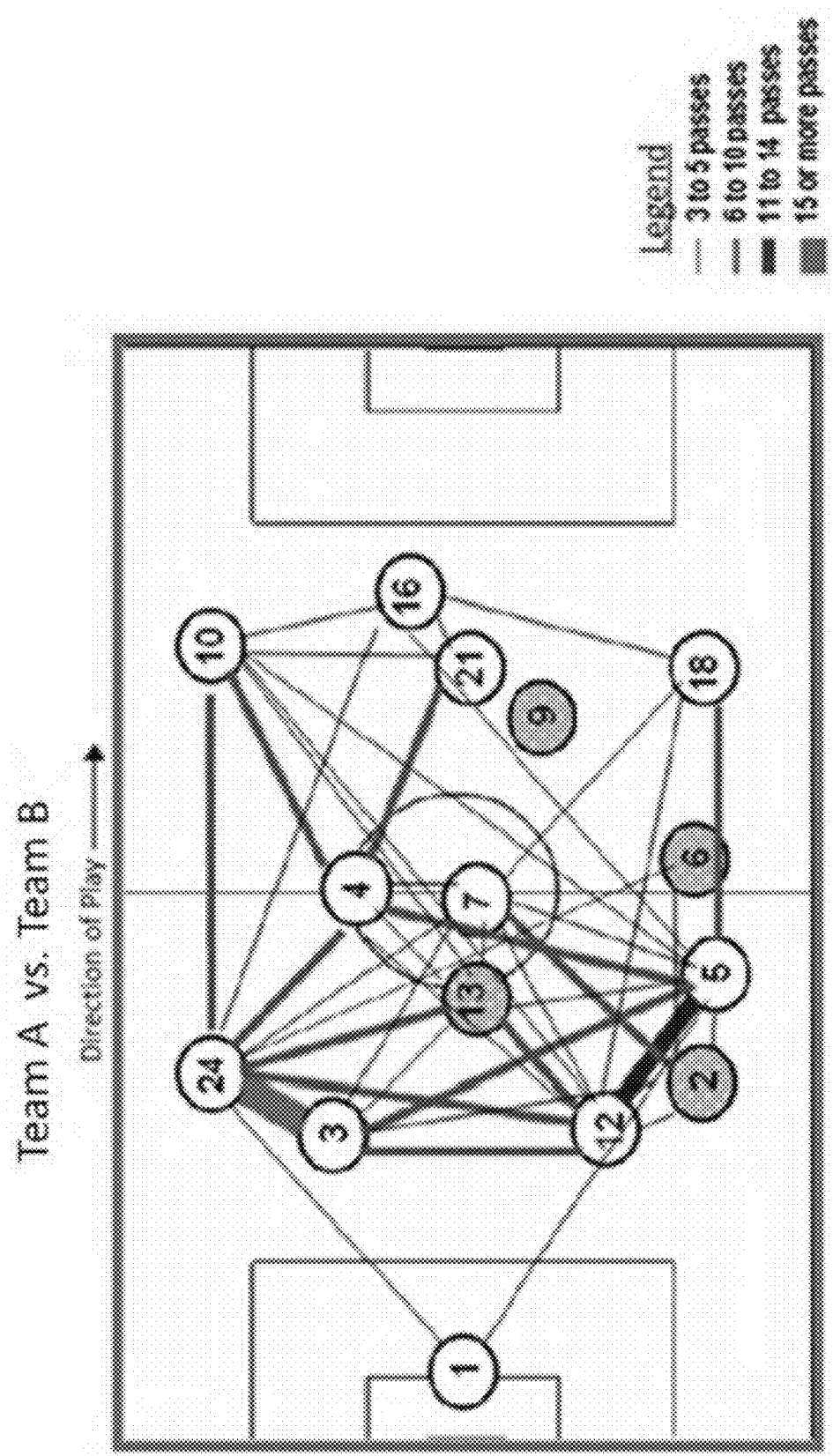
Figure 70F:
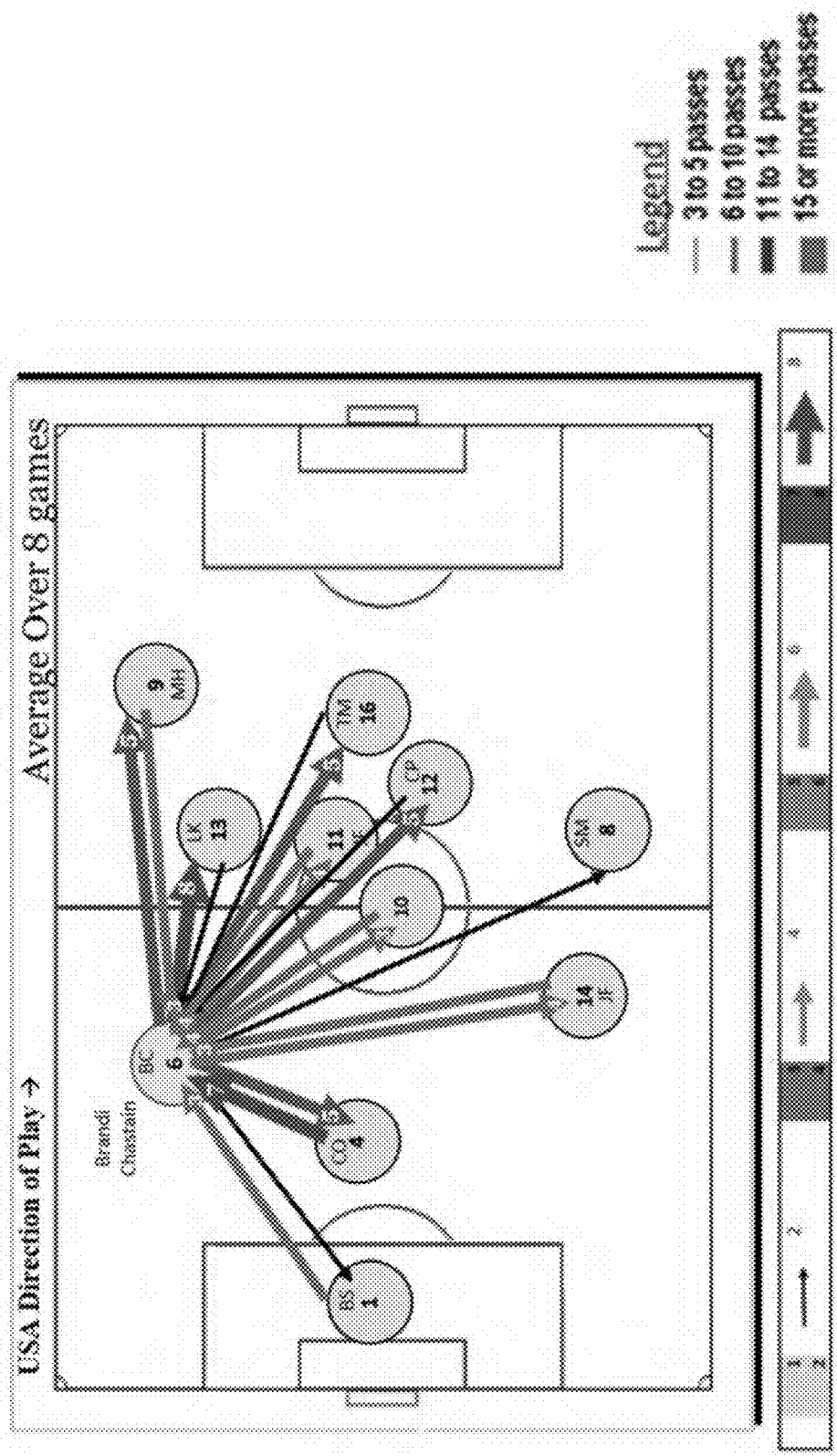

In some embodiments, the spine and the pass-distribution matrix for team and the individual player can be used to analyze how the team players are connecting (or not connecting) during the game and within which area of the field. The results can be produced in a visual overlay on top of the field. This information gives the coach a major advantage in understanding what is happening on the field and how to play the opponent. For example, it can be used for scouting purposes to assess the opponent's strength and weaknesses, and help in decision making for tactical and strategic purposes. FIGS. 70A through 70F illustrate steps 1 through 4 for providing a spine and pass distribution matrix, in accordance with the described embodiments. In step 1, data collected for team players using, for example, the Second Look™ software (e.g., as shown in FIG. 70A). The collected data in step 1 may not be in the correct format and may include many extra information that is not readily usable by the coach/player. In step 2, the collected data is exported into a utility that can allow manipulation of data (e.g., as shown in FIG. 70B) according to specific algorithms that are developed to enable the disclosed embodiments. Examples of the exported data include, but are not limited to, images of completed passes, pass-distribution matrices for a specific number of games, and data that can be used to generate completed pass overlays and centers of gravity for specific players. In step 3, the manipulated data is presented in format that can be readily used in step 4. In a non-limiting example, the data produced in step 3 can provide a sorted visual representation of the total completed passes (or pass distribution) between players (e.g., as shown in FIG. 70D). For example, both the visual representation of the completed passes along with the pass-distribution matrix in step 3 illustrate the total and/or average number of completed passes between players, as well as how many completed passes there were and where on the field they occurred. As another example, the centers for each player can be represented as shown in FIG. 70C. In step 4, the data produced in step 3 is graphically presented (e.g., as shown in FIGS. 70E and 70F). The "spine" that is presented in step 4 can, for example, show where on the field the completed passes took place. The change in thickness and/or color of the connecting lines (i.e., the pass distribution), based on the number of competed passes, show the connectivity (or lack of connectivity) between the players during the game.

Figure 71A:
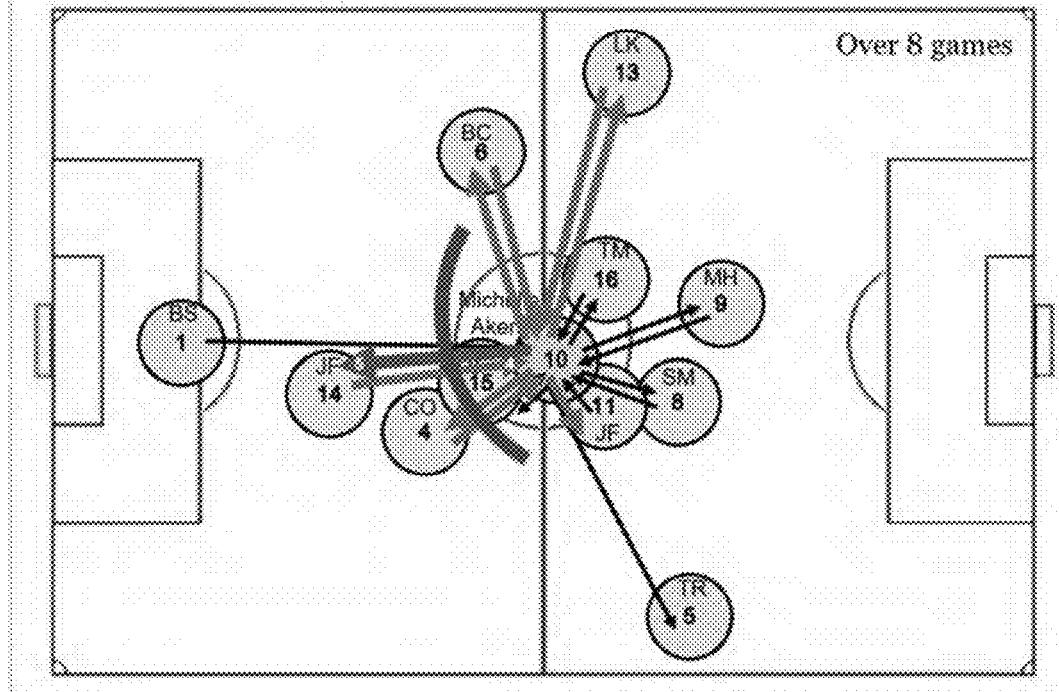
FIGS. 71A and 71B illustrate examples of applying the spine and pass distribution analysis for team and individual goals, in accordance with the described embodiments.
Figure 71B:
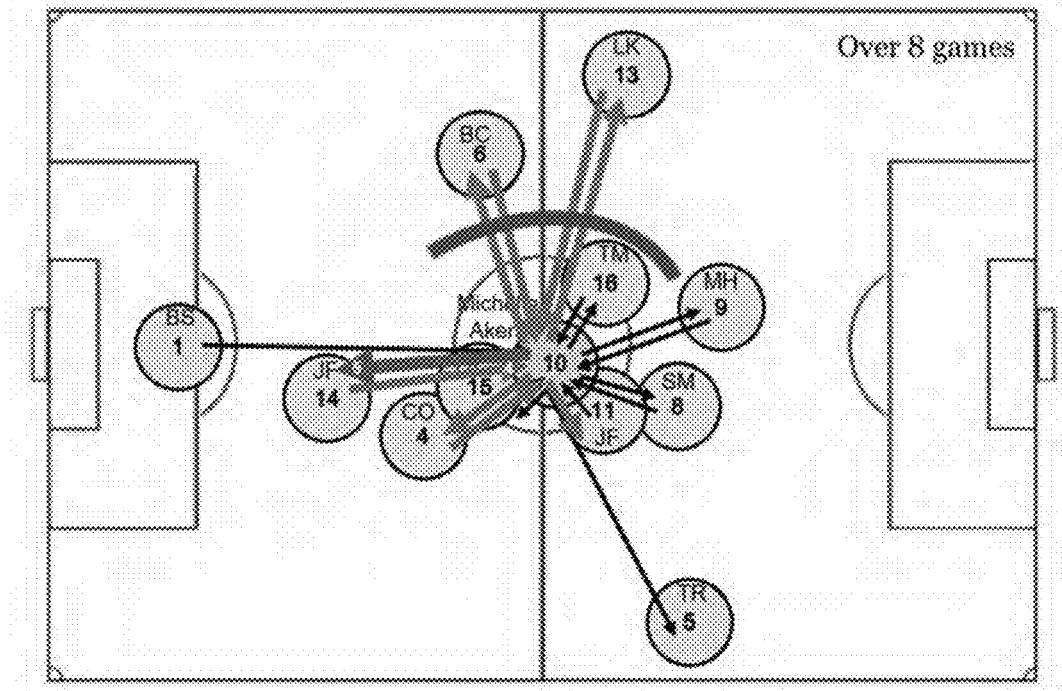

The spine produced in accordance with the disclosed embodiments can visually and immediately identify and improve team tactics and efficiencies. In particular, we can see how individual players connect or not connect with other teammates on the field. Therefore, the disclosed embodiments can be used to not only improve and perfect the skills and performance of an individual player, but can further be used to assess the team's overall performance against individual player's goals, to change the goals of individual players to fit the overall team tactic and strategy. FIGS. 71A and 71B provide examples to illustrate this concept. After making adjustments, data can be collected (both for individual players and to provide team spine) to assess how the change in strategy affected coverage, flow, and results of the game. The examples illustrated herein show how individual goals, role models and spines can be combined with setting tactics and strategy that impact the team's performance as well as helps the coach and/or team block the opponents from winning the game.

The example of the "spine" in FIGS. 71A and 71B illustrate how M. Akers played with her teammates over eight games. The pictorial view shows where she played, who she connected with most, how her teammates played with her, as well as provide an opponent a way to block and/or stop her play. In the example shown in FIG. 71A, the spine and completed pass show a trend for M. Akers: most of her passes were back passes with very few passes forward to her teammates. M. Akers does not play on the wings because her teammates (#6 BC & #14 JF) play on either side of her. Her teammates tend to feed her more balls than she feeds them. Thus, a tactical and strategic decision can be made to block (red curved line) her from passing back to JF, player #14 and CO, player #4, which will in turn break the team spine and give the opponent the chance to score and win.

In the example shown in FIG. 71B, the spine, coupled with M. Akers intercepted passes report, show that she did intercept the majority of the opponents kicks that were directed on the goal (e.g., shots on goal by the other team, which were kicks that propelled the ball toward the goal but were intercepted by M. Akers). This is likely due to the fact that the opponent's goalkeeper was blocked in during the game on both sides (probably by Mia Hamm) and so the goalkeeper was forced to kick her goal kicks down the center of the field, where M. Aker played. Therefore, M. Akers was able to intercept the majority of the goalkeeper's kicks. Over eight games M. Akers took 12 shots on goal, had 3 goals, had 14 impact passes that resulted in shots on goal and 1 assist. When M. Akers makes her own plays, she does better than setting them up for her teammates.

The insight provided by the disclosed embodiments and the illustrations of FIGS. 71A and 71B indicate that when M. Akers tries to do the job of a midfielder and be a "feeder" player by passing the ball forward to her teammates, she loses the ball. But when she takes the ball up the field herself, then she becomes an "impactful" player. Consequently, a tactical and strategic decision can be made by the opponent to block her (red arc in FIG. 71B) from going forward, or passing balls to player #6 (BC) and #13 (LK), which will in turn break the team spine giving the opponent the chance to score and win.

Figure 72:
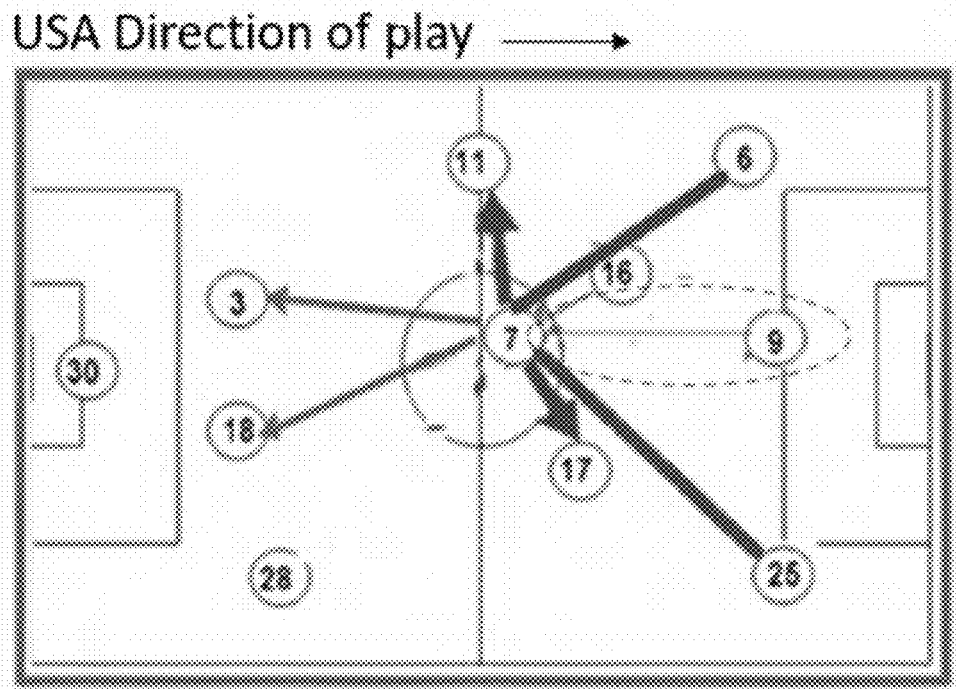
FIG. 72 illustrates another example of applying the spine and pass distribution analysis for team and individual goals, in accordance with the described embodiments.
Figure 72:
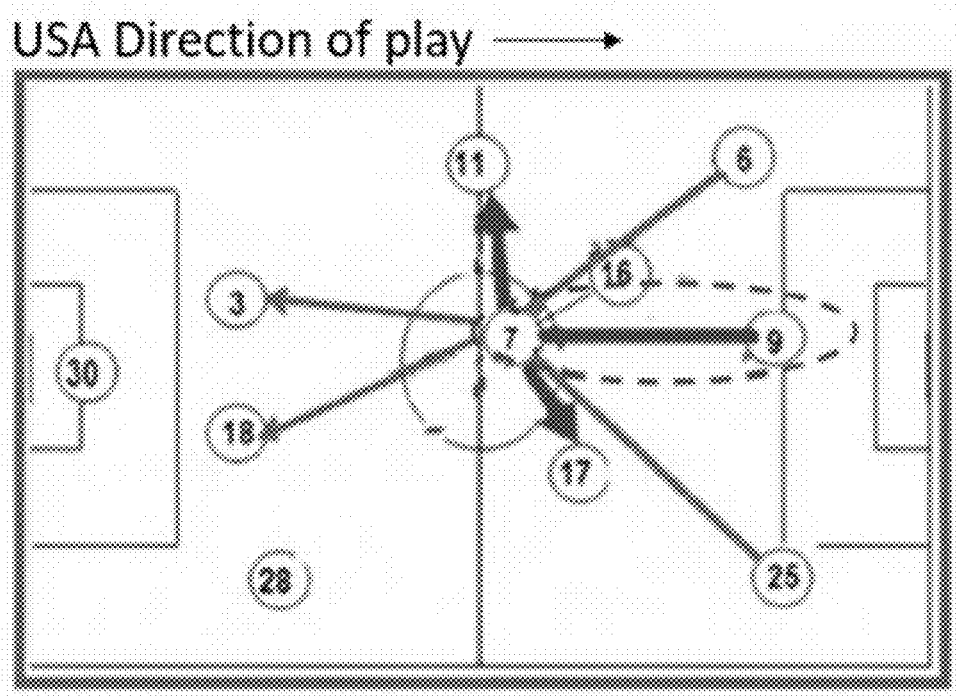

FIG. 72 illustrates another example scenario in which the spine and individual goals can be combined in accordance with the disclosed embodiments. The top section of FIG. 72 shows that player #7 was unable to make any completed passes to player #9 in the scoring box (dashed oval). It was observed, however, that player #7's role model performed a few passes into the scoring box. player #7's inability to connect with player #9 did not satisfy the coaching and team requirements of tactics and strategies per player #7's Role Model of 8 passes into the scoring box. This shortcoming was remedied by providing a new goal for player #7 which was to connect with player #9 by making=8 passes into the scoring box, as shown in the bottom diagram of FIG. 72 (dashed oval). The shortcoming was remedied, and the number of passes between player #7 and player #9 increased, as illustrated by the increased thickness of the blue line connecting player #7 and player #9.

Thus, the spine diagrams that are produced in accordance with the described embodiments provide an effective tool for quickly assessing deficiencies and strengths of the team (this includes the opposing team), and to determine if an individual player has met his/her goals, and whether or not the individual's goals (even if successfully performed) require further adjustments to improve the overall tactics of the team.

FIG. 73A-73F illustrate an example of applying the spine and pass distribution analysis to the Brazilian soccer team in the Brazil vs. Turkey match in the 2002 World Cup.

Figure 73A:
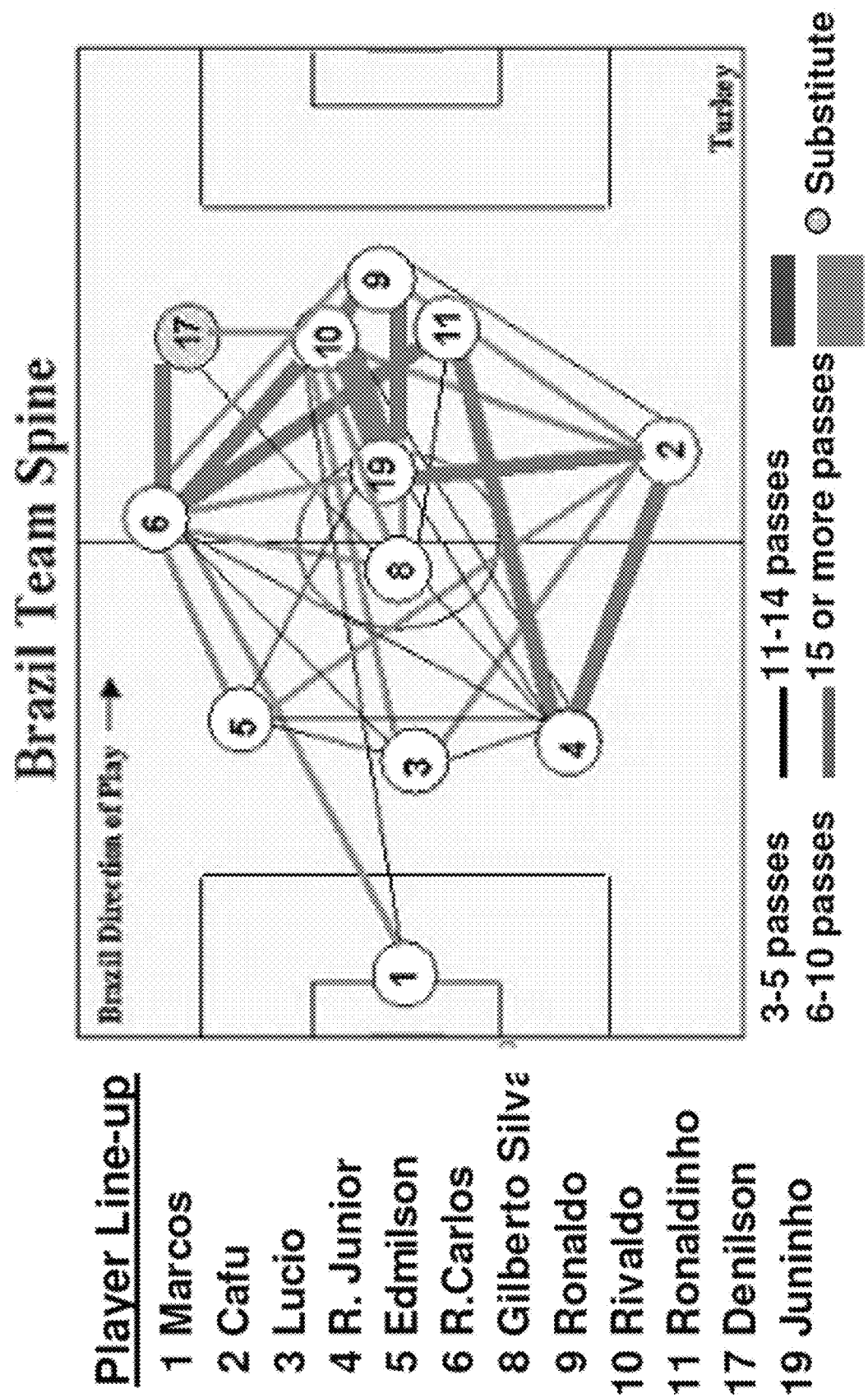
FIG. 73A-73F illustrate yet another example of applying the spine and pass distribution analysis for team and individual goals, in accordance with the described embodiments.

FIG. 73A shows the spine of the Brazilian team. As shown therein, there were frequent connections between Juninho (19) in the midfield and Rivaldo (10) and Ronaldo (9) in the attacking area. Juninho in turn was receiving passes from Cafu (2) on the right flank. There were also frequent connections between Rivaldo (10) and Ronaldo (9), indicating close collaborations between the two forwards. However, neither Rivaldo nor Ronaldo connected much with Ronaldinho (11). Instead, Ronaldinho was connecting with Roberto Carlos (6) on the left flank and Roque Junior (4) from the backfield.

Figure 73B:
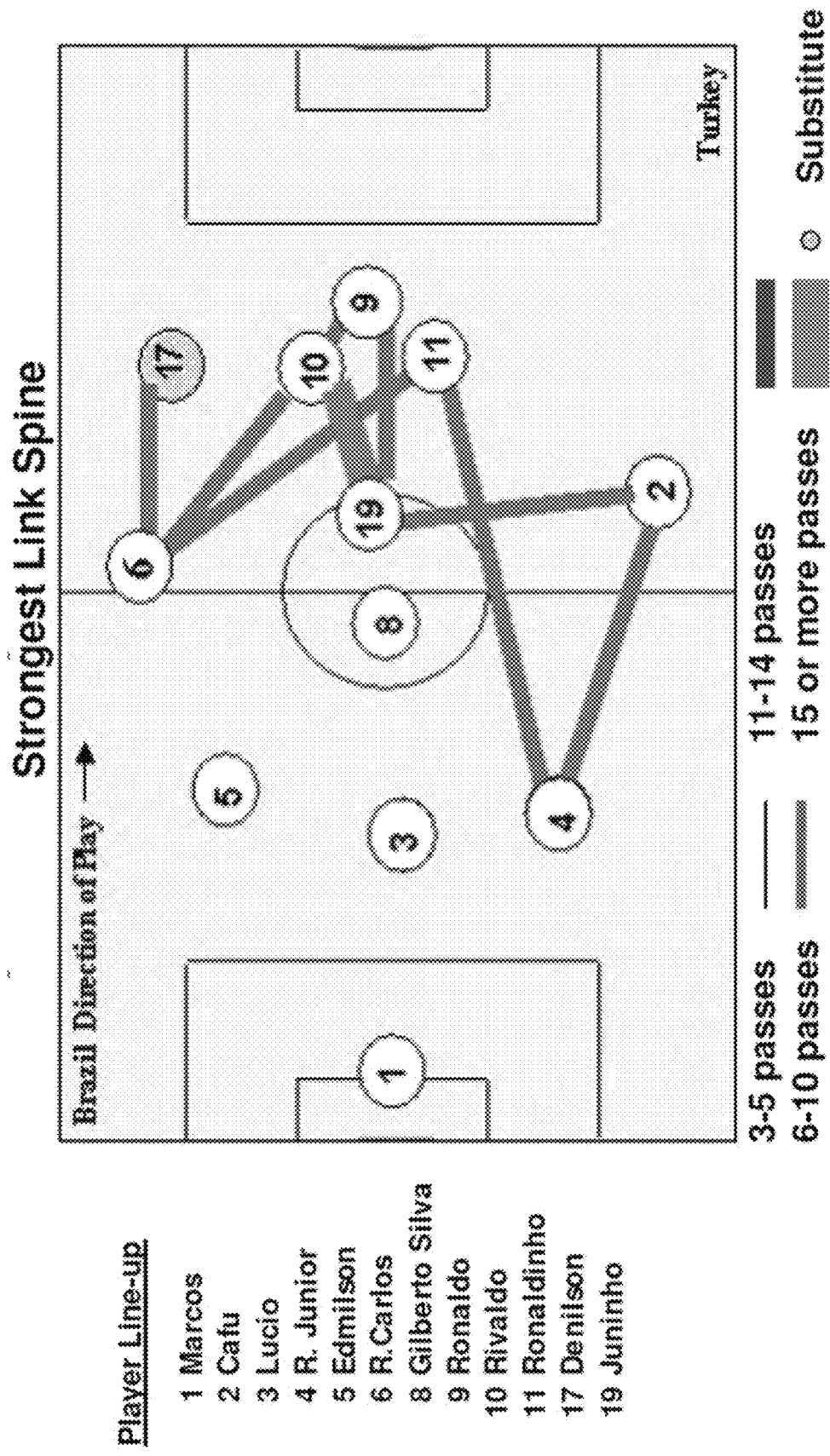

FIG. 73B shows the strongest spine of the Brazilian team, wherein Brazil plays with three defenders, four midfielders and three attacking players. Roberto Carlos (6) and Cafu (2) attacked from the sides and try to pass the ball into the middle. We can see that Roberto Carlos connected with Ronaldinho (11) and Rivaldo (10), but he did not connect with Ronaldo (9) or Juninho (19). Cafu (2) fed the balls to Juninho (19) from the right side. Juninho distributed the balls to Rivaldo (10) and Ronoldo (9). However, he did not connect with Ronaldinho (11). Brazil substituted Denilson (17) in the second half, around 65 to 70 minutes into the game. His job was to attack aggressively with very forward positioning. There were many connections between Rivaldo (10) and Ronaldo (9) indicating many give-and-go combinations.

Figure 73C:
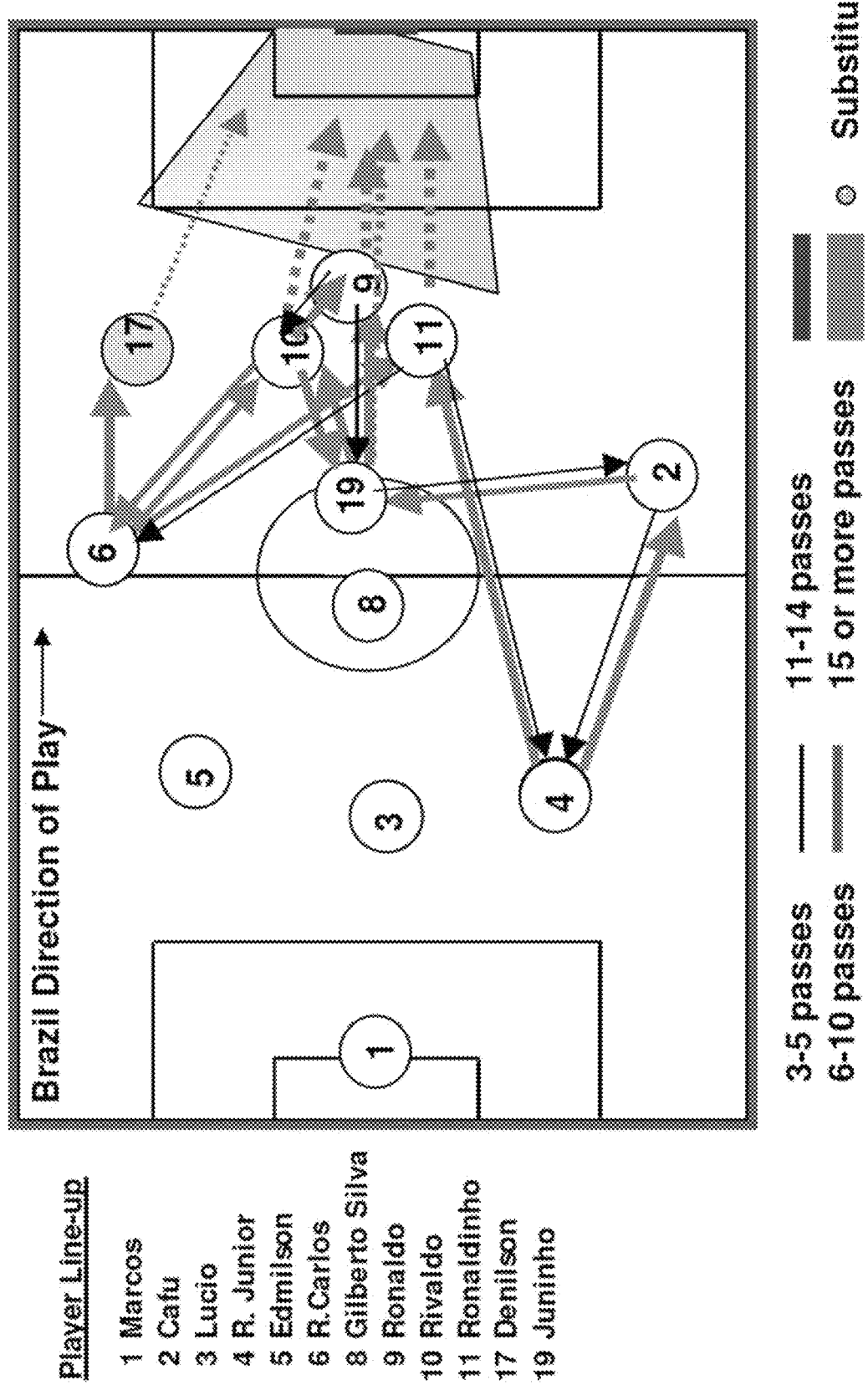

FIG. 73C shows how Brazil shot the ball. As shown therein, many balls went to the attacking players in the center that resulted in shots taken from the middle. Many shots were taken from long-distance outside of the penalty area. Ronaldo (9) had six shots, Rivaldo (10) had 5 shots, and Ronaldinho (11) had 3 shots.

Figure 73D:
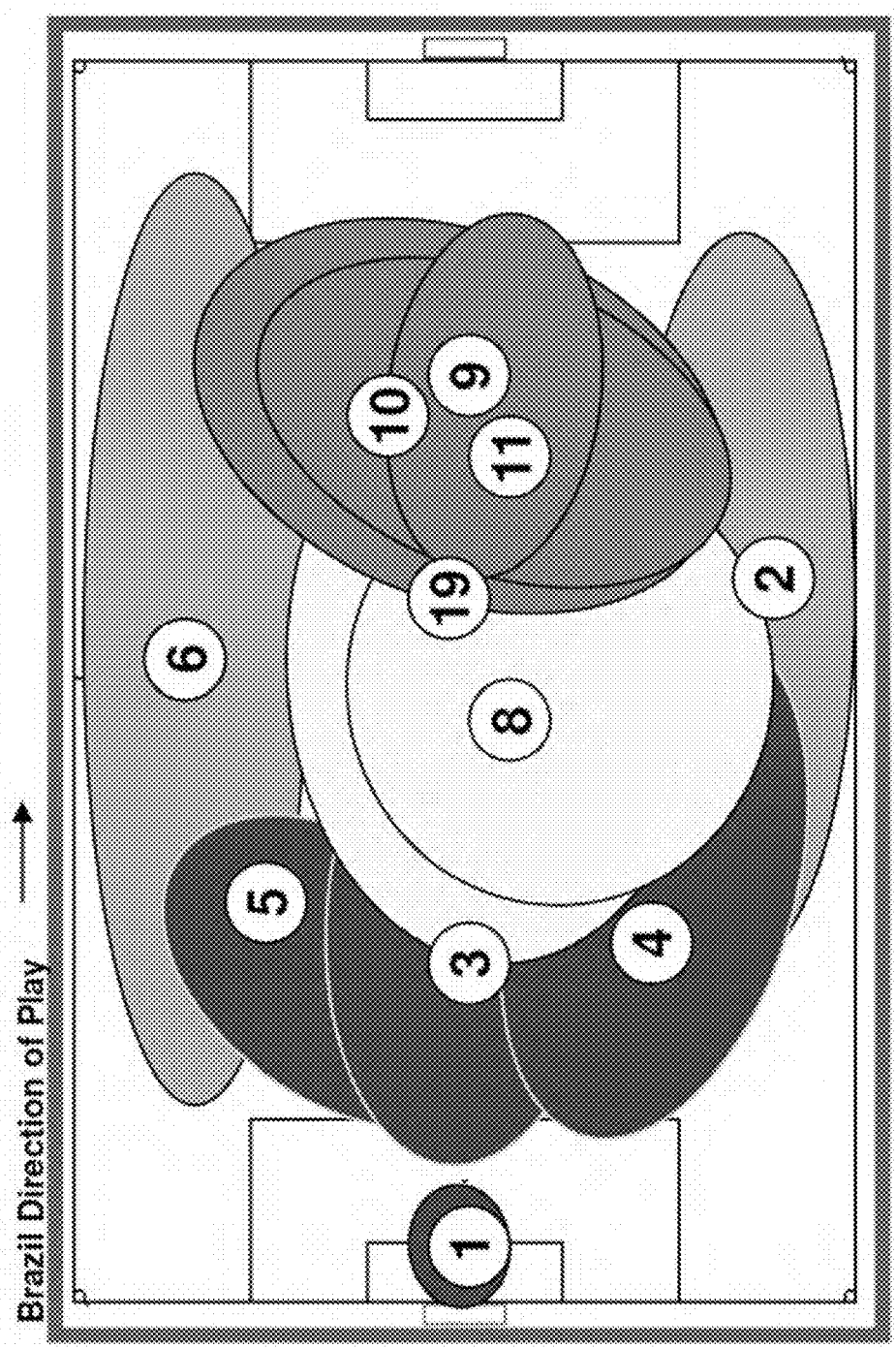

FIG. 73D shows the primary playing area (PPA) for the Brazilian soccer team.

Figure 73E:
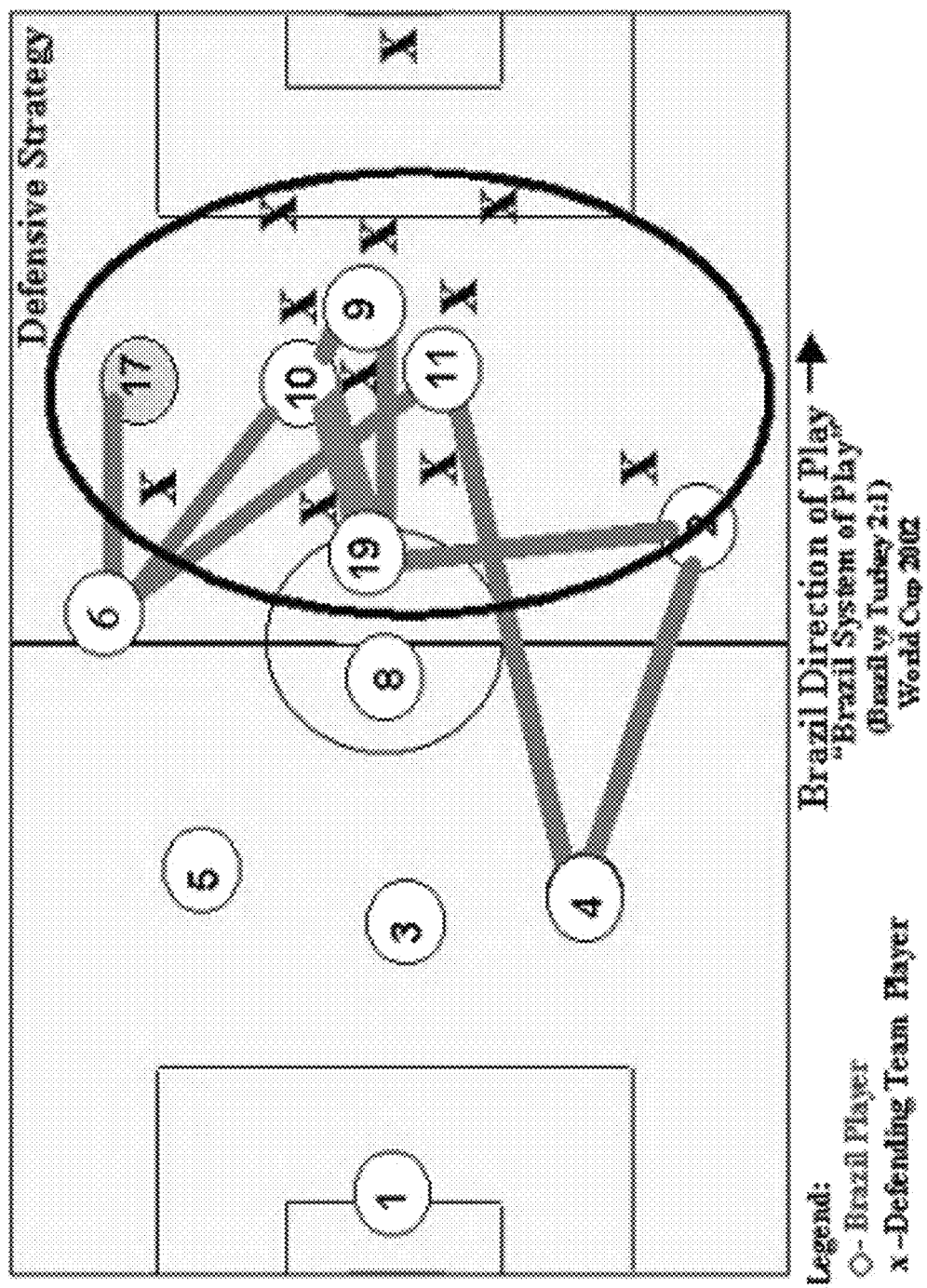

FIG. 73E shows an example of how to defend against Brazil. As shown therein, the opposing team could assign one player to guard against each of the following Brazilian players: 6, 19, 2, 10, 11, and 9. Add one more defensive players to help guard against Ronaldinho (19) and cut off the connection between him and the three attacking players. Add one more defensive players to guard against Rivaldo (10) and try to interrupt the connections among the three attacking players. Put two more defensive players on the side of the penalty box for added security.

Figure 73F:
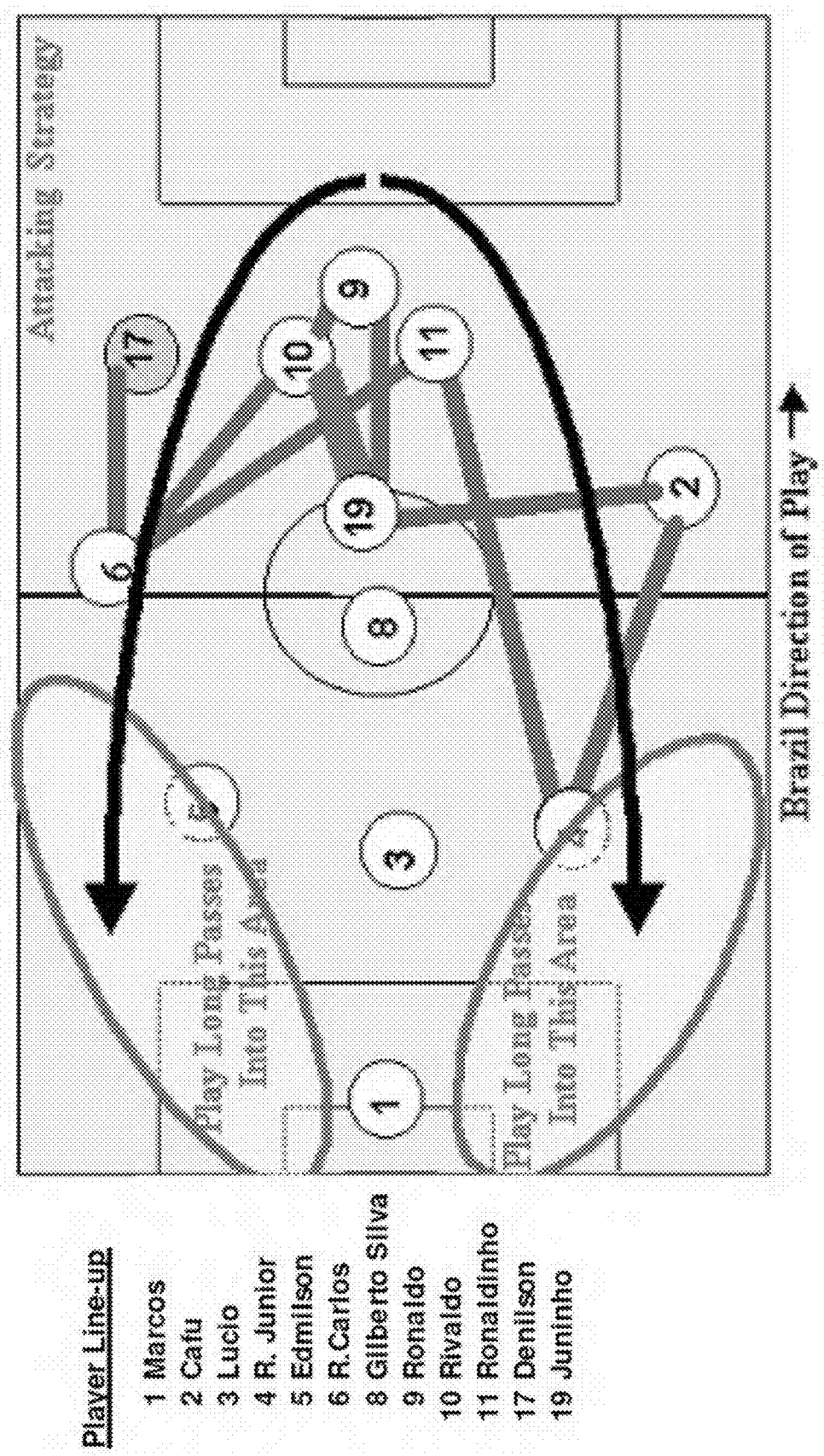

FIG. 73F shows an example of how to attack against Brazil. Brazil plays with a very forward, aggressive style, leaving the back weakly defended. The opposing team could put two fast players on the sides, one on the right and one on the left, and wait for opportunities to counter-attack. Do not pass the ball into the middle because Brazil midfielders are very good in keeping possessions of the ball. Pass long balls to the two attacking players on the sides in the circled areas and try to create one-on-one opportunities.

In some embodiments, the performance of a particular player can be improved by using a role model, as described in other portions of this patent document. FIGS. 74A-74D illustrate the various facets of a role model that can used in conjunction with the described embodiments (e.g., the spine and the pass distribution matrix) to improve certain specific skills of a that player. FIGS. 74A-74D show the completed passes, a comparison of goals scored and shots on goal, the impact passes (both direct and indirect), and the intercepted passes for Brandi Chastain, which can be used to tailor a training regimen and define goals for that player.

Figure 75:
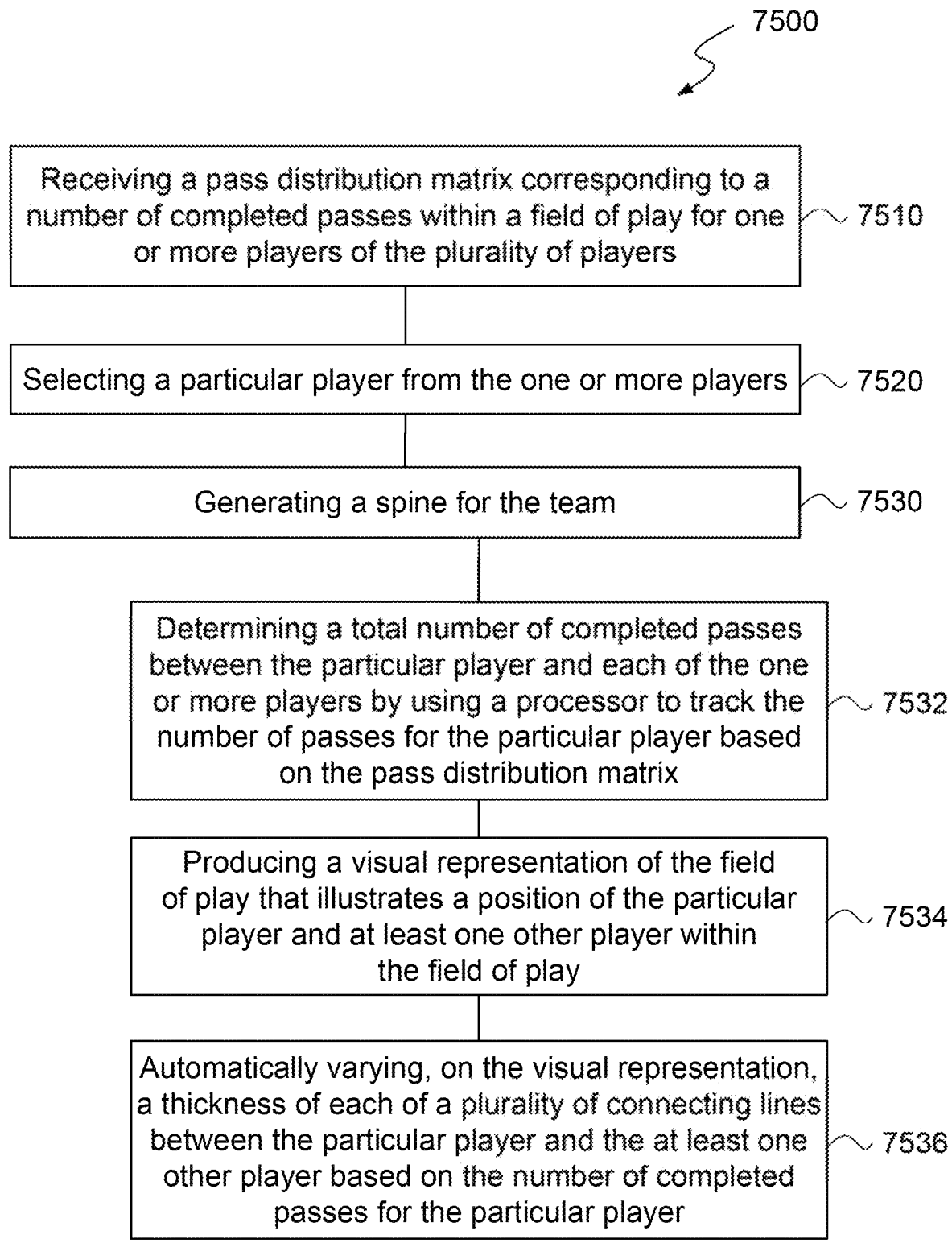
FIG. 75 illustrates a flowchart of an example method for improving an efficacy of a team comprising a plurality of players, in accordance with the described embodiments.

In some embodiments, a method for improving an efficacy of a team comprising a plurality of players, using the spine and pass distribution matrix techniques described above, is shown in FIG. 75. As shown therein, the method 7500 includes, at operation 7510, receiving a pass distribution matrix corresponding to a number of completed passes within a field of play for one or more players of the plurality of players.

The method 7500 includes, at operation 7520, selecting a particular player from the one or more players.

The method 7500 includes, at operation 7530, generating a spine for the team.

In some embodiments, operation 7530 includes, at operation 7532, determining a total number of completed passes between the particular player and each of the one or more players by using a processor to track the number of passes for the particular player based on the pass distribution matrix.

In some embodiments, operation 7530 includes, at operation 7534, producing a visual representation of the field of play that illustrates a position of the particular player and at least one other player within the field of play, the visual display further including connecting lines indicative of a number and direction of passes between the particular player and at least one other player.

In some embodiments, operation 7530 includes, at operation 7536, automatically varying, on the visual representation, a thickness of each of a plurality of connecting lines between the particular player and the at least one other player based on the number of completed passes for the particular player, wherein the thickness is representative of the number of completed passes.

In some embodiments, the pass distribution matrix further includes information corresponding to a number of kicks that scored a goal (also referred to as "goal scored") or a number of kicks that were attempts to score a goal (also referred to as a "shot on goal"), and the visual display further includes connecting lines indicative of a number and direction of a kick that scored a goal or kick that was an attempt to score a goal between the particular player and a position in or near the goal.

In some embodiments, the pass distribution matrix further includes information corresponding to a number of a particular type of kick, and the particular type of kick is one of the completed pass, an incomplete pass, a direct impact pass, an indirect impact pass, or an intercepted pass. In an example, the pass distribution may be generated based on the methods and techniques described in the data collection section.

In some embodiments, the visual representation further includes a position of additional players and additional connecting lines that illustrate directions and numbers of the particular type of kick between the particular player and the additional players. In an example, the visual representation can automatically be updated as data from new (or additional) games are incorporated into the pass distribution matrix.

In some embodiments, method 7500 further includes the operations of determining the total number of incomplete passes between the particular player and each of the one or more players, and providing, on the visual representation of the field, a symbol indicative of each of the incomplete passes.

In some embodiments, method 7500 further includes the operations of determining a total number of shots on goal by the particular player, and providing, on the visual representation of the field, a symbol indicative of each of the shots on goal.

In some embodiments, method 7500 further includes the operations of determining the total number of indirect impact passes between the particular player and each of the one or more players, and providing, on the visual representation of the field, a symbol indicative of each of the indirect impact passes.

In some embodiments, method 7500 further includes the operations of determining the total number of direct impact passes between the particular player and each of the one or more players, and providing, on the visual representation of the field, a symbol indicative of each of the direct impact passes.

In some embodiments, method 7500 further includes the operations of determining the total number of intercepted passes between the particular player and each of the one or more players, and providing, on the visual representation of the field, a symbol indicative of each of the intercepted passes.

In some embodiments, method 7500 further includes the operation of obtaining information associated with a role model of the particular player, the information being used to determine a desired number of the particular type of kick by the particular player.

Figure 74A:
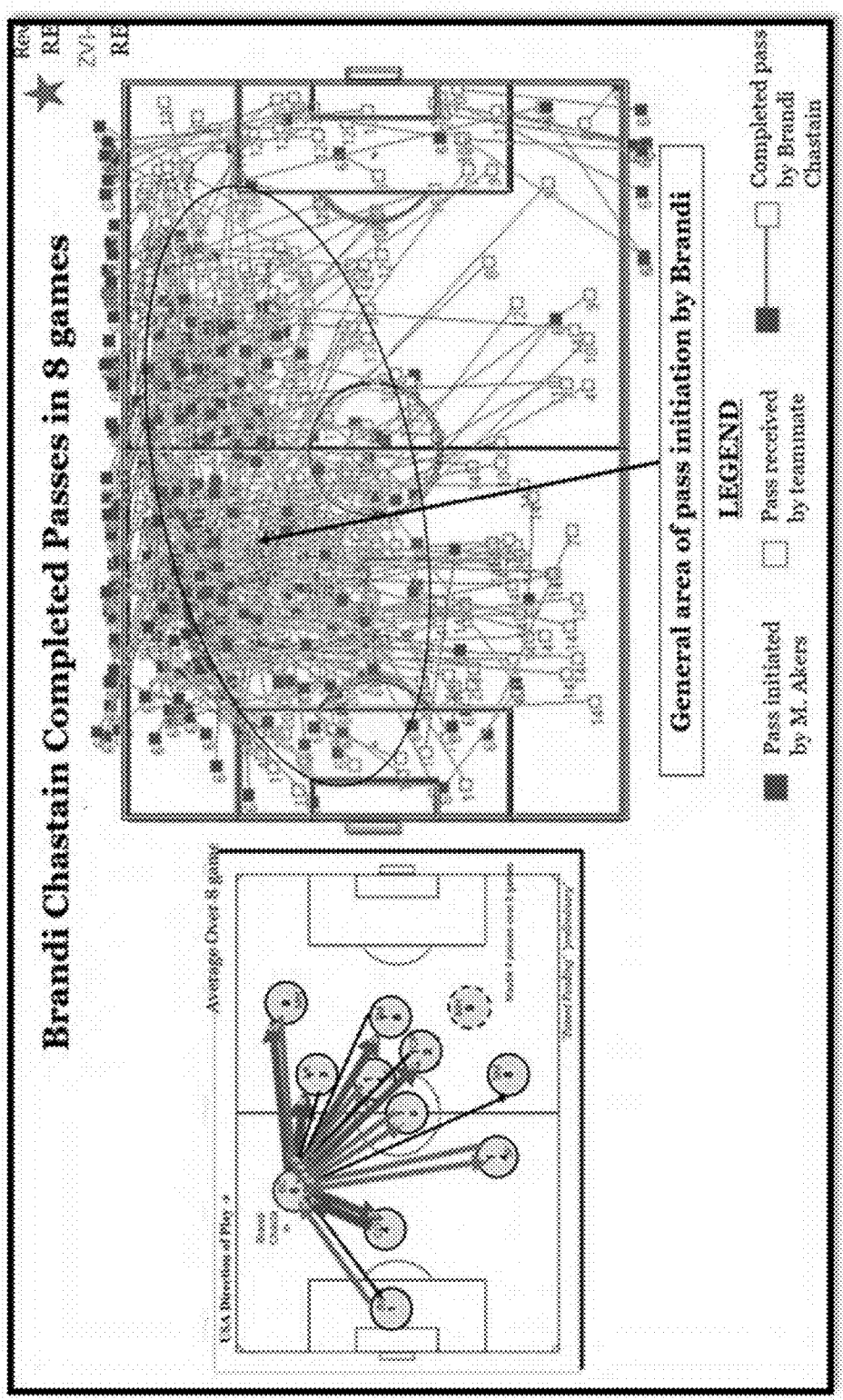
FIGS. 74A-74D illustrate an example of various facets of a role model used to improve the performance of a particular player, in accordance with the described embodiments.

In some embodiments, method 7500 further includes the operations of using the spine to compare the completed passes by the particular player to the desired number of passes determined from the role model (e.g., as illustrated in FIG. 74A), and providing an indication regarding whether a corresponding goal was achieved.

Figure 74B:
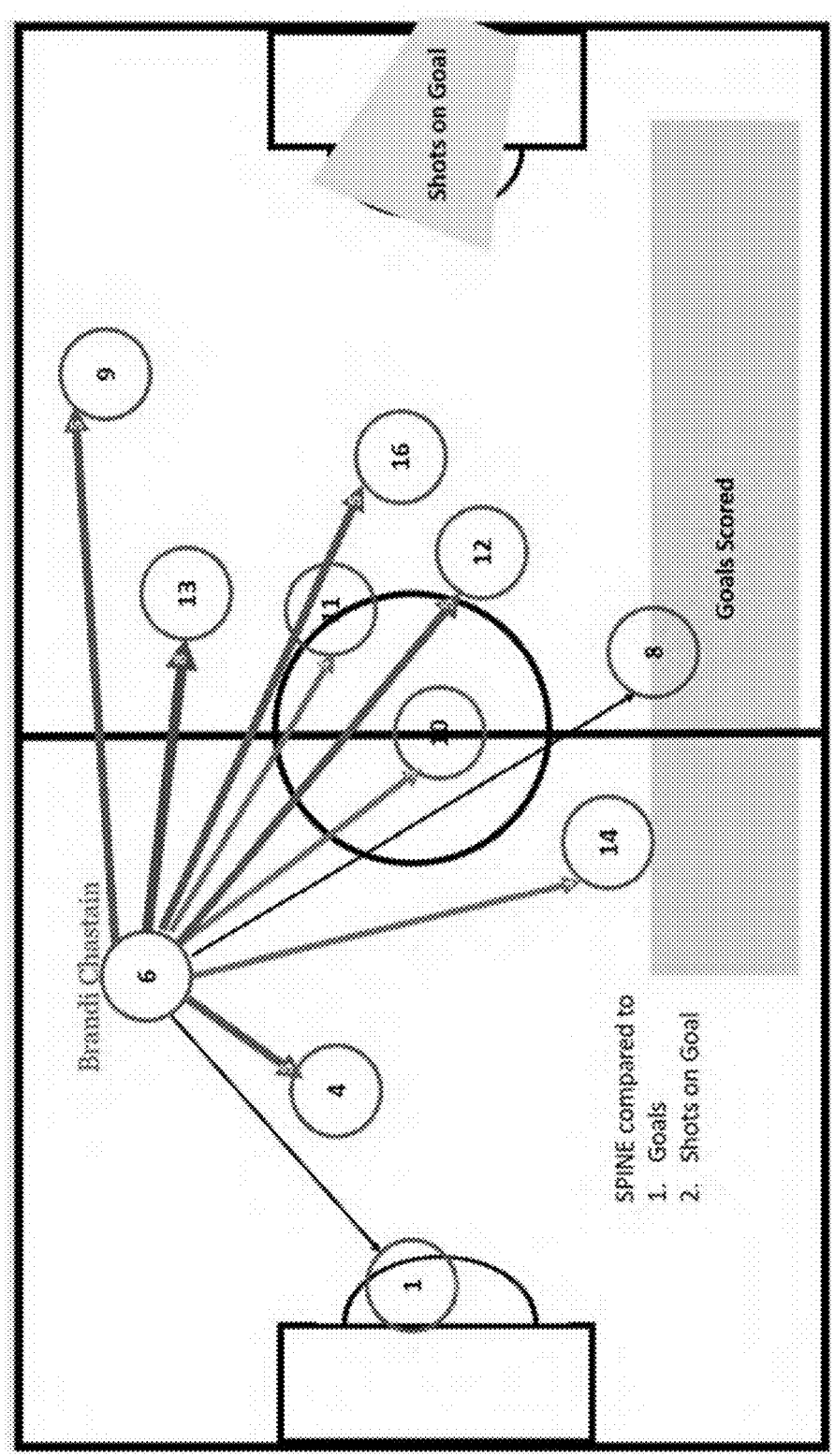

In some embodiments, method 7500 further includes the operations of using the spine to compare goals scored by the particular player to a desired number of goals scored determined from the role model (e.g., as illustrated in FIG. 74B), and providing an indication regarding whether a corresponding goal was achieved.

Figure 74C:
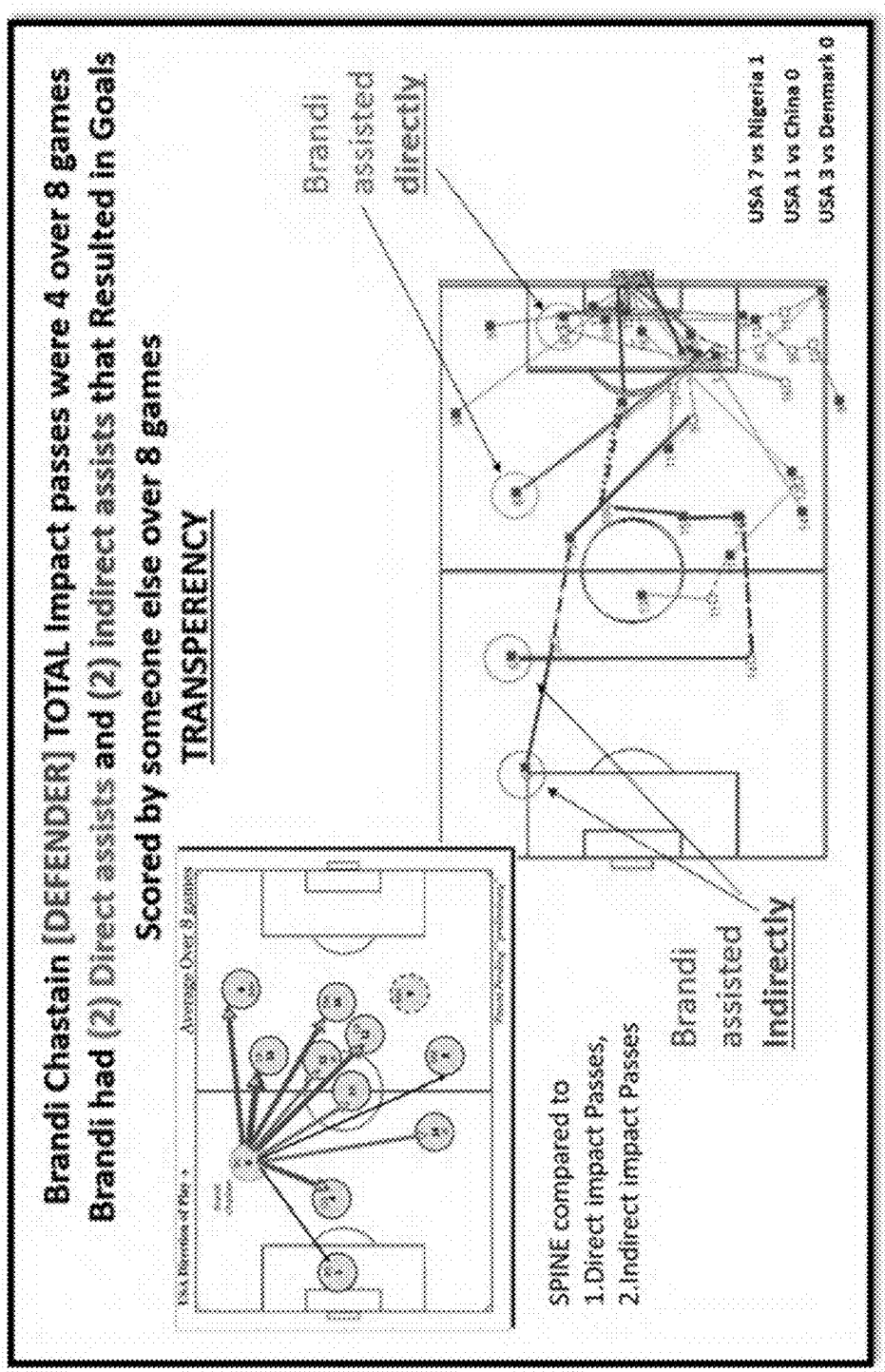

In some embodiments, method 7500 further includes the operations of using the spine to compare the direct impact passes by the particular player to a desired number of direct impact passes determined from the role model (e.g., as illustrated in FIG. 74C), and providing an indication regarding whether a corresponding goal was achieved.

Figure 74D:
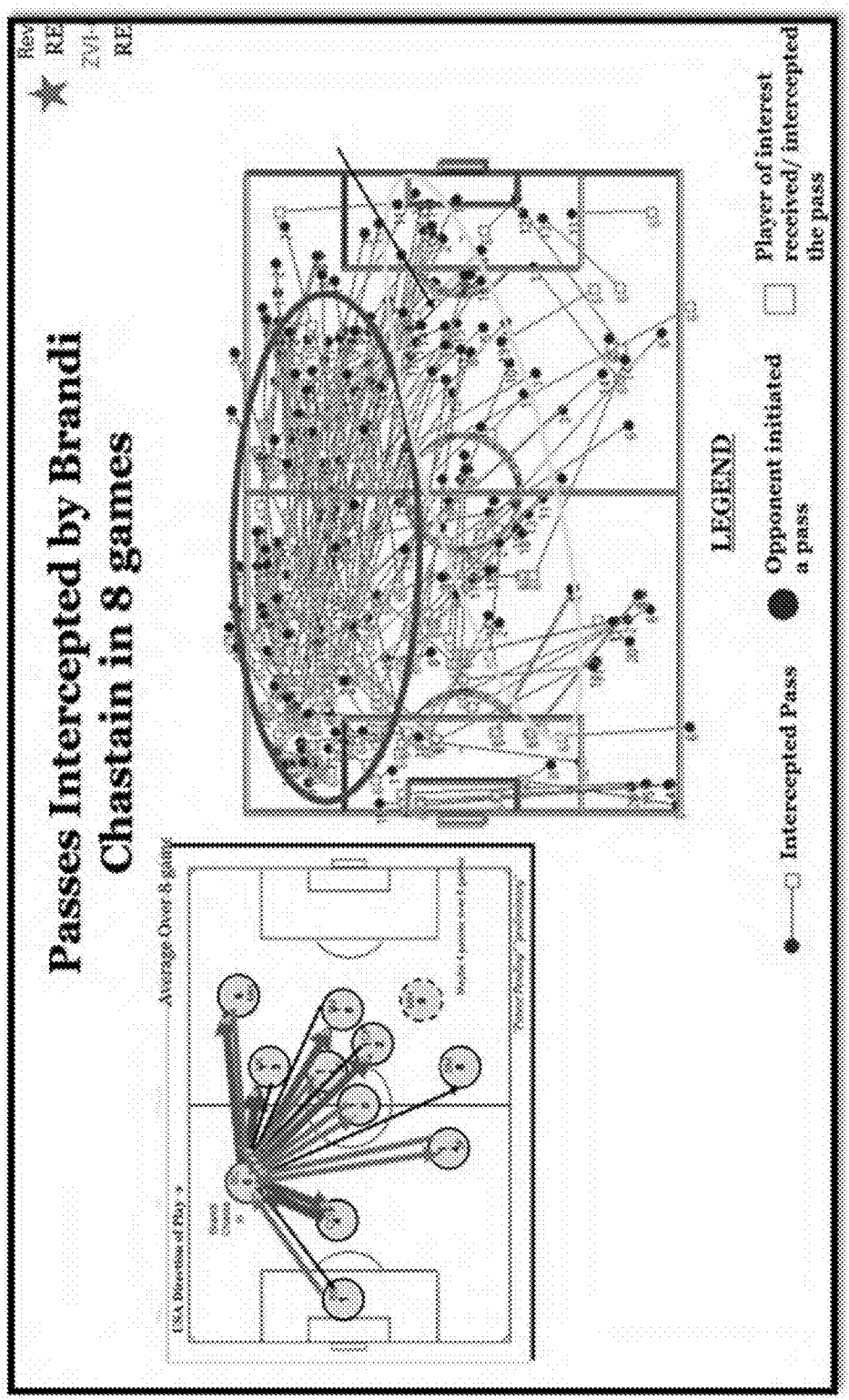

In some embodiments, method 7500 further includes the operations of using the spine to compare the intercepted passes by the particular player to a desired number of intercepted passes determined from the role model (e.g., as illustrated in FIG. 74D), and providing an indication regarding whether a corresponding goal was achieved.

In some embodiments, method 7500 further includes the operation of providing, based on the information associated with the role model, a plurality of indications to enable the particular player to achieve the desired number of the particular type of kick. In an example, and as described in this patent document, the plurality of indications comprises an indication associated with an exercise regimen of the particular player, an indication associated with a nutrition goal of the particular player, or an indication of a practice schedule for the particular player.

In some embodiments, each entry in the pass distribution matrix comprises a timestamp relative to a starting time of a game, a first location on the field of a first player that initiated the particular type of kick, and a second location on the field corresponding to a result of the particular type of kick.

In some embodiments, method 7500 further includes the operation of determining, based on the pass distribution matrix, a centrality metric for each of the one or more players, wherein the centrality metric of a first player corresponds to an area on the field of play on which the first player spent the most time interacting with other players in the team, and wherein the thickness of the plurality of connecting lines is further based on the centrality metrics.

In some embodiments, the pass distribution matrix is generated by processing a video stream of the game using a software product.

In some embodiments, the software product comprises one or more artificial intelligence (AI)-based image processing modules.

In some embodiments, method 7500 further includes the operation of making a recommendation, based on the thickness of a subset of the plurality of connecting lines, regarding a playing strategy for the particular player.

In an example, the playing strategy comprises increasing the number of passes from the particular player to another player. In another example, the playing strategy comprises moving a centrality metric of the particular player toward one or more opponents, the centrality metric of the particular player corresponding to an area on the field on which the particular player spent the most time interacting with other players in the team.

In some embodiments, the connecting lines on the visual representation are further color coded to represent different ranges of the number of completed passes by the particular player.

The described embodiments can be implemented using one or more software applications, which can be used for each position on the field (e.g., all 11 positions for 2 different play systems—4-4-2, 4-2-4, and 4-3-3), and for different levels of play (e.g., boys, girls, men, women, professional, semi-professional, amateur, etc.).

In some embodiments, all the data collected and/or produced in accordance with the disclosed embodiments can be stored at a central data base, such as a cloud-based database. In other embodiments, multiple databases are used for storage of such information.

Figure 76:
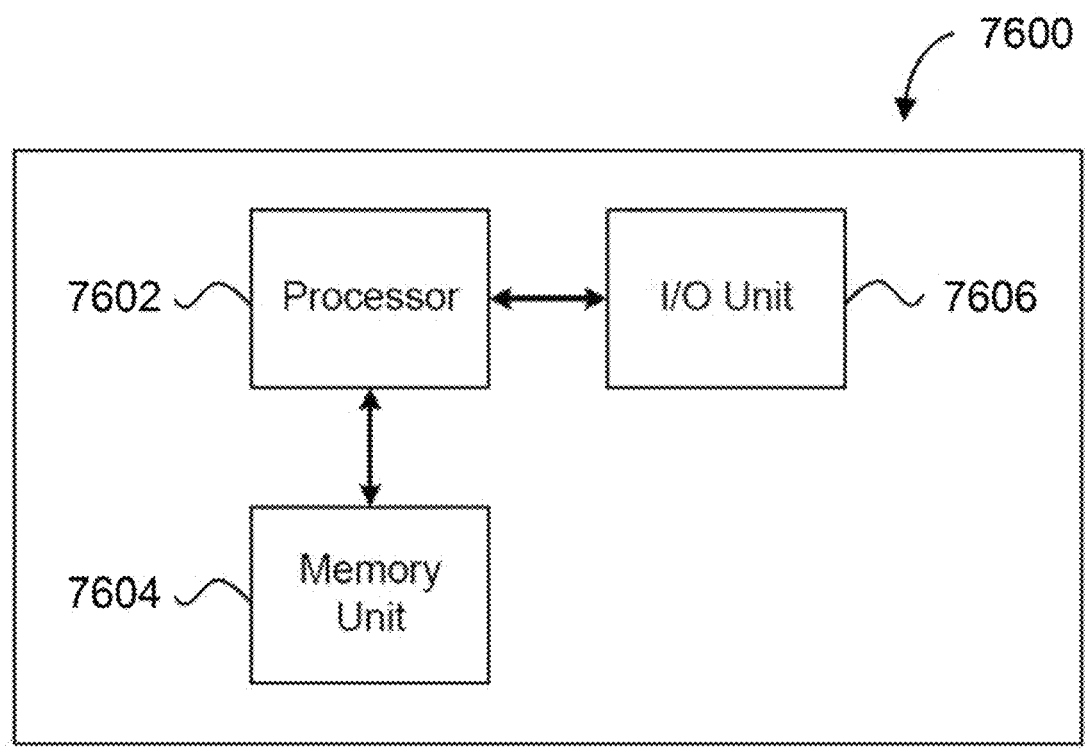
FIG. 76 is an example diagram illustrating a device that can be configured to implement the described embodiments.

FIG. 76 shows a block diagram of an example embodiment of a device (or apparatus, hardware device or implementation) 7600 that implements the disclosed technology. The device includes a processor 7602 in communication with a memory unit 7604 and an input/output (I/O) unit 7606. The processor 7602 is configured to process data, and the memory unit 7604 is in communication with the processor to store and/or buffer the data. To support various functions of the device, the processor can be included to interface with and control operations of other devices, e.g., via the I/O unit 7606.

In various implementations, the processor 7602 can include one or more processors, e.g., including but not limited to microprocessors such as a central processing unit (CPU), microcontrollers, or the like. The memory unit 7604 can include and store processor-executable code, which when executed by the processor, configures the device to perform various operations, e.g., such as receiving information, commands, and/or data, processing information and data, and transmitting or providing information/data to another device. The memory unit can store other information and data, such as instructions, software, values, images, and other data processed or referenced by processor. For example, various types of Random Access Memory (RAM) devices, Read Only Memory (ROM) devices, Flash Memory devices, and other suitable storage media can be used to implement storage functions of memory unit. In some implementations, the device includes an input/output unit (I/O) 7606 to interface the processor and/or memory unit to other modules, units or devices associated with the system, and/or external devices. For example, the I/O unit can connect to an external interface, source of data storage, or display device. Various types of wired or wireless interfaces compatible with typical data communication standards, such as Universal Serial Bus (USB), IEEE 1394 (FireWire), Bluetooth, Bluetooth low energy (BLE), ZigBee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3 G/4G/ LTE cellular communication methods, and parallel interfaces, can be used to communicate data with the device via the I/O unit. In some implementations, for example, the device 7600 includes a wireless communications unit, e.g., such as a transmitter (Tx) or a transmitter/receiver (Tx/Rx) unit In such implementations, for example, the I/O unit can interface the processor and memory unit with the wireless communications unit to utilize various types of wireless interfaces, such as the examples described above. The I/O unit can interface with other external interfaces, sources of data storage, and/or visual or audio display devices, etc. to retrieve and transfer data and information that can be processed by the processor, stored in the memory unit, or exhibited on an output unit of a user device (e.g., display screen of a computing device) or an external device.

The disclosed embodiments can be implemented using devices, such as personal computers, laptops, tablets, smart phones, and other devices. At least a portion of the disclosed techniques can be implemented as an application that is loaded on a handheld device. The application can, for example, be initiated by the user to enable the user to enter various information for digestion and processing by the system, to view the user's goals, performance results, next steps and other information that may be presented to the use in graphical, text, video, image, and/or audio formats. The application that resides on the user device may be in communication with a database (e.g., cloud-based services).

The operations that are described in the present application can be implemented via software, hardware, or combinations thereof. Certain aspects of the disclosed embodiments can be implemented as a device that includes a processor, and a memory comprising processor executable code, the processor executable code, when executed by the processor, configures the device to perform any one of and/or all operations that are described in the present application. In some examples, the disclosed embodiments can be implemented using a device that comprises at least one processor and/or controller, at least one memory unit that is in communication with the processor, and at least one communication unit that enables the exchange of data and information, directly or indirectly, through a communication link with other entities, devices, databases and networks. The communication unit may provide wired and/or wireless communication capabilities in accordance with one or more communication protocols, and therefore it may comprise the proper transmitter/receiver antennas, circuitry, and ports, as well as the encoding/decoding capabilities that may be necessary for proper transmission and/or reception of data and other information. Such an exemplary device may be integrated as part of a larger device carry out some or all of the operations that are described in the present application.

It should be noted that while the above description has been described in terms of the sport of soccer to facilitate understanding of the disclosed concepts, the disclosed embodiments are also applicable to other sports, such as baseball, basketball, volleyball, hockey, water polo, hand ball, and the like.

It is understood that the operations that are described in the present application are presented in a particular sequential order in order to facilitate understanding of the underlying concepts. It is understood, however, that such operations may be conducted in a different sequential order, and further, additional, or fewer steps may be used to carry out the various disclosed operations.

Various embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, systems, and article of manufacture.

What is claimed is:

1. A method for assessing and analyzing performance of a player or a team comprising a plurality of players, the method comprising:
   receiving a pass distribution matrix corresponding to a number of completed passes within a field of play for one or more players of the plurality of players;
   selecting a particular player from the one or more players; and
   generating a spine for the team including:
      determining a total number of completed passes between the particular player and each of the one or more players by using a processor to track the number of passes for the particular player based on the pass distribution matrix,
      producing a visual representation of the field of play that illustrates a position of the particular player and at least one other player within the field of play, the visual display further including connecting lines indicative of a number and direction of passes between the particular player and at least one other player, and
      automatically varying, on the visual representation, a thickness of each of a plurality of connecting lines between the particular player and the at least one other player based on the number of completed passes for the particular player, wherein the thickness is representative of the number of completed passes.

2. The method of claim 1, wherein the pass distribution matrix further includes information corresponding to a number of kicks that scored a goal or a number of kicks that were attempts to score a goal, and wherein the visual display further includes connecting lines indicative of a number and direction of a kick that scored a goal or a kick that was an attempt to score a goal between the particular player and a position in or near the goal.

3. The method of claim 1, wherein the pass distribution matrix further includes information corresponding to a number of a particular type of kick, and wherein the particular type of kick is one of the completed pass, an incomplete pass, a direct impact pass, an indirect impact pass, or an intercepted pass.

4. The method of claim 3, wherein the visual representation further includes a position of additional players and additional connecting lines that illustrate directions and numbers of the particular type of kick between the particular player and the additional players.

5. The method of claim 3, further comprising:
   determining the total number of incomplete passes between the particular player and each of the one or more players; and
   providing, on the visual representation of the field, a symbol indicative of each of the incomplete passes.

6. The method of claim 3, further comprising:
determining a total number of shots on goal by the particular player; and
providing, on the visual representation of the field, a symbol indicative of each of the shots on goal.

7. The method of claim 3, further comprising:
determining the total number of indirect impact passes between the particular player and each of the one or more players; and
providing, on the visual representation of the field, a symbol indicative of each of the indirect impact passes.

8. The method of claim 3, further comprising:
determining the total number of direct impact passes between the particular player and each of the one or more players; and
providing, on the visual representation of the field, a symbol indicative of each of the direct impact passes.

9. The method of claim 3, further comprising:
determining the total number of intercepted passes between the particular player and each of the one or more players; and
providing, on the visual representation of the field, a symbol indicative of each of the intercepted passes.

10. The method of claim 3, further comprising:
obtaining information associated with a role model of the particular player, the information being used to determine a desired number of the particular type of kick by the particular player.

11. The method of claim 10, further comprising:
using the spine to compare the completed passes by the particular player to the desired number of passes determined from the role model; and
providing an indication regarding whether a corresponding goal was achieved.

12. The method of claim 10, further comprising:
using the spine to compare goals scored by the particular player to a desired number of goals scored determined from the role model; and
providing an indication regarding whether a corresponding goal was achieved.

13. The method of claim 10, further comprising:
using the spine to compare the direct impact passes by the particular player to a desired number of direct impact passes determined from the role model; and
providing an indication regarding whether a corresponding goal was achieved.

14. The method of claim 10, further comprising:
using the spine to compare the intercepted passes by the particular player to a desired number of intercepted passes determined from the role model; and
providing an indication regarding whether a corresponding goal was achieved.

15. The method of claim 10, further comprising:
providing, based on the information associated with the role model, a plurality of indications to enable the particular player to achieve the desired number of the particular type of kick,
wherein the plurality of indications comprises an indication associated with an exercise regimen of the particular player, an indication associated with a nutrition goal of the particular player, or an indication of a practice schedule for the particular player.

16. The method of claim 3, wherein each entry in the pass distribution matrix comprises a timestamp relative to a starting time of a game, a first location on the field of a first player that initiated the particular type of kick, and a second location on the field corresponding to a result of the particular type of kick.

17. The method of claim 1, further comprising:
determining, based on the pass distribution matrix, a centrality metric for each of the one or more players, wherein the centrality metric of a first player corresponds to an area on the field of play on which the first player spent the most time interacting with other players in the team, and wherein the thickness of the plurality of connecting lines is further based on the centrality metrics.

18. The method of claim 1, wherein the pass distribution matrix is generated by processing a video stream of the game using a software product.

19. The method of claim 18, wherein the software product comprises one or more artificial intelligence (AI)-based image processing modules.

20. The method of claim 1, further comprising:
making a recommendation, based on the thickness of a subset of the plurality of connecting lines, regarding a playing strategy for the particular player.

21. The method of claim 20, wherein the playing strategy comprises increasing the number of passes from the particular player to another player.

22. The method of claim 20, wherein the playing strategy comprises moving a centrality metric of the particular player toward one or more opponents, wherein the centrality metric of the particular player corresponds to an area on the field on which the particular player spent the most time interacting with other players in the team.

23. The method of claim 1, wherein the connecting lines on the visual representation are further color coded to represent different ranges of the number of completed passes by the particular player.

24. A system for improving an efficacy of a team comprising a plurality of players, comprising:
a processor and a memory including instructions stored thereupon, wherein the instructions upon execution by the processor cause the processor to:
receive a pass distribution matrix corresponding to a number of completed passes within a field of play for one or more players of the plurality of players;
select a particular player from the one or more players; and
generate a spine for the team,
wherein generating the spine for the team further causes the processor to:
determine a total number of completed passes between the particular player and each of the one or more players by using a processor to track the number of passes for the particular player based on the pass distribution matrix,
produce a visual representation of the field of play that illustrates a position of the particular player and at least one other player within the field of play, the visual display further including connecting lines indicative of a number and direction of passes between the particular player and at least one other player, and
automatically vary, on the visual representation, a thickness of each of a plurality of connecting lines between the particular player and the at least one other player based on the number of completed passes for the particular player, wherein the thickness is representative of the number of completed passes.

25. A non-transitory computer-readable storage medium having instructions stored thereupon for improving an efficacy of a team comprising a plurality of players, comprising:
- instructions for receiving a pass distribution matrix corresponding to a number of completed passes within a field of play for one or more players of the plurality of players;
- instructions for selecting a particular player from the one or more players; and
- instructions for generating a spine for the team including:
  - instructions for determining a total number of completed passes between the particular player and each of the one or more players by using a processor to track the number of passes for the particular player based on the pass distribution matrix,
  - instructions for producing a visual representation of the field of play that illustrates a position of the particular player and at least one other player within the field of play, the visual display further including connecting lines indicative of a number and direction of passes between the particular player and at least one other player, and
  - instructions for automatically varying, on the visual representation, a thickness of each of a plurality of connecting lines between the particular player and the at least one other player based on the number of completed passes for the particular player, wherein the thickness is representative of the number of completed passes.

* * * * *